United States Patent
Klein et al.

(10) Patent No.: US 11,937,793 B2
(45) Date of Patent: Mar. 26, 2024

(54) BIOPSY DEVICE

(71) Applicant: Limaca Medical Ltd., Misgav (IL)

(72) Inventors: Assaf Klein, Kibbutz HaMaApil (IL); Iyad Khamaysi, Kfar-Kana (IL); Sefi Shachrur, Pardes Hana Karkur (IL)

(73) Assignee: Limaca Medical Ltd., Ein HaEmek (IL)

( * ) Notice: Subject to any disclaimer, the term of this patent is extended or adjusted under 35 U.S.C. 154(b) by 172 days.

(21) Appl. No.: 16/967,738

(22) PCT Filed: Feb. 7, 2019

(86) PCT No.: PCT/IL2019/050156
§ 371 (c)(1),
(2) Date: Aug. 6, 2020

(87) PCT Pub. No.: WO2019/155472
PCT Pub. Date: Aug. 15, 2019

(65) Prior Publication Data
US 2021/0038202 A1    Feb. 11, 2021

Related U.S. Application Data

(60) Provisional application No. 62/787,783, filed on Jan. 3, 2019, provisional application No. 62/722,907, filed (Continued)

(51) Int. Cl.
*A61B 10/02* (2006.01)
*A61B 10/04* (2006.01)

(52) U.S. Cl.
CPC ......... *A61B 10/0266* (2013.01); *A61B 10/04* (2013.01); *A61B 2010/0208* (2013.01)

(58) Field of Classification Search
None
See application file for complete search history.

(56) References Cited

U.S. PATENT DOCUMENTS

| | | | | |
|---|---|---|---|---|
| 6,086,543 A | * | 7/2000 | Anderson | A61B 10/0233 600/567 |
| 6,086,544 A | * | 7/2000 | Hibner | A61B 10/0275 600/568 |

(Continued)

FOREIGN PATENT DOCUMENTS

| | | |
|---|---|---|
| CN | 1700887 | 11/2005 |
| CN | 1827050 | 9/2006 |

(Continued)

OTHER PUBLICATIONS

Supplementary European Search Report and the European Search Opinion dated Sep. 10, 2021 From the European Patent Office Re. Application No. 19750735.3. (8 Pages).

(Continued)

*Primary Examiner* — Benjamin S Melhus

(57) ABSTRACT

A soft tissue biopsy device including:
  an elongated handle including a gripping member;
  an elongated flexible shaft mechanically comprising a hollow distal sampling portion with an internal lumen and a distal opening facing a soft tissue;
  a driving unit configured to rotate the sampling portion with a speed in a range of 100 rounds-per-minute (RPM) to 10,000 RPM while the sampling portion axially advances into said soft tissue.

29 Claims, 49 Drawing Sheets

Related U.S. Application Data on Aug. 26, 2018, provisional application No. 62/627,786, filed on Feb. 8, 2018.

(56) References Cited

U.S. PATENT DOCUMENTS

| | | | |
|---|---|---|---|
| 6,120,462 A | 9/2000 | Hibner et al. | |
| 6,689,072 B2 * | 2/2004 | Kaplan | A61B 10/0233 |
| | | | 600/564 |
| 7,722,549 B2 | 5/2010 | Nakao | |
| 7,850,620 B2 | 12/2010 | Miller et al. | |
| 8,597,204 B2 | 12/2013 | Flatland et al. | |
| 8,685,635 B2 | 4/2014 | Bellomo et al. | |
| 9,155,527 B2 * | 10/2015 | Vetter | A61B 10/06 |
| 9,456,807 B2 | 10/2016 | Vetter et al. | |
| 9,572,551 B2 * | 2/2017 | Fumex | A61B 10/025 |
| 9,717,564 B2 | 8/2017 | Miller et al. | |
| 10,231,750 B2 * | 3/2019 | Vetter | A61B 17/3207 |
| 2006/0116605 A1 * | 6/2006 | Nakao | A61B 10/0266 |
| | | | 600/566 |
| 2007/0149881 A1 * | 6/2007 | Rabin | A61C 1/07 |
| | | | 600/471 |
| 2008/0228104 A1 * | 9/2008 | Uber | A61B 10/0233 |
| | | | 600/576 |
| 2009/0287114 A1 | 11/2009 | Lee et al. | |
| 2010/0106055 A1 | 4/2010 | Heske et al. | |
| 2010/0013085 A1 † | 5/2010 | Parkter | |
| 2010/0130850 A1 | 5/2010 | Pakter | |
| 2010/0023485 A1 † | 9/2010 | Stoianovici | |
| 2011/0077552 A1 * | 3/2011 | Thompson | A61B 10/0275 |
| | | | 600/568 |
| 2012/0209141 A1 * | 8/2012 | Peliks | A61B 17/32002 |
| | | | 600/564 |
| 2014/0100477 A1 * | 4/2014 | Ehlert | A61B 10/0096 |
| | | | 600/567 |
| 2014/0249448 A1 * | 9/2014 | Furlong | A61B 1/00119 |
| | | | 600/563 |
| 2014/0336530 A1 | 11/2014 | Vetter et al. | |
| 2015/0018710 A1 * | 1/2015 | Furlong | A61B 1/00094 |
| | | | 600/563 |
| 2015/0018711 A1 * | 1/2015 | Furlong | A61B 10/0275 |
| | | | 600/565 |
| 2015/0031951 A1 * | 1/2015 | Furlong | A61B 1/00133 |
| | | | 600/106 |
| 2015/0032024 A1 * | 1/2015 | Furlong | A61B 17/221 |
| | | | 600/566 |
| 2015/0057566 A1 | 2/2015 | Vetter et al. | |
| 2015/0057567 A1 | 2/2015 | Vetter et al. | |
| 2015/0057573 A1 | 2/2015 | Vetter et al. | |
| 2015/0133985 A1 | 5/2015 | Vetter et al. | |
| 2015/0141869 A1 * | 5/2015 | Costello | A61B 10/0266 |
| | | | 600/568 |
| 2015/0150541 A1 * | 6/2015 | Fumex | A61B 10/025 |
| | | | 600/567 |
| 2016/0081675 A1 | 3/2016 | Golden et al. | |
| 2017/0056040 A1 | 3/2017 | Vetter et al. | |
| 2017/0238913 A1 * | 8/2017 | Schässburger | A61B 10/0233 |
| 2017/0319188 A1 * | 11/2017 | Furlong | A61B 10/04 |
| 2018/0214171 A1 * | 8/2018 | Ryan, Jr. | A61B 17/32002 |
| 2018/0360495 A1 * | 12/2018 | Adams | A61B 10/06 |
| 2022/0054112 A9 * | 2/2022 | Peliks | A61B 10/0266 |

FOREIGN PATENT DOCUMENTS

| | | |
|---|---|---|
| CN | 107205734 | 9/2017 |
| EP | 0966920 | 12/1999 |
| EP | 1040790 | 10/2000 |
| EP | 1923004 | 5/2008 |
| EP | 2997902 | 3/2016 |
| JP | 2000-312679 | 11/2000 |
| JP | 2005-199044 | 7/2005 |
| JP | 2008-528207 | 7/2008 |
| JP | 2012-524618 | 10/2012 |
| WO | WO 2009/143534 | 11/2009 |
| WO | WO 2016/144834 | 9/2016 |
| WO | WO 2019/155472 | 8/2019 |
| WO | WO 2019/155472 A9 | 12/2019 |

OTHER PUBLICATIONS

International Preliminary Report on Patentability dated Aug. 20, 2020 From the International Bureau of WIPO Re. Application No. PCT/IL2019/050156. (23 Pages).

International Search Report and the Written Opinion dated May 21, 2019 From the International Searching Authority Re. Application No. PCT/IL2019/050156. (23 Pages).

Teleflex "Access Driver. Bone Marrow Biopsy Needle Sets", Teleflex, ARROW® OnControl®, Powered Bone Access, Video, 2018.

Teleflex "Diagnosing and Monitoring: Easier, More Accurate Diagnosis and Treatment Monitoring", Teleflex, ARROW® OnControl®, Powered Bone Access, ARROW® OnControl® Core Specimen, Manual Needle Core Sample, Video, 2018.

Teleflex "Ensures Better Overall Patient Experience", ARROW® OnControl®, Powered Bone Access, Marrow Biopsy Procedure, Video, 2018.

Teleflex "Performing the Biopsy or Aspiration: Significantly Less Patient Pain During and After the Procedure", Teleflex, ARROW® OnControl®, Powered Bone Access System, Video, 2018.

Teleflex "Raising the Standard of Bone Marrow Biopsies", Teleflex, ARROW® OnControl®, Powered Bone Access, Video, 2018.

Notice of Reason(s) for Rejection Dated From the Japan Patent Office Re. Application No. dated Jan. 10, 2023 and Its Translation Into English. (11 Pages).

Notification of Office Action dated Feb. 7, 2023 From the State Intellectual Property Office of the People's Republic of China Re. Application No. 201980017865.X. (11 Pages).

Translation Datad Feb. 24, 2023 of Notification of Office Action and Search Report dated Feb. 7, 2023 From the State Intellectual Property Office of the People's Republic of China Re. Application No. 201980017865.X. (7 Pages).

Notification of Office Action and Search Report dated Aug. 9, 2023 From the National Intellectual Property Administration of the People's Republic of China Re. Application No. 201980017865.X and Its Machine Translation Into English. (41 Pages).

Office Action dated Aug. 28, 2023 From the Israel Patent Office Re. Application No. 276582. (4 Pages).

Translation Dated Aug. 25, 2023 of Notification of Office Action dated Aug. 9, 2023 From the State Intellectual Property Office of the People's Republic of China Re. Application No. 201980017865.X. (5 pages).

Decision on Rejection Dated Jan. 24, 2024 From the State Intellectual Property Office of the People's Republic of China Re. Application No. 201980017865.X. and Its Machine Translation. (40 Pages).

Peidong Han et al., Study of the Effect of Cannula Rotation on Tissue Cutting for Needle Biopsy, 1584-1590, Nov. 2013, Medical Engineering & Physics, vol. 35, Issue 11, hereinafter Han.†

* cited by examiner
† cited by third party

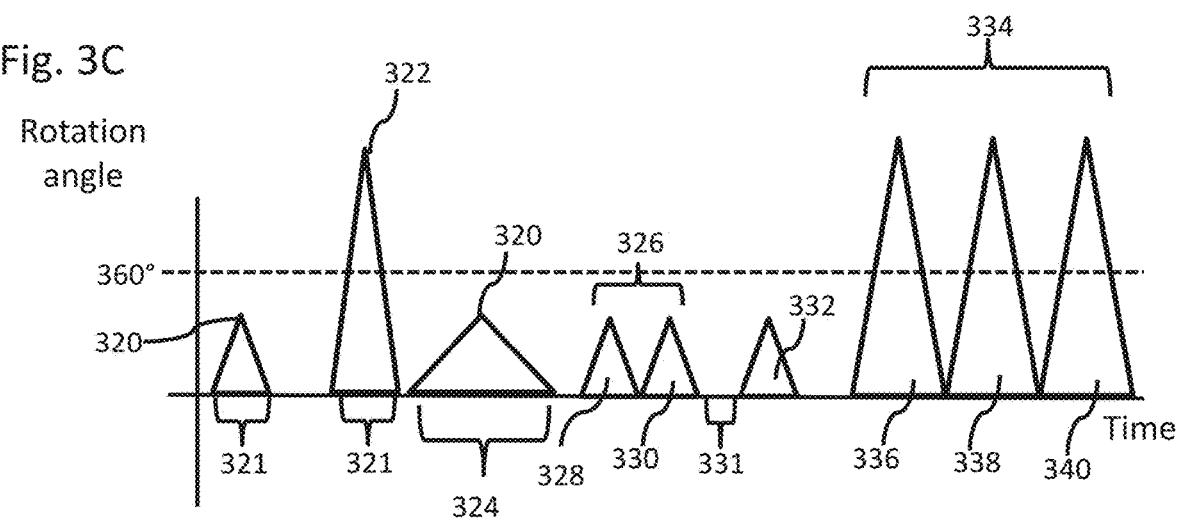
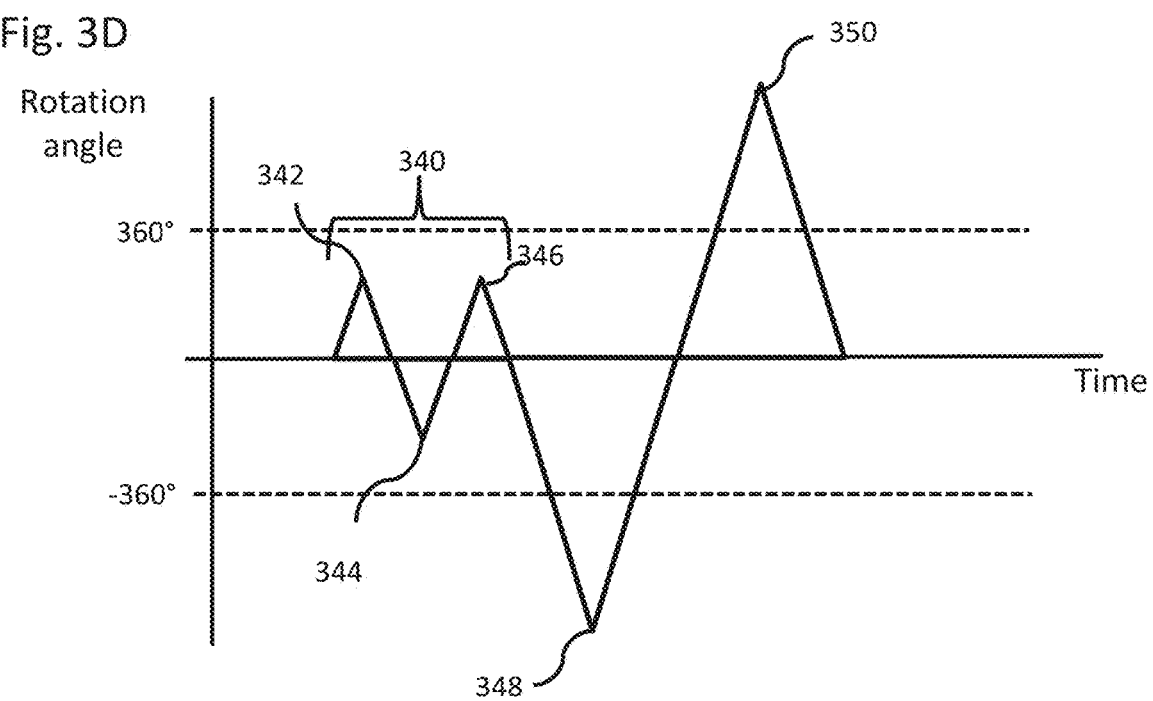

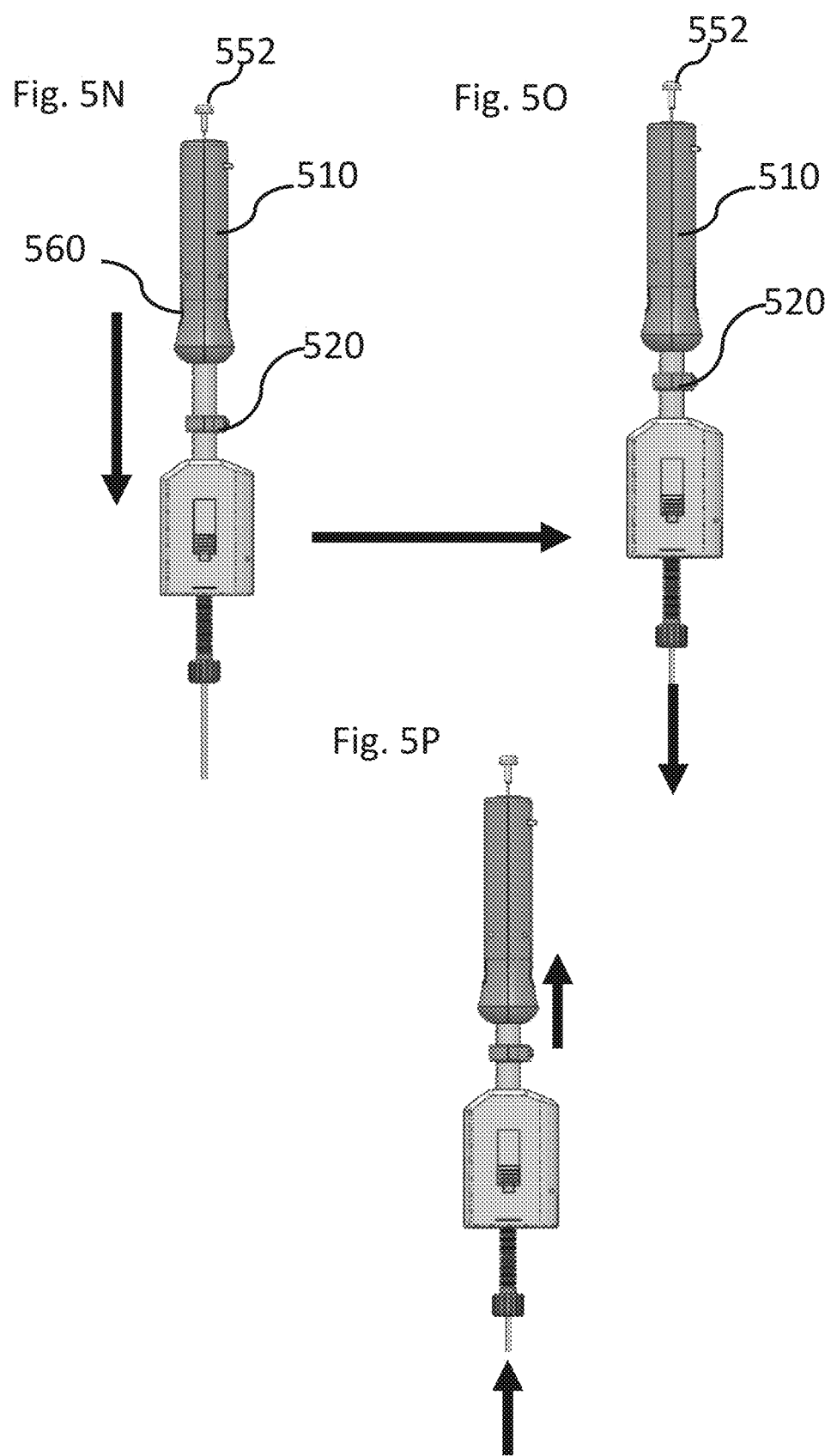

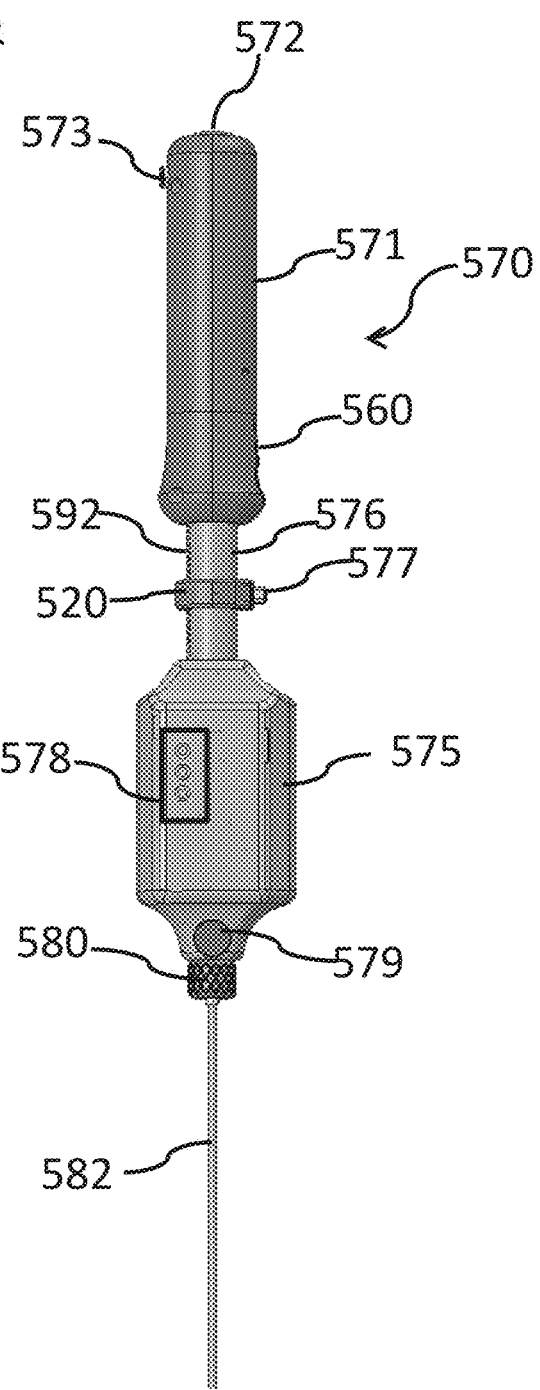

Fig. 8D
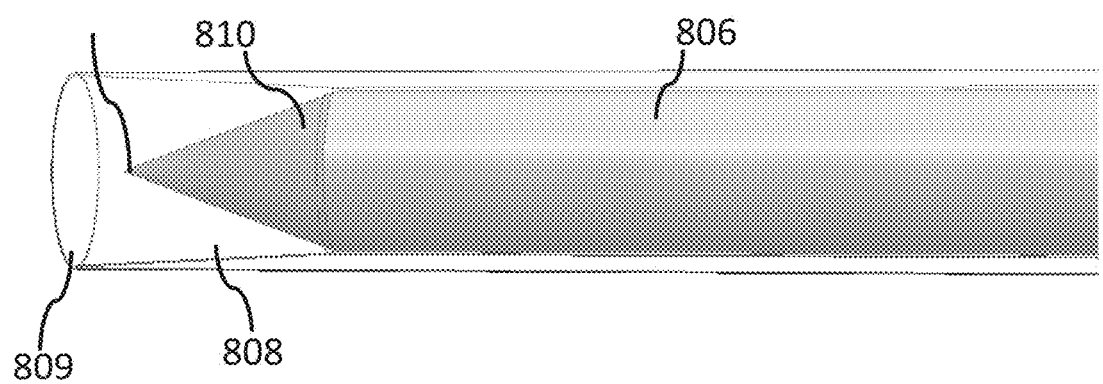
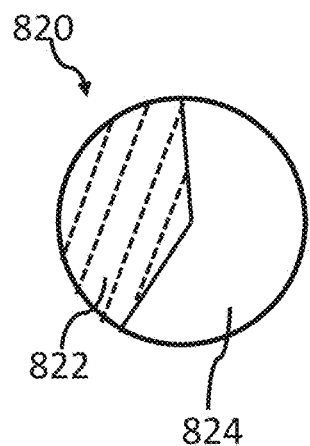
Fig. 8E
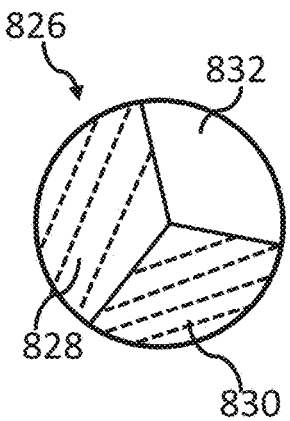
Fig. 8F
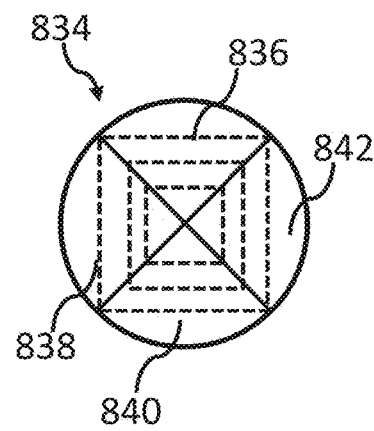
Fig. 8G

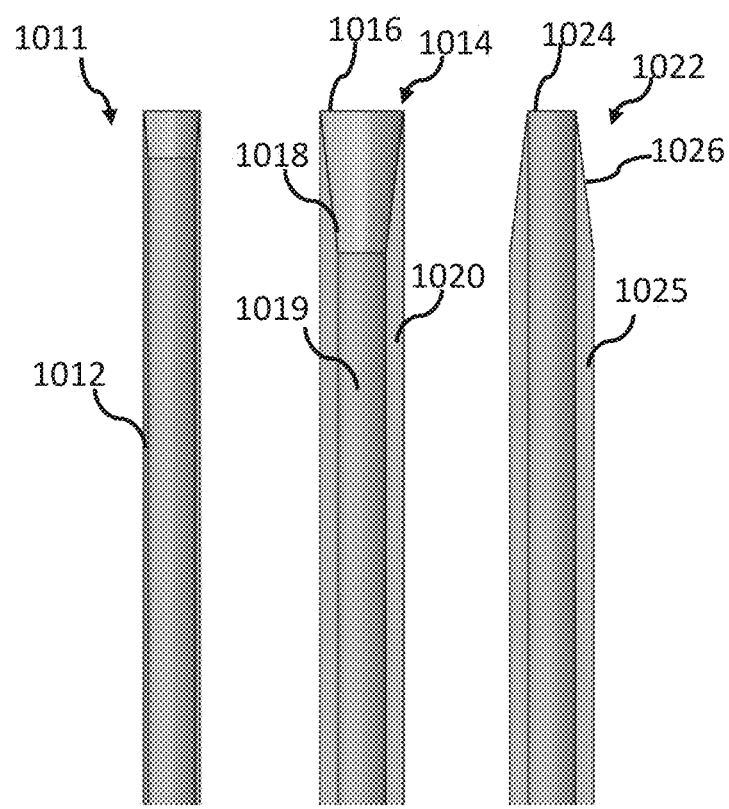

SharkCore™- Medtronic

Acquire™- Boston

Embodiment- LIMACA

Fig. 17A
Fig. 17B
1602
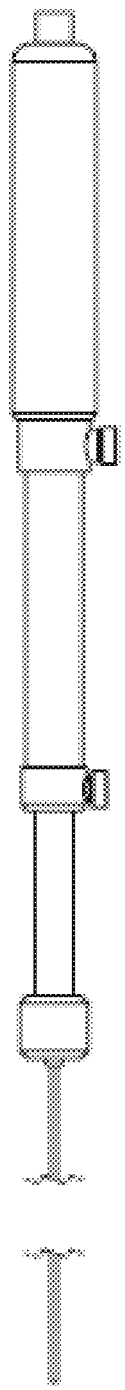
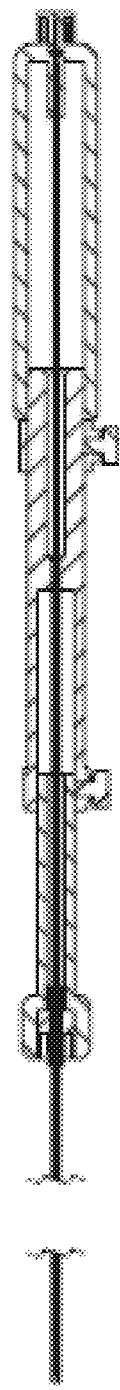

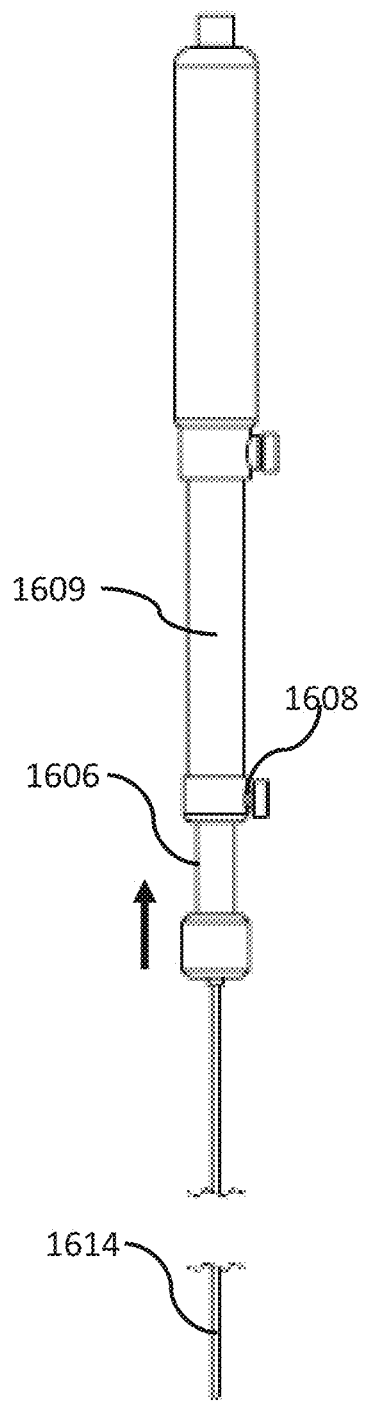
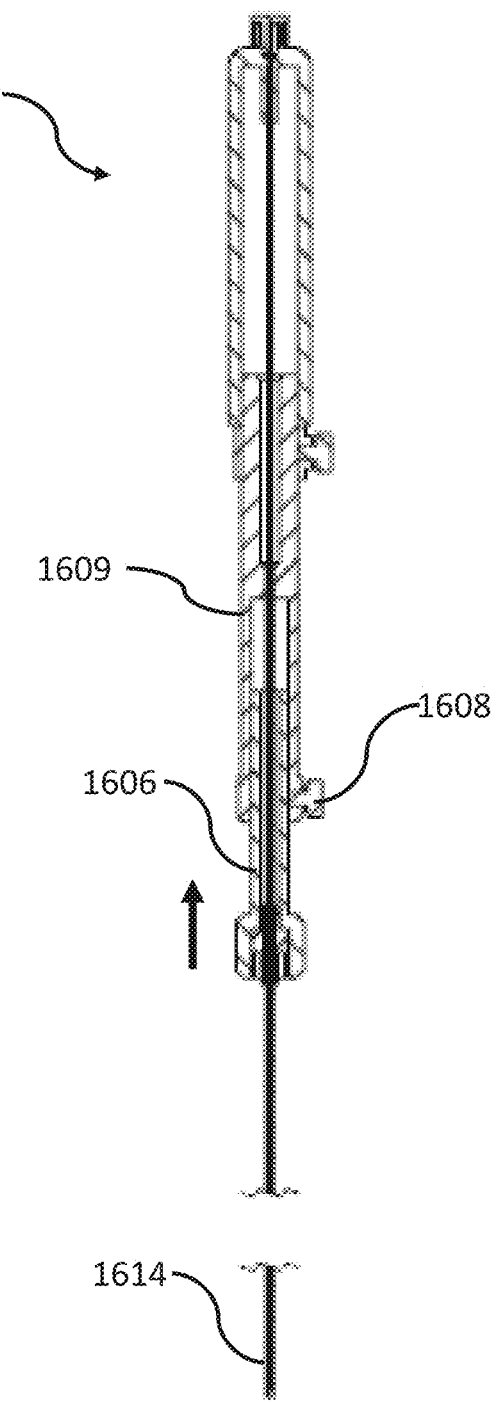
Fig. 17C
Fig. 17D

Fig. 17E
Fig. 17F
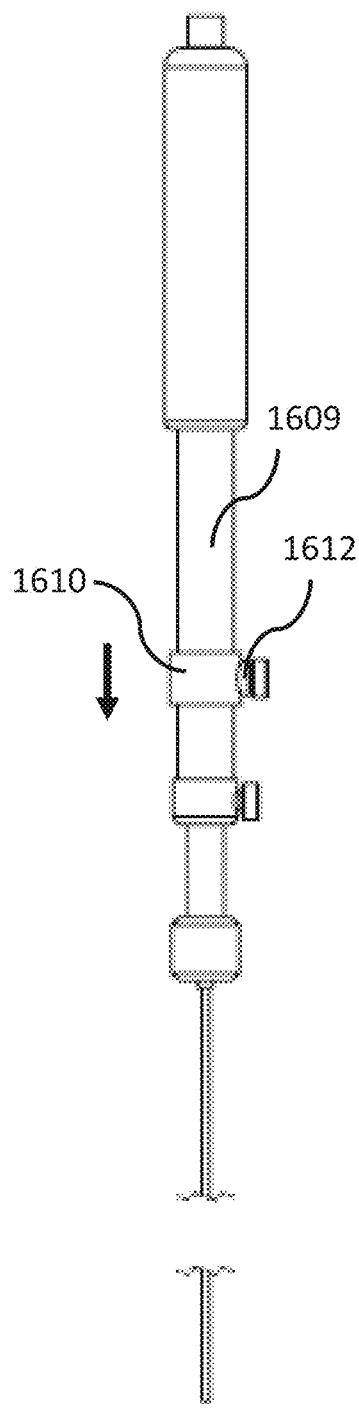
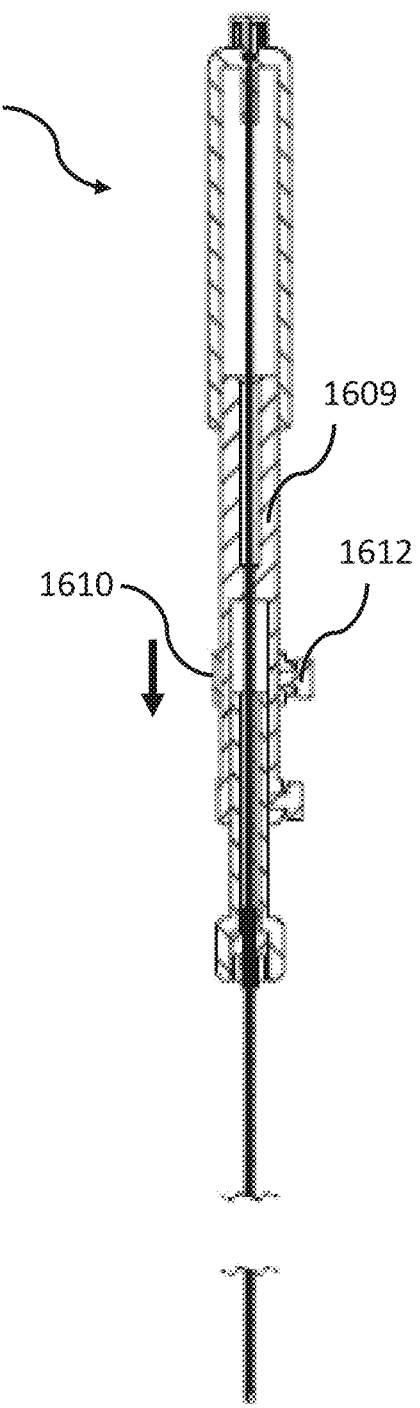

Fig. 17I
Fig. 17J
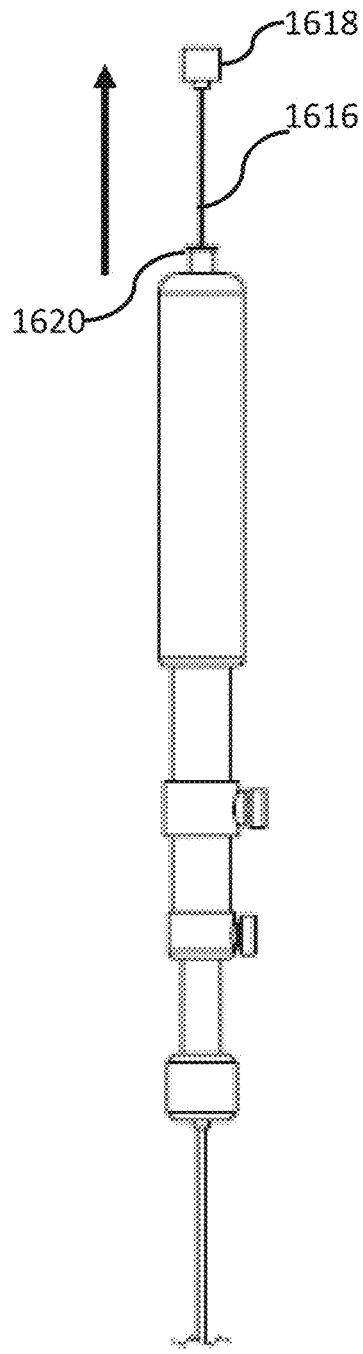
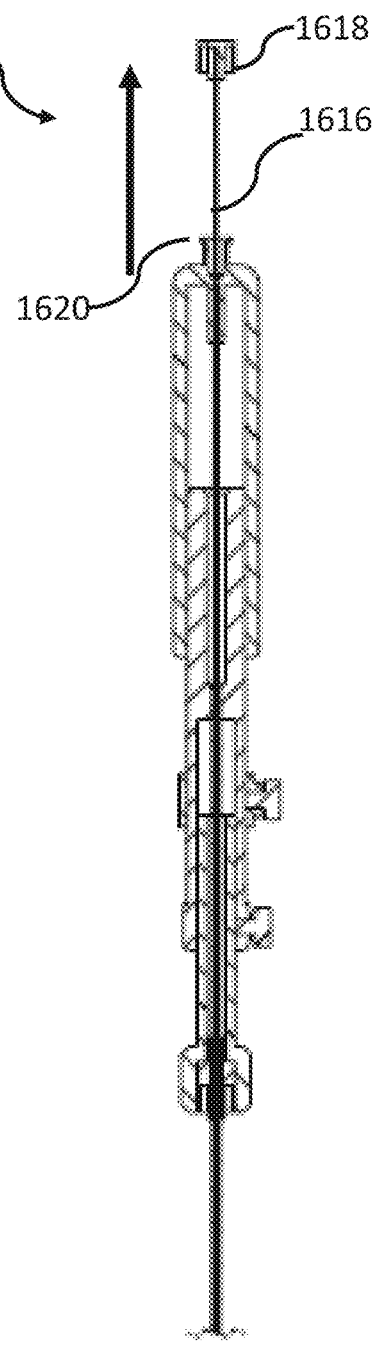

Fig. 17K
Fig. 17L
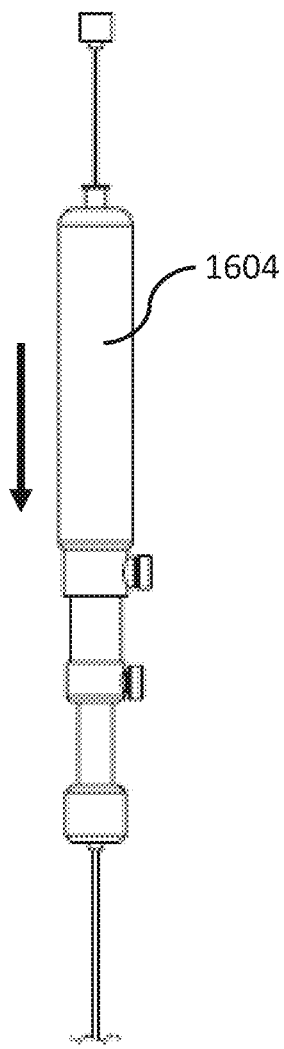
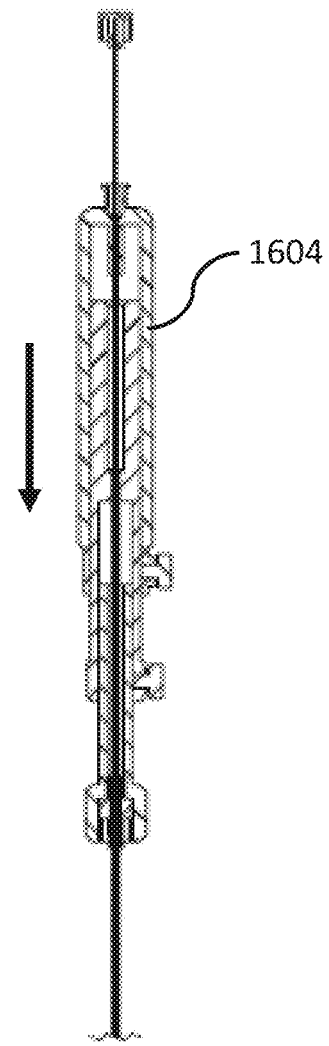
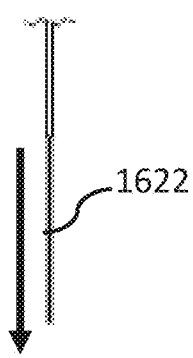
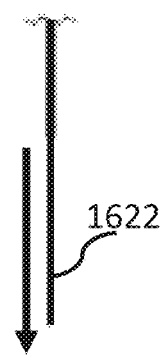

BIOPSY DEVICE

RELATED APPLICATIONS

This application is a National Phase of PCT Patent Application No. PCT/IL2019/050156 having International filing date of Feb. 7, 2019, which claims the benefit of priority under 35 USC § 119(e) of U.S. Provisional Patent Application No. 62/627,786 filed on Feb. 8, 2018, U.S. Provisional Patent Application No. 62/722,907 filed on Aug. 26, 2018, and U.S. Provisional Patent Application No. 62/787,783 filed on Jan. 3, 2019. The contents of the above applications are all incorporated by reference as if fully set forth herein in their entirety.

FIELD AND BACKGROUND OF THE INVENTION

The present invention, in some embodiments thereof, relates to a biopsy device and, more particularly, but not exclusively, to a soft tissue biopsy device.
Biopsy devices with a rotating sampling element are used to sample hard tissues, for example bone. Other biopsy devices use a sampling element for sampling soft tissue, for example biopsies of dermal tissue.

U.S. Pat. No. 8,685,635 B2 describes "embodiments of the present invention provide Dermal Micro-organs (DMOs), methods and apparatuses for producing the same. Some embodiments of the invention provide a DMO including a plurality of dermal components, which substantially retain the micro-architecture and three dimensional structure of the dermal tissue from which they are derived, having dimensions selected so as to allow passive diffusion of adequate nutrients and gases to cells of the DMO and diffusion of cellular waste out of the cells so as to minimize cellular toxicity and concomitant death due to insufficient nutrition and accumulation of waste in the DMO. Some embodiments of the invention provide methods and apparatuses for harvesting the DMO. An apparatus for harvesting the DMO may include, according to some exemplary embodiments, a support configuration to support a skin-related tissue structure from which the DMO is to be harvested, and a cutting tool able to separate the DMO from the skin-related tissue structure. Other embodiments are described and claimed".

SUMMARY OF THE INVENTION

Some examples of some embodiments of the invention are listed below:

Example 1. A soft tissue biopsy device comprising:
an elongated handle comprising a gripping member;
an elongated flexible shaft mechanically comprising a hollow distal sampling portion with an internal lumen and a distal opening facing a soft tissue;
a driving unit configured to rotate said sampling portion with a speed in a range of 100 rounds-per-minute (RPM) to 10,000 RPM while said sampling portion axially advances into said soft tissue.

Example 2. The biopsy device according to example 1, wherein said sampling portion comprises a cutting edge surrounding said distal opening with an external and/or an internal circumferential tapered region, wherein said cutting edge is shaped and sized for cutting said soft tissue.

Example 3. The biopsy device according to any one of examples 1 or 2, wherein said driving unit comprises a gear motor configured to rotate and axially advance said sampling portion according to a selected ratio between rotation velocity and axial advancement velocity.

Example 4. The biopsy device according to example 3, wherein said ratio is pre-determined according to tissue type and/or tissue properties.

Example 5. The biopsy device according to any one of the previous examples, wherein said sampling portion comprises at least one internal protrusion and/or bulge connected to an internal surface surrounding said internal lumen of said sampling portion.

Example 6. The biopsy device according to any one of the previous examples, wherein said sampling portion comprises at least one internal threading at least partly surrounding said internal lumen of said sampling portion.

Example 7. The biopsy device according to any one of the previous examples, wherein said sampling portion comprises at least one helical protrusion at least partly surrounding said internal lumen of said sampling portion.

Example 8. The biopsy device according to any one of the previous examples, wherein an internal diameter of said sampling portion at a distance of at least 2 mm from said distal opening is smaller than a diameter of said distal opening.

Example 9. The biopsy device according to any one of the previous examples, wherein an internal diameter of said sampling section at a distance of at least 2 mm from said distal opening is wider than a diameter of said distal opening.

Example 10. The biopsy device according to any one of examples 8 or 9, wherein said distal opening diameter is in a range of 0.3 mm to 5 mm.

Example 11. The biopsy device according to any one of the previous examples, wherein said sampling portion is a replaceable needle.

Example 12. The biopsy device according to example 11, wherein a gauge value of said replaceable needle is in a range of 18-25 gauge.

Example 13. The biopsy device according to any one of the previous examples, wherein said shaft comprises a braided torque coil.

Example 14. The biopsy device according to any one of the previous examples, comprising a stylet shaped and sized to be advanced forward and to be retracted within said internal lumen of said shaft.

Example 15. A soft tissue biopsy device, comprising:
an elongated flexible shaft having a hollow sampling portion at a distal end of said elongated shaft having a distal opening facing said soft tissue, wherein said hollow sampling portion is shaped and sized for engaging said soft tissue with friction forces, and for separating a tissue sample from said soft tissue with shearing and/or tensile forces.

Example 16. The device according to example 15, wherein said sampling portion comprises a cutting edge surrounding a distal opening of said sampling portion with an external and/or an internal circumferential tapered surface.

Example 17. The device according to example 15, wherein said sampling portion comprises a serrated cutting edge.

Example 18. The device according to any one of examples 15 to 17, wherein said sampling portion comprises at least one short protrusion and/or bulge connected to the internal surface of said sampling portion.

Example 19. The device according to any one of examples 15 to 17, wherein said sampling portion comprises at least one arc-shaped protrusion connected to the internal surface of the sampling portion, wherein said arc-shaped protrusion at least partly surrounds an internal lumen of said sampling portion.

Example 20. The device according to any one of examples 15 to 19, wherein said sampling portion comprises an internal threading and/or at least one notch on an internal surface of said sampling portion.

Example 21. The device according to any one of examples 15 to 20, wherein an internal diameter of said sampling portion located at least 2 mm from said distal opening is smaller than a diameter of said sampling portion opening.

Example 22. The device according to any one of examples 15 to 20, wherein an internal diameter of said sampling portion located at least 2 mm from said distal opening is larger than a diameter of said sampling portion opening.

Example 23. The device according to any one of examples 15 to 22, wherein an outer diameter of said sampling portion is in a range of 0.5-4 mm.

Example 24. The device according to any one of examples 21 or 22, wherein said distal opening diameter is in a range of 0.3-1 mm.

Example 25. The device according to any one of examples 15 to 24, wherein said sampling portion comprises a needle.

Example 26. The device according to example 25, wherein a gauge value of said needle is in a range of 18-25 gauge.

Example 27. A method for sampling soft tissue, comprising:
rotating a sampling portion of a flexible shaft, wherein said flexible shaft is at least partly hollow; axially advancing said sampling portion during said rotating into said soft tissue.

Example 28. The method according to example 27, comprising:
adjusting rotation speed and/or axial advancement velocity of said sampling portion according to a type of said soft tissue.

Example 29. The method according to example 28, wherein said adjusting comprises adjusting rotation speed and/or axial advancement velocity of said sampling portion according to properties of said soft tissue.

Example 30. The method according to example 29, wherein said soft tissue properties comprise tissue composition, tissue size and/or tissue density.

Example 31. The method according to example 27, comprising selecting a biopsy device having a driving unit with a fixed ratio between rotation speed and axial advancement velocity prior to said rotating.

Example 32. The method according to any one of examples 27 to 31, wherein said rotating comprises rotating said sampling portion with a rotation speed in a range of 100 RPM to 10,000 RPM.

Example 33. The method according to any one of examples 27 to 32, wherein said axially advancing comprises axially advancing said sampling portion with an axial advancement velocity in a range of 0.4 mm/sec to 50 mm/sec.

Example 34. The method according to any one of examples 27 to 33, comprising separating a tissue sample from said soft tissue, wherein said tissue sample is positioned within a lumen of said sampling portion.

Example 35. The method according to example 34, comprising applying suction force within said lumen of said sampling portion sufficient to hold said tissue sample within said lumen.

Example 36. The method according to any one of examples 34 or 35, comprising extracting said tissue sample from said lumen.

Example 37. The method according to example 36, wherein said extracting comprises advancing a stylet within said lumen to contact release said tissue sample.

Example 38. The method according to example 36, wherein said extracting comprises applying fluids within said lumen to release said tissue sample.

Example 39. The method according to example 36, wherein said extraction comprises applying suction forces within said lumen to release and attract said tissue sample.

Example 40. The method according to any one of examples 27 to 39 comprising retracting said sampling portion from said soft tissue.

Example 41. The method according to example 40, wherein said retracting comprises retracting said sampling portion from said soft tissue while said rotating is stopped.

Following are some additional examples of some embodiments of the invention:

Example 1. A soft tissue biopsy device comprising:
an elongated handle comprising a gripping member;
an elongated flexible shaft mechanically comprising a hollow distal sampling portion with an internal lumen and a distal opening facing a soft tissue;
a driving unit configured to rotate said sampling portion with a speed in a range of 100 rounds-per-minute (RPM) to 10,000 RPM while said sampling portion axially advances into said soft tissue.

Example 2. The biopsy device according to example 1, wherein said sampling portion comprises a cutting edge surrounding said distal opening with an external and/or an internal circumferential tapered region, wherein said cutting edge is shaped and sized for cutting said soft tissue.

Example 3. The biopsy device according to any one of examples 1 or 2, wherein said driving unit comprises a gear motor configured to rotate and axially advance said sampling portion according to a selected ratio between rotation velocity and axial advancement velocity.

Example 4. The biopsy device according to example 3, wherein said ratio is pre-determined according to tissue type and/or tissue properties.

Example 5. The biopsy device according to any one of the previous examples, wherein said sampling portion comprises at least one internal protrusion and/or bulge connected to an internal surface surrounding said internal lumen of said sampling portion.

Example 6. The biopsy device according to any one of the previous examples, wherein said sampling portion comprises at least one internal threading at least partly surrounding said internal lumen of said sampling portion.

Example 7. The biopsy device according to any one of the previous examples, wherein said sampling portion comprises at least one helical protrusion at least partly surrounding said internal lumen of said sampling portion.

Example 8. The biopsy device according to any one of the previous examples, wherein an internal diameter of said sampling portion at a distance of at least 1 mm from said distal opening is smaller than a diameter of said distal opening.

Example 9. The biopsy device according to any one of examples 1 to 7, wherein an internal diameter of said sampling section at a distance of at least 1 mm from said distal opening is wider than a diameter of said distal opening.

Example 10. The biopsy device according to any one of examples 8 or 9, wherein said distal opening diameter is in a range of 0.3 mm to 5 mm.

Example 11. The biopsy device according to any one of the previous examples, wherein said sampling portion is a replaceable needle.

Example 12. The biopsy device according to any one of the previous examples, wherein a gauge value of said sampling portion is in a range of 16-25 gauge.

Example 13. The biopsy device according to any one of the previous examples, wherein said shaft comprises a torque coil formed from at least one wire.

Example 14. The biopsy device according to example 13, wherein said sampling portion is formed by said at least one wire.

Example 15. The biopsy device of example 14, wherein a thickness of a wall of said sampling portion is at least 0.04 mm.

Example 16. The biopsy device according to any one of the previous examples, comprising a stylet shaped and sized to be advanced forward and to be retracted within said internal lumen of said shaft.

Example 17. The biopsy device according to example 16, comprising a stylet release button, wherein said stylet release button is configured to release said stylet from a distal position to a proximal position.

Example 18. The biopsy device according to any one of examples 16 or 17, wherein a cross-section of at least a portion of said stylet is an asymmetrical cross-section.

Example 19. The biopsy device according to any one of examples 16 or 17, wherein a cross-section of at least a portion of said stylet is a non-circular cross-section.

Example 20. The biopsy device according to any one of the previous examples, wherein an external surface of said sampling portion is at least partly covered with a sealing tubing, wherein said sealing tubing prevents the release of a tissue sample and/or liquids within said sampling portion through a wall of said sampling portion.

Example 21. The biopsy device according to any one of the previous examples, wherein an external surface of said sampling portion is at least partly covered by a low-friction layer configured to reduce friction with surrounding tissue during the movement of the sampling portion.

Example 22. The biopsy device according to any one of the previous examples, wherein at least part of an external surface of said elongated flexible shaft comprises one or more axially and circumferential spaced-apart grooves and/or indentations shaped and sized to reflect ultrasonic waves in different directions.

Example 23. The biopsy device according to any one of the previous examples, wherein said driving unit rotates said sampling portion intermittently in rotation pulses.

Example 24. The biopsy device according to any one of the previous examples, wherein said driving unit rotates said sampling portion in a variable rotation speed.

Example 25. The biopsy device according to any one of the previous examples, wherein said driving unit rotates said sampling portion at opposite directions.

Example 26. The biopsy device according to any one of the previous examples, wherein said driving unit rotates said sampling portion at a rotation angle smaller than 360° degrees.

Example 27. A soft tissue biopsy device, comprising:
an elongated handle comprising a gripping member;
an elongated flexible shaft mechanically comprising a hollow distal sampling portion with an internal lumen and a distal opening facing a soft tissue;
at least one preloaded energy source configured to rotate said sampling portion with a speed in a range of 100 rounds-per-minute (RPM) to 10,000 RPM while said sampling portion axially advances into said soft tissue.

Example 28. A soft tissue biopsy device according to example 27, wherein said at least one preloaded energy source comprises a spring and/or a flywheel.

Example 29. A soft tissue biopsy device according to any one of examples 27 or 28, wherein said at least one preloaded energy source is a replaceable energy source.

Example 30. A soft tissue biopsy device, comprising:
an elongated handle comprising a gripping member;
an elongated flexible shaft mechanically comprising a hollow distal sampling portion with an internal lumen and a distal opening facing a soft tissue;
a movable stylet travelling between said sampling portion and said handle through said elongated flexible shaft, wherein said stylet moves between a distal position in which said stylet at least partly occupies a lumen of said sampling portion, and a proximal position in which said stylet is retracted from said lumen of said sampling portion;
a stylet locker positioned in said handle, wherein said stylet locker locks said stylet in a distal position when said elongated flexible shaft is navigated towards a selected sampling site.

Example 31. A soft tissue biopsy device according to example 30, comprising:
a stylet release button connected to said stylet locker, wherein said stylet release button is configured to release said stylet from said distal position prior to penetration of said sampling portion into a tissue.

Example 32. A soft tissue biopsy device according to example 31, comprising at least one spring connected to said stylet, wherein said spring pushes said stylet to said proximal position by retracting said stylet from said distal position to a selected retraction distance.

Example 33. A soft tissue biopsy device according to claim 32, wherein said retraction distance is predetermined.

Example 34. A soft tissue biopsy device according to example 32, wherein said retraction distance is adjusted according to one or more of tissue type, desired number of tissue samples and/or desired tissue sample volume.

Example 35. A soft tissue biopsy device according to any one of examples 30 to 33, comprising at least one sensor configured to sense a location of said stylet.

Example 36. A soft tissue biopsy device according to any one of examples 30 to 35, wherein a cross-section of at least a portion of said movable stylet is an asymmetrical cross-section.

Example 37. A soft tissue biopsy device according to any one of examples 30 to 36, wherein a cross-section of at least a portion of said movable stylet is a non-circular cross-section.

Example 38. A soft tissue biopsy device, comprising:
an elongated flexible shaft having a hollow sampling portion at a distal end of said elongated shaft having a distal opening facing said soft tissue, wherein said hollow sampling portion is shaped and sized for engaging said soft tissue with friction forces, and for separating a tissue sample from said soft tissue with shearing and/or tensile forces.

Example 39. The device according to example 38, wherein said sampling portion comprises a cutting edge surrounding a distal opening of said sampling portion with an external and/or an internal circumferential tapered surface.

Example 40. The device according to example 38, wherein said sampling portion comprises a serrated cutting edge.

Example 41. The device according to any one of examples 38 to 40, wherein said sampling portion comprises at least one short protrusion and/or bulge connected to the internal surface of said sampling portion.

Example 42. The device according to any one of examples 38 to 40, wherein said sampling portion comprises at least one arc-shaped protrusion connected to the internal surface of the sampling portion, wherein said arc-shaped protrusion at least partly surrounds an internal lumen of said sampling portion.

Example 43. The device according to any one of examples 38 to 42, wherein said sampling portion comprises an internal threading and/or at least one notch on an internal surface of said sampling portion.

Example 44. The device according to any one of examples 38 to 43, wherein an internal diameter of said sampling portion located at least 1 mm from said distal opening is smaller than a diameter of said sampling portion opening.

Example 45. The device according to any one of examples 38 to 43, wherein an internal diameter of said sampling portion located at least 1 mm from said distal opening is larger than a diameter of said sampling portion opening.

Example 46. The device according to any one of examples 38 to 45, wherein an outer diameter of said sampling portion is in a range of 0.5-4 mm.

Example 47. The device according to any one of examples 44 or 45, wherein said distal opening diameter is in a range of 0.3-1 mm.

Example 48. The device according to any one of examples 38 to 47, wherein said sampling portion comprises a needle.

Example 49. The device according to example 48, wherein a gauge value of said needle is in a range of 18-25 gauge.

Example 50. A biopsy needle, comprising:
 a flexible tube having an inner lumen, a proximal end and a distal end, wherein said distal end is shaped and sized to penetrate into a tissue;
 wherein walls of said tube are formed by twisting at least one wire around said inner lumen.

Example 51. A biopsy needle according to example 50, wherein an outer surface of said tube comprises at least one continuous groove axially and rotationally displaced on said surface along a longitudinal axis of said biopsy needle.

Example 52. A biopsy needle according to example 50, wherein an outer surface of said tube comprises at least one helical groove extending along a longitudinal axis of said biopsy device.

Example 53. A biopsy needle according to any one of examples 50 to 52, wherein an outer surface of said tube comprises a plurality of axially and circumferential spaced-apart indentations.

Example 54. A method for sampling soft tissue, comprising:
 rotating a sampling portion of a flexible shaft, wherein said flexible shaft is at least partly hollow;
 axially advancing said sampling portion during said rotating into said soft tissue.

Example 55. The method according to example 54, comprising: adjusting rotation speed and/or axial advancement velocity of said sampling portion according to a type of said soft tissue.

Example 56. The method according to example 55, wherein said adjusting comprises adjusting rotation speed and/or axial advancement velocity of said sampling portion according to properties of said soft tissue.

Example 57. The method according to example 56, wherein said soft tissue properties comprise tissue composition, tissue size and/or tissue density.

Example 58. The method according to example 54, comprising selecting a biopsy device having a driving unit with a fixed ratio between rotation speed and axial advancement velocity prior to said rotating.

Example 59. The method according to any one of examples 54 to 58, wherein said rotating comprises rotating said sampling portion with a rotation speed in a range of 100 RPM to 10,000 RPM.

Example 60. The method according to any one of examples 54 to 58, wherein said axially advancing comprises axially advancing said sampling portion with an axial advancement velocity in a range of 0.4 mm/sec to 50 mm/sec.

Example 61. The method according to any one of examples 54 to 60, comprising separating a tissue sample from said soft tissue, wherein said tissue sample is positioned within a lumen of said sampling portion.

Example 62. The method according to example 61, comprising applying suction force within said lumen of said sampling portion sufficient to hold said tissue sample within said lumen.

Example 63. The method according to any one of examples 61 or 62, comprising extracting said tissue sample from said lumen.

Example 64. The method according to example 63, wherein said extracting comprises advancing a stylet within said lumen to contact release said tissue sample.

Example 65. The method according to example 63, wherein said extracting comprises applying fluids within said lumen to release said tissue sample.

Example 66. The method according to example 63, wherein said extraction comprises applying suction forces within said lumen to release and attract said tissue sample.

Example 67. The method according to any one of examples 54 to 66 comprising retracting said sampling portion from said soft tissue.

Example 68. The method according to example 67, wherein said retracting comprises retracting said sampling portion from said soft tissue while said rotating is stopped.

Example 69. The method according to any one of examples 54 to 68, wherein said rotating comprises rotating said sampling portion at an angle smaller than 360 degrees.

Example 70. The method according to any one of examples 54 to 69, wherein said rotating comprises rotating said sampling portion at a first direction and in an opposite direction.

Example 71. The method according to any one of examples 54 to 70, wherein said rotating comprises rotating said sampling portion intermittently in a train of two or more rotation pulses.

Example 72. The method according to example 71, wherein said two or more rotation pulses are at rotation pulses at two opposite directions.

Example 73. The method according to any one of examples 71 or 72, wherein said two or more rotation pulses have varying rotation angles and/or rotation duration.

Example 74. A soft tissue biopsy device, comprising:
 an elongated handle comprising a gripping member;
 an elongated flexible shaft mechanically connected to said elongated handle, comprising a hollow distal sampling portion with an internal lumen and a distal opening facing a soft tissue, wherein walls of said hollow distal sampling portion are formed by twisting at least one wire around said internal lumen.

Example 75. A device according to example 74, wherein an external surface of said hollow distal sampling portion is covered at least partly by a low-friction layer configured to reduce friction with tissue surrounding said sampling portion during movement of said sampling portion.

Example 76. A device according to example 75, wherein said low-friction layer comprises a coating, a tube or a shrink tube.

Example 77. A device according to any one of examples 75 or 76, wherein said low-friction layer comprises one or more of Polytetrafluoroethylene (PTFE), High-density polyethylene (HDPE), PARYLENE.

Example 78. A device according to any one of examples 75 to 77, wherein said low-friction layer is an isolating layer, comprises to isolate said walls of said sampling portion from passage of liquids and/or tissue.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and figures. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3C and 3D are graphs demonstrating rotation types of a sampling portion of a biopsy device, according to some embodiments of the invention;

FIGS. 8B-8D are schematic illustrations of a stylet within a shaft of a biopsy device, according to some embodiments of the invention;

FIGS. 8E-8G are schematic upper view illustrations of a distal end of a stylet having at least one flat surface, according to some embodiments of the invention;

FIGS. 10A-10E are schematic illustrations of a sampling portion assembly, according to some embodiments of the invention;

FIGS. 17A-17L are schematic illustrations of a biopsy guide during a tissue sampling process, according to some embodiments of the invention.

DESCRIPTION OF SPECIFIC EMBODIMENTS OF THE INVENTION

Figure 1A:
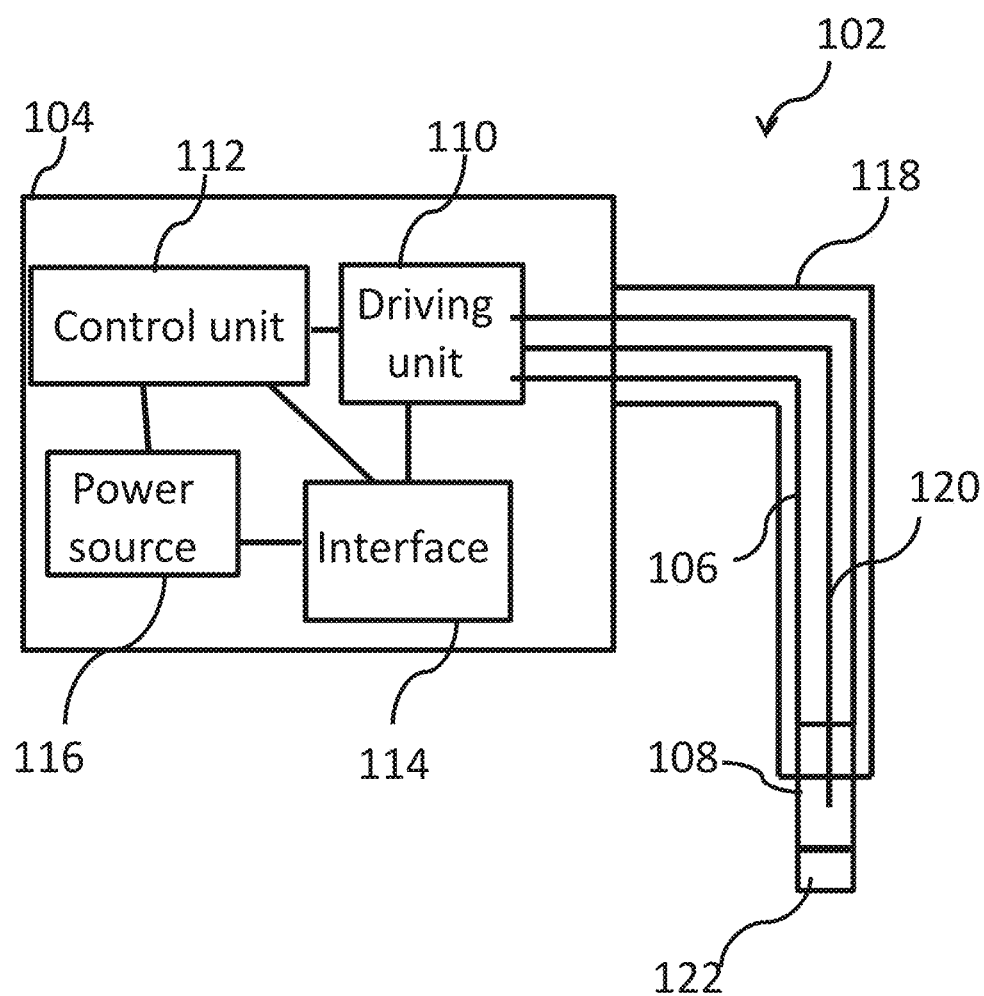
FIG. 1A is a block diagram of a biopsy device, according to some embodiments of the invention.

The present invention, in some embodiments thereof, relates to a biopsy device and, more particularly, but not exclusively, to a soft tissue biopsy device.

An aspect of some embodiments relates to sampling a target tissue by application of separating forces to separate a tissue sample from the target tissue. In some embodiments, the separating forces comprise one or more of shearing forces, tearing forces, and/or tensile forces. In some embodiments, the forces applied on the target tissue are larger than the tensile strength of the tissue, optionally causing separation of a tissue sample from the target tissue. In some embodiments, a sampling portion of a flexible shaft comprises a cutting edge on the inner surface of the distal end of the shaft for cutting the tissue during the movement of the shaft. In some embodiments, the inner surface of the sampling portion lumen applies friction forces on a tissue sample positioned inside the shaft that cause, for example separating the tissue sample from the target tissue. In some embodiments, rotation while axially advancement of the sampling portion into the target tissue, applies shearing forces and/or tensile forces on a tissue sample located at least partly inside the hollow shaft lumen, optionally causing the separation of the tissue sample from the target tissue.

According to some exemplary embodiments, the target tissue is sampled by a fast rotating sampling portion of a flexible shaft. In some embodiments, the shaft rotates in a speed of at least 100 rounds-per-minute (RPM). Optionally, the shaft rotates while axially advancing into the target tissue. In some embodiments, a sampling portion at a distal section of the shaft, for example a section of the shaft closer to the target tissue, rotates in a speed of at least 300 rounds-per-minute (RPM). Optionally, the sampling portion is a needle. In some embodiments, the needle is an 18-25G needle, for example 18G, 19G, 22G, 25G or any intermediate, smaller or larger value.

According to some embodiments, a ratio between the axially advancement velocity of the shaft and the shaft rotation speed is fixed, optionally according to the target tissue type and/or target tissue properties. In some embodiments, the target tissue properties comprise target tissue composition, target tissue density and/or target tissue size. Alternatively or additionally, the ratio is determined according to the presence or location of blood vessels and/or nerves in the vicinity of the target tissue. In some embodiments, the ratio is determined, for example to allow efficient cutting of the target tissue without causing damage to surrounding tissue, for example damage due to tissue warm-up and/or compression. In some embodiments, a user selects a biopsy device model or type with a desired and/or pre-determined ratio per a specific target tissue. Alternatively, the ratio between rotation velocity and axial advancement velocity is selected, optionally based on the tissue type and/or tissue properties. In some embodiments, the ratio is selected by a user. Alternatively, the ratio is automatically selected by a control circuitry of the biopsy device, optionally according to at least one table, and/or at least one algorithm stored in a memory of the biopsy device. In some embodiments, the user selects independently the rotation velocity and the axial advancement velocity, optionally to be in a desired ratio or range of ratios.

According to some embodiments, the shaft rotation speed is adjusted to a desired axial advancement velocity, optionally according to tissue type. Alternatively or additionally, the axial advancement velocity is adjusted according to a desired rotation speed. Alternatively, the rotational velocity and the axial speed are determined separately.

According to some embodiments, at least part of the internal surface of the hollow shaft distal section is shaped to prevent the release of a tissue sample from the hollow shaft lumen optionally by mechanically interfering with the tissue sample. In some embodiments, the internal surface of the hollow shaft distal section comprises at least one bulge and/or at least one protrusion that mechanically interact with a tissue sample inside the hollow shaft. Optionally, the at least one protrusion is a spiral protrusion which at least partly surrounds the inner surface of the hollow shaft distal section. Alternatively or additionally, an internal diameter of a more proximal section of the hollow shaft is larger than an internal diameter of a distal section closer to the body tissue, for example to interfere with the release of the tissue sample from the hollow shaft.

According to some embodiments, two or more separate tissue samples are sampled in a single puncturing of the target tissue. In some embodiments, modifying a sampling portion rotation and/or axial advancement allow, for example, to sample the two or more tissue samples. Additionally and/or alternatively, a shape of the sampling portion for example internal and/or external surfaces of the sampling portion allow, for example to sample the two or more tissue samples.

An aspect of some embodiments relates to sampling a tissue by a rotating and axially advancing sampling portion of a biopsy device, for example a needle. In some embodiments, a ratio between the rotation speed and the axial advancement velocity of the sampling portion is fixed. Alternatively, the rotation speed and/or the axial advancement velocity are adjusted, optionally according to tissue type and/or tissue properties. In some embodiments, the sampling portion axially advances into a target tissue without rotation.

According to some embodiments, the ratio and/or the adjustment of the rotation speed and/or axial advancement velocity are determined according to tissue location, a desired penetration depth and/or a desired sample volume. In some embodiments, the maximal penetration depth into the target tissue is limited, for example to prevent damage to surrounding tissue, for example blood vessels or nerves. Alternatively or additionally, the maximal penetration depth is limited, for example to prevent sampling of undesired tissue and/or to prevent damage to blood vessels and/or nerves within the target tissue.

According to some embodiments, the tissue sampling location is selected by navigating a sampling portion at the distal end of an elongated shaft to a desired sampling location. In some embodiments, additional tissue samples are isolated by navigating the sampling portion to a different tissue sampling location. Alternatively or additionally, the sampling portion is elevated to a maximal elevation angle of 50 degrees, for example 40 degrees, 30 degrees, 20 degrees or any intermediate, lower or higher elevation angle, to reach a desired sampling location. Optionally, the sampling portion is elevated by elevation of an endoscope where the sampling portion is positioned and/or elevation of a sleeve, also termed herein as sheath, surrounding the sampling portion.

According to some embodiments, the sampling portion, for example a needle has a beveled edge. In some embodiments, the needle comprises a plurality of segments. In some embodiments, the sampling portion comprises a coiled coil, a braided coil or any other coil formed by twisting or interweaving a plurality of wires. In some embodiments, the sampling portion is hollow, for example to allow insertion of a tissue sample into the sampling portion during a tissue sampling procedure. In some embodiments, the needle is formed from Stainless Steel, Nitinol, Cobalt chromium.

A potential advantage of using a segmented needle, for example in the form of a coiled coil needle, a braided needle is that the interfaces between the plurality of segments, the coiled portions of the coil or the braiding may improve the elasticity of the needle and potentially improve the precision of the stabbing, in addition the coiled portions of the coil or the braiding on the outer surface reflect ultrasound waves with higher efficiency compared to a needle having a solid external surface. In some embodiments, a pattern formed on the sampling portion external surface may allow better reflection of ultrasound waves back towards the transmitter. Increasing the ultrasound waves reflection efficiency allows an improved echogenicity and visualization, for example during the tissue sampling process.

Replacing fine needle aspiration (FNA) or fine needle biopsy (FNB) needles in the SharkCore™ system of Medtronic, Acquire™ system of Boston Scientific and/or the ProCore® system of Cook Medical or any other commercial used EUS/FNA needles with the segmented needle, the coiled coil or torque coil with the sampling portion as described herein allows improved echogenicity and improved elasticity of the segmented needle or sampling portion towards a desired tissue, for example to allow tissue sampling by rotation and/or axial stabbing. An aspect of some embodiments relates to gripping a tissue sample within a lumen of a sampling portion of a biopsy device that has a textured or roughed internal surface. In some embodiments, the sampling portion comprises at least one bulge or at least one protrusion, optionally a short protrusion connected to the internal surface. Alternatively or additionally, the internal surface comprises a threading and/or at least one notch. In some embodiments, the threading and/or at least one notch, at least partly surround the inner diameter of the lumen of the sampling portion.

In some embodiments, the textured or roughed internal surface is shaped to increase friction forces between a tissue sample positioned within the lumen of the sampling portion and the internal surface. In some embodiments, the increase in friction forces allows for example better gripping of the tissue sample.

In some embodiments, the at least one bulge and/or at least one protrusion on the internal surface of the sampling portion are shaped to increase the contact area between a tissue sample within the lumen of the sampling portion and the bulge or protrusion. In some embodiments, the increase in contact area allows for example to prevent the exit of the tissue sample from the sampling portion opening.

In some embodiments, the internal lumen of the sampling portion is gradually narrowing when advancing from a distal opening of the sampling portion to more proximal locations within the sampling portion lumen. In some embodiments, the narrowing of the sampling portion lumen compresses the tissue sample within a narrowed space, while applying larger friction forces on the tissue sample, for example to increase the gripping of the tissue sample.

An aspect of some embodiments relates to reducing fatigue failure of a sampling portion of a biopsy device rotating shaft, for example a sampling needle at the distal end of the shaft. In some embodiments, fatigue failure is reduced by controlling shaft movement and/or shaft properties. In some embodiments, the fatigue failure is caused due to relatively hi strain on the rotating shaft. Alternatively or additionally, the fatigue failure is contributed due to heating of the shaft, for example a shaft made from Nitinol, by friction forces and/or cyclic bending of the shaft. In some embodiments, the fatigue failure is caused due to an internal or external surface shape of the shaft.

According to some embodiments, the fatigue failure of a shaft, optionally a Nitinol tube shaft is reduced by reducing friction between a sampling section of the shaft, for example a needle by using a cover, a sleeve or a coating of the needle. Optionally, the outer surface of the needle is lubricated to reduce friction surface between the needle and the surrounding tissue. Optionally, the sleeve is made from a material that increases heat conductivity and reduces heat capacity. Alternatively, in order to reduce the heating of the needle due to the friction and/or bending, a coolant flushing is applied to an internal lumen of the shaft and/or needle, for example saline flushing.

According to some embodiments, the fatigue failure of the shaft is reduced by controlling the rotation and/or axial advancement of the shaft. In some embodiments, a controller of a control unit of the biopsy device limits the continuous rotation of the shaft. In some embodiments, the controller signals a rotor to rotate the shaft during selected time periods, optionally short time periods in a range of 0-1 minute, for example 2 seconds, 10 seconds, 20 seconds, 30 seconds, 40 seconds or any intermediate, smaller or larger value. Alternatively or additionally, the controller signals the motor to rotate the shaft in opposite directions. In some embodiments, the controller stops the rotation of the shaft when reaching a selected number of rotations.

According to some embodiments, a maximal strain value of each needle is determined based on the outer diameter of the needle (OD) and the bending radius (BR), and is calculated using the formula: Maximal strain=OD/2BR. For example, if the OD=0.73 mm, and the bending radius=23 mm, then the calculated maximal strain value is (0.73/2× 23)×100=1.587%. In some embodiments, the controller monitors the rotations of the needle not to exceed a maximal rotation value, for example a maximal rounds value that leads to the calculated maximal cycles in a specific strain on the needle on the specific fatigue characteristic graph/calculation. Optionally, the controller allows rotation in up to 90% of the maximal rotation value, for example 90% maximal rotation value, 80% maximal rotation value, 70% maximal rotation value or any intermediate, smaller or larger maximal rotation value percentage. In some embodiments, the controller monitors a ratio between the needle bending and the number of cycles, for example by measuring changes in electrical current of the motor.

In some embodiments, to reduce fatigue failure, the needle is axially advanced, for example to distribute needle stress and warm-up.

According to some embodiments to reduce the risk of fatigue failure of the needle, the needle is replaced with a hollow torque coil shaft, optionally similar to the proximal section of the shaft but with a smaller diameter, for example to allow lower stress values and optionally better fatigue durability.

According to some embodiments, a thickness of a needle wall is smaller compared to a thickness of a sampling portion made from a hollow torque coil shaft. In some embodiments, a thickness of a needle wall, for example a nitinol needle wall is in a range of 0.05-0.5 mm, for example 0.05-0.2 mm, 0.1-0.4 mm, 0.2-0.5 mm or any intermediate, smaller or larger range of values. In some embodiments, a thickness of a hollow torque coil shaft wall is in a range of 0.1-1 mm, for example 0.1-0.3 mm, 0.2-0.7 mm, 0.5-1 mm or any intermediate, smaller or larger range of values.

According to some embodiments, a hollow torque coil shaft comprises a distal section having a distal opening facing a tissue. In some embodiments, the distal section of the hollow torque coil shaft has an external distal tapered end. Optionally, the external distal tapered end surrounds the distal opening. In some embodiments, the distal opening at the distal tapered end has a diameter that is similar to the diameter of the inner lumen of the hollow shaft.

According to some embodiments, the distal tapered end is formed by external sharpening of the hollow torque coil shaft distal section. Alternatively, a sharpened distal section having an external distal tapered end is connected to a hollow coiled toque shaft, for example by welding.

According to some embodiments, the distal opening of the hollow torque coil shaft has a larger diameter than the diameter of the inner lumen of the hollow shaft formed, for example, by internal sharpening of the hollow shaft lumen. A potential advantage of a hollow torque coil shaft having an opening which is wider than the shaft inner diameter is that it allows to sample a larger tissue sample compared to a hollow shaft with an external distal tapered end. In addition, the narrowing inner lumen condenses the tissue sample as the sample penetrates into the hollow shaft lumen. Optionally, condensing the tissue sample increases friction between the inner surface of the hollow shaft and the sample, allows better separation of the tissue sample from the tissue.

According to some embodiments, an inner surface of the hollow shaft distal section which is shaped and sized for tissue sampling is rugged. Optionally, the inner surface of the hollow shaft distal section comprises a helical texture surrounding the inner lumen of the hollow shaft. A potential advantage of having a rugged and/or textured inner surface is that it increases the friction between the tissue sample and the inner surface, which optionally enables easier cutting of the tissue sample from the tissue as the hollow shaft turns.

According to some embodiments, at least a portion of the hollow torque coil shaft is covered by a tube, for example a shrinkable tube, optionally a heat-shrinkable tube. In some embodiments, the tube seals a portion of the hollow torque coil shaft, for example a distal portion used for tissue sampling, from the external environment. In some embodiments, the tube cover as a thickness in a range of 10-100 μm, for example a thickness in a range of 10-60 μm, 13-50 μm, 30-100 μm or any intermediate, smaller or larger range of values.

An aspect of some embodiments relates to a biopsy needle made from at least one wire twisted to form a tubular structure with an inner lumen. In some embodiments, the inner lumen is shaped and sized to hold a tissue sample. In some embodiments, a distal section of the biopsy needle is externally sharpened to form a tapered end. Optionally, the tapered end is configured to penetrate through a tissue, for example by pushing aside tissue as the biopsy needle is axially advanced into the tissue. Alternatively or additionally, the biopsy needle is internally sharpened for narrowing the inner lumen of the needle. In some embodiments, narrowing the inner lumen of the biopsy needle allows to increase friction forces between a tissue sample within the inner lumen and the inner surface of the biopsy needle. Optionally increasing the friction forces allows easier separation of the tissue sample from the tissue surrounding the biopsy needle.

According to some embodiments, the biopsy needle is a sampling portion of a torque coil of the sampling device. In some embodiments, the torque coil is formed by twisting at least one wire, for example as described above. In some embodiments, the torque coil is externally and/or internally sharpened, for example to allow better penetration of the sampling portion into the tissue and/or better separation of a tissue sample within the sampling portion from the tissue.

According to some embodiments, the external surface of the biopsy needle comprises at least one continuous groove and/or a plurality of indentations axially and radially distributed along a longitudinal axis of the biopsy needle. In some embodiments, for example when the biopsy needle is formed from a sharpened torque coil, the continuous groove and/or plurality of indentations are axially and/or radially distributed along an outer surface of at least a portion of the torque coil. In some embodiments, the at least one continuous groove forms a helical pattern on at least a portion of the external surface of the torque coil and/or biopsy needle.

According to some embodiments, at least a portion of an external surface of the biopsy needle and/or the torque coil is covered by a cover, for example a mesh or a tube, for example a shrinkable tube. In some embodiments, the cover seals gaps and/or voids in the biopsy needle wall, for example to prevent any leakage of tissue sample and/or liquids out from the sampling portion inner lumen. Alternatively or additionally, the cover seals gaps and/or voids in the torque coil, for example a torque coil shaft, to prevent any leakage of tissue sample and/or liquids out from the torque coil inner lumen Optionally, the cover comprises the at least one continuous groove and/or plurality of indentations.

According to some embodiments, the cover, for example a shrinkable cover or a shrinkable tube, seals at least a portion of the torque coil, for example a portion of the torque coil which bends as the torque coil is navigated within the body towards a selected target site. In some embodiments, the cover comprises one or more continuous grooves and/or a plurality of indentations. Optionally, the plurality of indentations is axially and/or circumferentially distributed on the outer surface of the cover. In some embodiments, a pattern formed by said one or more continuous grooves and/or the plurality of indentations is configured to increase the echogenicity of the cover.

An aspect of some embodiments relates to a sampling portion, for example a biopsy needle having at least a portion of an external surface with at least one continuous groove axially and circumferentially displaced along a longitudinal axis of the biopsy needle. In some embodiments, the at least one continuous groove forms at least a partial helical pattern surrounding the biopsy needle. In some embodiments, the at least one continuous groove is formed by twisting at least one wire to form a torque coil, for example a transmission torque coil. Additionally or alternatively, at least a portion of the external surface comprises a plurality of indentations and/or grooves axially and radially spaced apart. In some embodiments, the pattern on the external surface of the sampling portion and/or the torque col is shaped and sized to improve echogenicity of the sampling portion and/or the torque coil respectively.

According to some embodiments, the at least one groove and/or the plurality of indentations form a pattern on the outer surface of the sampling portion and/or the torque coil. In some embodiments, the pattern reflects ultrasound waves in different angular directions, for example to improve the echogenicity of the needle. Alternatively or additionally, the pattern reflects more ultrasound waves and/or with a better efficiency back towards a transmitter. In some embodiments, the pattern is shaped and sized to act as an ultrasound waves reflector, for example a corner reflector. Optionally, the sampling portion and the torque coil are rotated at a selected speed that increases echogenicity.

An aspect of some embodiments relates to retracting a stylet within a biopsy needle prior to sampling. In some embodiments, the stylet is retracted to a pre-determined distance. Alternatively, the retraction distance is adjusted by a user of the biopsy device prior to sampling, for example according to one or more of tissue type, number of desired tissue samples, and/or desired sample volume. Alternatively the stylet is static while the needle is advanced, for example to have an open lumen within the sampling portion and this make the required room for the biopsy sample.

An aspect of some embodiments relates to a stylet with an asymmetrical cross section, for example a non-circular cross section. In some embodiments, a proximal end of a stylet, for example a stylet section closer to a handle, has an asymmetrical cross section. Alternatively or additionally, a stylet distal section, for example a stylet end closer to a sampling portion, has an asymmetrical cross section. Optionally, a portion of the stylet, for example a portion of the stylet body, has an asymmetrical cross section.

According to some embodiments, a stylet proximal end has an asymmetrical cross-section, for example a non-circular cross-section. In some embodiments, the asymmetrical cross-section comprises a "D" shape cross-section. In some embodiments, the distal end having the asymmetrical cross-section interacts, for example fits, a portion in a handle having a complementary cross-section to the asymmetrical cross-section of the distal end. In some embodiments, the interaction between the distal end portion with the asymmetrical cross-section with the complementary cross section of the handle portion prevents, for example, a rotation of the stylet when the sampling portion and/or the torque coil rotate. A potential advantage of prevention or limiting the stylet rotation is that it reduces a probability of stylet fatigue breakage due to the stylet rotation at curved geometry, for example due to the stylet rotation while the stylet is twisted or bent.

An aspect of some embodiments relates to preventing tissue sampling if a sampling portion lumen is occupied. In some embodiments, a stylet in a distal position occupies at least partly an inner lumen of a sampling portion. In some embodiments, retraction of the stylet from the inner lumen allows, for example, penetration of tissue into the sampling portion. In some embodiments, sampling is prevented when the stylet occupies the lumen of the sampling portion. In some embodiments, only when the stylet is retracted, the sampling process, for example penetration of the biopsy needle into the tissue initiates. In some embodiments, at least one sensor, for example an optic sensor, magnetic, or an electric sensor senses a position of the stylet.

An aspect of some embodiments relates to advancing a sampling portion of a biopsy sampling device, for example a biopsy needle, using at least one preloaded energy source. In some embodiments, the biopsy needle is axially advanced and/or rotated using the at least one preloaded energy source. Optionally, the at least one preloaded energy source is a replaceable preloaded energy source. In some embodiments, the at least one preloaded energy source is replaced during the sampling process, for example between each stabbing of the tissue. In some embodiments, the at least one preloaded energy source comprises a spring and/or a flywheel. Optionally, rotation or twisting of the sampling portion or the torque shaft serves as a preloaded energy source.

An aspect of some embodiments relates to preventing adherence of tissue to a sampling portion, for example a needle. In some embodiments, the sampling portion is coated with a low-friction layer, for example to reduce thermal damage to a surrounding tissue during needle movement. Alternatively or additionally, the low-friction layer is configured to prevent adherence of tissue to the external surface of the sampling portion.

According to some embodiments, the low friction layer comprises a tube, a shrink tube, a coating or any other low friction external layer configured to prevent adherence of tissue to the external surface of the sampling portion. In some embodiments, the low friction external layer comprises one or more hydrophobic materials, for example Polytetrafluoroethylene (PTFE), High-density polyethylene (HDPE), PARYLENE or any other hydrophobic material. Alternatively, the low friction external layer comprises hydrophilic materials, for example.

An aspect of some embodiments relates to a braided sampling portion that separates tissue samples while axially advancing into a tissue. In some embodiments, the braided sampling portion rotates in a first direction and/or in an opposite direction during short time periods, for example rotation periods in a range of 0.02-0.1 seconds or 0.5-3 seconds, for example 0.5-1.5 seconds, 1-2.5 seconds, 1.2-3 seconds or any intermediate, smaller or larger range of values.

According to some embodiments, the braided sampling portion rotates in rotation angles smaller than 360° degrees, for example in rotation angle smaller than 270° degrees, smaller than 180° degrees, smaller than 90° degrees, smaller than 45° degrees, or any other smaller or larger rotation angle. Optionally, the braided sampling portion rotates in rotation angles smaller than 360° degrees in both clockwise and counterclockwise directions.

According to some exemplary embodiments, the braided sampling portion rotates in rotation sequences, for example rotation trains of both clockwise and counterclockwise directions. In some embodiments, the rotation of the braided sampling portion during one or more rotation trains is in variable rotation angles and/or for varying time periods, and optionally in different directions.

A potential advantage of rotating the braided sampling portion in rotation trains and/or in opposite directions and/or in short pulses is that it may allow easier separation of tissue samples from different tissue types, for example muscle tissue, fibrotic tissue, necrotic tissue. An additional potential advantage of rotating the braided sampling portion in rotation trains and/or in opposite directions and/or in short pulses is that it may allow to improve fatigue durability, for example fatigue durability of a torque coil and/or of a sampling portion.

According to some embodiments, the braided sampling portion comprises a low-friction layer on the external surface of the sampling portion, for example to reduce friction with the tissue while the braided sampling portion moves relatively to the tissue. In some embodiments, the low friction layer comprises a tube, a shrink tube, or any other low friction external layer configured to prevent adherence of tissue to the external surface of the sampling portion. In some embodiments, the low friction external layer comprises hydrophobic materials, for example Polytetrafluoroethylene (PTFE), High-density polyethylene (HDPE), PARYLENE or any other hydrophobic material. In some embodiments, an external layer on the braided sampling portion, for example the low-friction layer, is configured to prevent passage of tissue and/or liquids through the walls of the sampling portion.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Biopsy Device

According to some exemplary embodiments, a biopsy device is shaped and sized to be introduced at least partly through body lumens to reach a desired anatomical target, for example a selected tissue. Optionally, at least part of the biopsy device is introduced into the body via a working channel of a flexible endoscope or endoscopic ultrasound. In some embodiments, a sampling portion of the device, for example a needle and optionally a removable needle is advanced into the selected tissue to sample at least part of the tissue. Reference is now made to FIG. 1B depicting a biopsy device, according to some exemplary embodiments of the invention.

According to some exemplary embodiments, a biopsy device 102 comprises an elongated sleeve 118, connected to a handle 104. In some embodiments, the sleeve 118 is elastic and bendable, for example to allow bending the sleeve while introducing at least part of the sleeve into the body. Optionally, the sleeve 118 diameter is sized to allow introduction of the sleeve into the body through an anatomical opening or through an artificial opening made in the body. In some embodiments, the sleeve 118 diameter is in a range of 0.60 mm-4 mm, for example 0.6 mm-1.5 mm, 1 mm-2.5 mm, 2 mm-4 mm or any intermediate, smaller or larger range of values.

According to some embodiments, the sleeve 118 comprises an elongated flexible shaft 106 positioned inside and along an internal lumen of the sleeve. In some embodiments, the flexible shaft 106 axially moves within the sleeve 118. Optionally, the shaft 106 axially moves within the sleeve 118, for example to extend from the distal opening from the sleeve during tissue sampling.

In some embodiments, the sleeve 118 is strong enough to isolate the shaft 106 from body tissues during the advancement of the sleeve to a desired anatomical target. In some embodiments, the shaft 106 is made from steel, stainless steel, torque coil, Nitinol or from a compound material. In some embodiments, the shaft length is in a range of 800-2000 mm, for example 1000 mm, 1200 mm, 1250 mm, 1500 mm or any intermediate, smaller or larger value. In some embodiments, the outer diameter of the shaft 106 is in a range of 0.5-4 mm, for example 1.5 mm, 2 mm, 2.5 mm, 3 mm, 3.5 mm or any intermediate, smaller or larger value. In some embodiments, the shaft 106 comprises a braided coil, for example a braided torque coil. In some embodiments, the shaft comprises a torque coil, for example a transmission torque coil. In some embodiments, the shaft is formed by interweaving a plurality of wires. Alternatively or additionally, the shaft is formed by an interleaved mesh.

According to some exemplary embodiments, a shaft that is braided and/or that is formed by interweaved wires or interleaved mesh is treated to prevent passage of fluid and tissue through the shaft wall, for example by adding an external coating. Alternatively or additionally, the shaft is covered by an impermeable layer, for example a tube or a shrink tube. In some embodiments, the shaft is covered by a low friction external layer configured to reduce friction with the surrounding tissue during shaft movement, and/or to prevent adherence of tissue to the outer layer of the shaft. In some embodiments, the low friction external layer comprises hydrophobic materials.

According to some exemplary embodiments, the shaft 106 comprises at the distal end a sampling portion 108. In some embodiments, the sampling portion 108 is part of the shaft 106. Alternatively the sampling portion 108 is a needle, optionally a removable needle. In some embodiments, a gauge value of the sampling portion, for example a gauge value of the needle is in a range of 14-25G, for example 14-18G, 16-20G, 19-25G or any intermediate, smaller or larger range of gauge values. In some embodiments, the maximal angle elevation of the distal tip of the shaft 106 or the sampling portion 108 is 50 degrees, for example 40 degrees, 30 degrees, 20 degrees or any intermediate, smaller or larger elevation angle. In some embodiments, rotation of the elevated shaft or the elevated sampling portion forms a circle with a maximal radius of 40 mm, for example 35 mm, 30 mm, 23 mm or any intermediate, smaller or larger value.

According to some exemplary embodiments, a driving unit 110 axially advances the shaft 106 or the sampling portion 108 in an axial advancement velocity in a range of 0.5 mm/sec to 50 mm/sec, for example 1 mm/sec to 10 mm/sec, 5 mm/sec to 20 mm/sec, 15 mm/sec to 30 mm/sec 25 mm/sec to 50 mm/sec or any intermediate, smaller or larger range of values.

According to some exemplary embodiments, the axial length of the sampling portion is in a range of 40-150 mm, for example 50 mm, 60 mm, 80 mm, 100 mm or any intermediate, smaller or larger value. In some embodiments, the sampling portion 108 comprises a shear section 122 at the distal end of the sampling portion 108. In some embodiments, the shearing portion applies shearing forces on a tissue sample that is placed inside the sampling portion. Alternatively or additionally, the sampling portion applies tensile forces on the tissue sample placed inside the sampling portion In some embodiments, the outer diameter of the sampling portion is in a range of 0.5-2 mm, for example 0.5 mm, 0.7 mm, 1 mm, 1.5 mm or any intermediate, smaller or larger value. In some embodiments, the maximal distal elevation of the sampling portion 108 is 180 degrees, for example 50 degrees, 40 degrees 30 degrees or any intermediate smaller or larger value. Optionally, the elevation mechanism is based on the elevation mechanism of the endoscope. In some embodiments, the maximal rotation radius of the sampling portion 108 at the maximal distal elevation is 40 mm, for example 35 mm, 30 mm, 25 mm or any intermediate, smaller or larger value.

According to some exemplary embodiments, at least part of the shaft 106 is hollow, having an inner lumen extending along the axial length of the shaft 106. In some embodiments, the shaft 106 comprises an internal movable stylet 120 placed inside the lumen of the shaft 106 and extends along the axial length of the shaft. In some embodiments, the stylet 120 extends until the distal end of the shaft. In some embodiments, the stylet 120 extends until or beyond the distal end of the sampling portion 108 and the shear section 122.

According to some exemplary embodiments, the stylet 120 is rigid enough to mechanically support the structure of the shaft 106 when the shaft 106 advances to the desired anatomical target. In some embodiments, the stylet reinforces the hollow structure of the shaft against external forces applied on the shaft 106, for example external forces applied on the shaft by body tissues and/or organs during the advancement of the shaft 106 inside the body. Alternatively or additionally, the stylet 120 mechanically supports the shaft during the bending of the shaft, and optionally allows the shaft to straighten. In some embodiments, the stylet 120 is retracted from the sampling portion 108, as the sampling portion penetrates into a tissue during a sampling process. Optionally, the stylet 120 is retracted when the sampling portion rotates and/or axially advances into the tissue. In some embodiments, the stylet is retracted to reduce forces, for example friction forces between the rotating and/or advancing shaft and the surrounding tissue during tissue sampling.

According to some exemplary embodiments, sleeve 118, the shaft 106 and/or the stylet 120 are movable, and axially move under a control of a control unit 112. In some embodiments, the control unit 112 is part of the handle 104. Alternatively, the control unit 112 is positioned outside the handle 104. Optionally, the control unit comprises at least one locking mechanism, for example an interference locking mechanism for locking the axial and/or rotational movement of the sleeve 118, the shaft 106 and/or the stylet 120.

According to some exemplary embodiments, the handle 104 comprises a driving unit 110, for example a motor and/or a gear functionally connected to the shaft 106. Optionally, the motor is an electric motor or a pneumatic motor. Optionally, the driving unit 10 is positioned outside handle 104. Optionally, the driving unit 10 comprises a gear motor. In some embodiments, the driving unit 10 rotates the shaft 106 and/or the sampling portion 108 of the shaft 106. Alternatively or additionally, the driving unit 10 axially advances the shaft 106 and/or the sampling portion 108 of the shaft 106 into the tissue, for example during a sampling process.

According to some exemplary embodiments, the driving unit 104 is functionally connected, optionally electrically connected to the control unit 112, for example a control circuitry also termed herein as a controller. In some embodiments, the control unit 112 monitors and/or controls the torque of the shaft 106 by monitoring the current of an electric motor of the driving unit 104. Alternatively or additionally, the control unit 104 controls and/or monitors the torque of the shaft 106 using a torque limiter and/or a torque meter.

According to some exemplary embodiments, the driving unit 104 rotates the shaft 106 and/or the sampling portion in a fixed rotation speed of 100-12,000 RPM, for example 300 RPM, 600 RPM, 800 RPM or any intermediate, smaller or larger speed. In some embodiments, the driving unit 10 rotates the shaft 106 and/or the sampling portion 108 in a variable rotation speed in a range of 100-12,000 RPM. In some embodiments, the driving unit 10 axially advances the shaft 106 and/or the sampling portion 108 in an axial advancement velocity in a range of 0.5-50 mm/sec, for example 5 mm/sec, 10 mm/sec, 15 mm/sec or any intermediate, smaller or larger advancement velocity. In some embodiments, the driving unit 110 rotates and axially advances the shaft according to a predetermined ratio between rotation speed and axial advancement velocity.

According to some exemplary embodiments, the driving unit 110 comprises at least one motor, optionally an electric motor configured to rotate and axially advance the shaft by a transmission functionally connected to the shaft. In some embodiments, the transmission comprises a fixed ratio transmission between rotation velocity and axial advancement velocity. Alternatively, the ratio between rotation and axial advancement distance is pre-determined by a user before sampling the tissue, optionally based on the tissue type and/or tissue properties. Optionally, the driving unit comprises at least two motors, one motor for rotating the shaft and one motor for axially advancing the shaft. In some embodiments, the user selects the rotation velocity and the axial advancement velocity independently, optionally according to the tissue type and/or tissue properties.

According to some exemplary embodiments, the driving unit 110 is electrically connected to at least one power source 116, for example at least one battery. In some embodiments, the battery is a lithium-ion battery, for example a 6V lithium-ion battery. Optionally, the at least one battery is a rechargeable battery, for example by plugging an electric charger to a charging socket in the biopsy device. In some embodiments, the power source of the biopsy device is positioned outside the handle 104, is connected to the driving unit 110 by electric wires.

In some embodiments, at 6 V, the electric motor rotates at 1300 RPM and 40 mA without load. In some embodiments, at stall a force of 2 N-cm is applied against the motor and the electrical current drops to 0.36 A.

According to some exemplary embodiments, the biopsy device 102 comprises a user interface, for example user interface 114 positioned in the handle and connected to the control unit 112 and/or to the driving unit 110 and/or to the power source 116. In some embodiments, the interface comprises at least one button and/or at least one selector and/or at least one knob for setting the axial advancement distance of the sleeve 118 and/or the axial advancement distance of the shaft 106. In some embodiments, the user interface 114 is used to set the rotation speed of the shaft and/or the rotation speed of the sampling portion. Alternatively or additionally, the user interface 114 is used to set the ratio between the rotation speed and the axial advancement velocity of the shaft 106 and/or the sampling portion 108.

According to some exemplary embodiments, the user interface 114 is configured to generate a human detectable indication, for example a visible indication and/or a sound indication. In some embodiments, the user interface 114 generates at least one human detectable indication when a maximal penetration depth is reached. Optionally, the user interface 114 generates at least one alert signal when the maximal desired penetration depth is exceeded. In some embodiments, the user interface 114 generates at least one human detectable indication when the rotation speed and/or the axial advancement velocity of the sampling portion or the shaft are not at a desired range of values, or indications for number of rotation cycles.

According to some exemplary embodiments, the handle 104 comprises at least one gripping member shaped and sized to allow gripping of the handle 104 by a hand of a user, for example during the movement of the shaft 106 and/or the movement of the sampling portion 108.

Reference is now made to FIG. 1B depicting an image of a biopsy device, according to some exemplary embodiments of the invention.

According to some exemplary embodiments, a biopsy device, for example biopsy device 150 comprises an elongated handle 152 having at least one gripping member, and a control unit 154 connected to the handle 152 and located outside the handle housing. In some embodiments, the biopsy device 150 comprises an elongated flexible shaft 156 mechanically connected to the control unit 154. Additionally or alternatively, the flexible shaft 156 is mechanically connected to the handle 152. In some embodiments, the flexible shaft is positioned inside an elongated sleeve 158 connected to the control unit 154. In some embodiments, at least part of the flexible shaft 156, for example sampling portion 160 extends out through a distal opening 162 of the elongated sleeve 158. In some embodiments, the sampling portion 160 extends out from the sleeve 158 during a sampling process of a tissue, for example when the sampling portion 160 penetrates into a tissue.

According to some exemplary embodiments, the biopsy device comprises a rotary encoder or a counter functionally connected to the driving unit 104 and to the control unit 112. In some embodiments, the rotary encoder or counter signals the control unit 112 to stop the rotation of the driving unit when a maximal rotation value is reached.

Exemplary General Sampling Process

Figure 2:
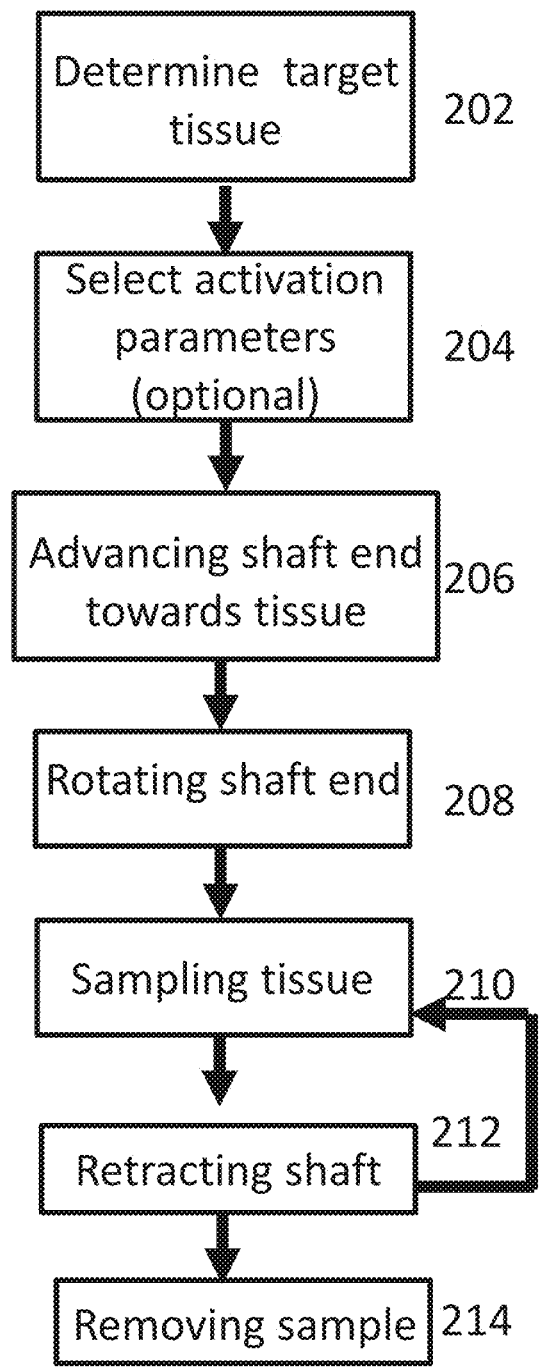
FIG. 2 is a general flow chart of a tissue sampling process, according to some embodiments of the invention.

Reference is now made to FIG. 2, depicting a general process for sampling a tissue, according to some exemplary embodiments of the invention.

According to some exemplary embodiments, a target tissue for sampling is determined at 202, optionally by an expert, for example a physician. In some embodiments, the expert determines the number of samples, and/or the depth of each sample. In some embodiments, the expert determines a navigation path of an endoscope, for example a flexible endoscope or an ultrasound endoscope, for example to a determined diagnostic and intervention location with a good sampling access to target tissue. In some embodiments, the expert selects an endoscope based on the determined target tissue and the determined navigation path, for example an endoscope with a specific diameter and/or length. In some embodiments, the type of biopsy device, for example biopsy devices 102 or 150 are selected, optionally by the expert, based on the determined target tissue and/or based on the determined path to the target tissue, for example a biopsy device with a specific diameter shaft and/or specific shaft length and/or specific sampling portion diameter. In some embodiments, a specific type of a sampling portion, for example sampling portion 108 or 156 is selected at 202, optionally based on the type of the determined target tissue and/or based on the required sample volume of each sample.

According to some exemplary embodiments, at least one activation parameter of the biopsy device is determined at 204. In some embodiments, the axial movement distance is determined at 204, optionally based on a geometrical relation, for example a distance and/or angle between the sampling portion and a target tissue. In some embodiments, the axial movement distance is determined by adjusting a stopper of the biopsy device, configured to mechanically limit the axial advancement of the sampling portion. In some embodiments, the axial advancement distance is limited, for example to prevent tissue damage due to too deep penetration into the tissue. In some embodiments, the rotation speed of the sampling portion during tissue sampling is determined at 204, optionally based on the determined target tissue and/or based on the selected biopsy device. Alternatively or additionally, the axial advancement velocity of the sampling portion during tissue sampling is determined at 204, optionally based on the determined target tissue and/or based on the selected biopsy device. In some embodiments, a ratio between the rotation speed of the sampling portion and the axial advancement velocity of the sampling portion is determined at 204. Alternatively, a user of the biopsy device selects a predetermined ratio of rotation speed/axial advancement velocity from a plurality of predetermined ratios.

According to some exemplary embodiments, a shaft, for example shaft 106 or 156, of the biopsy device is advanced towards the target tissue at 206. In some embodiments, the shaft is advanced within a sleeve, for example sleeve 118 or sleeve 158, optionally according to the determined navigation path. Alternatively, the sleeve remains in the Gastrointestinal (GI) tract while the sampling portion, for example a needle advances toward the target tissue, optionally by penetrating through the GI wall. In some embodiments, the distal end of the shaft is positioned at a close distance from the target tissue, for example at a distance of at least 0.5 mm from the target tissue, for example at a distance of 0.5 mm, 1 mm, 5 mm, 10 mm, 20 mm, 100 mm or any intermediate, smaller or larger distance from the target tissue. Optionally, the distal end of the shaft is positioned at a distance of up to 100 mm from the target tissue, for example 90 mm, 80 mm, 70 mm or any intermediate, smaller or larger value.

According to some exemplary embodiments, the distal end of the shaft facing the tissue, for example the sampling portion rotates at 208. In some embodiments, the sampling portion rotates according to the activation parameters selected at 204. In some embodiments, the sampling portion of the shaft rotates in at least 100 RPM, for example 300 RPM, 600 RPM, 1000 RPM or any intermediate, smaller or larger value.

According to some exemplary embodiments, the target tissue is sampled at 210, optionally while rotating as described at 208. In some embodiments, the target tissue is sampled by axially advancing the rotating sampling portion into the target tissue. In some embodiments, the sampling portion is axially advances into the target tissue with a velocity adjusted to the target tissue type and/or to the rotation speed of the sampling portion. In some embodiments, the sampling portion penetrates into the desired target tissue to a selected and optionally predetermined distance. In some embodiments, the sampling portion penetration distance is at least 1 mm, for example 5 mm, 10 mm, 15 mm, 20 mm or any intermediate, smaller or larger value. In some embodiments, the penetration distance is determined based on the desired sample volume. Alternatively or additionally, the penetration distance is determined based on the target tissue shape, tissue types and surrounding tissues, for example blood vessels and/or nerves in the vicinity of the target tissue. In some embodiments, the desired sample volume is determined by an expert, optionally based on an analysis type, for example a histological analysis and/or a genetic analysis of the tissue sample.

According to some exemplary embodiments, the shaft is retracted at 212. Optionally, the sampling portion is retracted at 212. In some embodiments, the shaft is retracted after reaching a desired penetration depth. In some embodiments, the shaft is retracted after reaching a desired sample volume trapped in the shaft. In some embodiments, the sampling portion is retracted into the sleeve. Alternatively, the sampling portion is retracted but still remains outside of the sleeve.

According to some exemplary embodiments, sampling is repeated, for example to sample a different region of the target tissue. In some embodiments, to reach the different region at least part of the shaft, for example the sampling portion is turned towards the different region. In some embodiments, the repeated sampling step is performed according to the previously defined activation and/or sampling parameters. Alternatively, the repeated sampling step is performed according to modified activation and/or sampling parameters.

According to some exemplary embodiments, the sample is removed from the biopsy device at 214. In some embodiments, the sample is removed from the shaft of the biopsy device by passing a stylet or a shaft with a smaller diameter inside the shaft lumen, optionally through a lumen of the sampling portion of the shaft. Alternatively, saline or air is pushed into the shaft to remove the sample. Optionally, a pump, for example a vacuum pump applies suction force on the sample to allow its removal from the biopsy device. In some embodiments, for example when the sampling portion comprises a needle, optionally a removable needle, the needle with the trapped sample is detached from the shaft, for example to allow sample removal.

Exemplary Ratio Between Rotation Speed and Axial Advancement Velocity

Figure 3A:
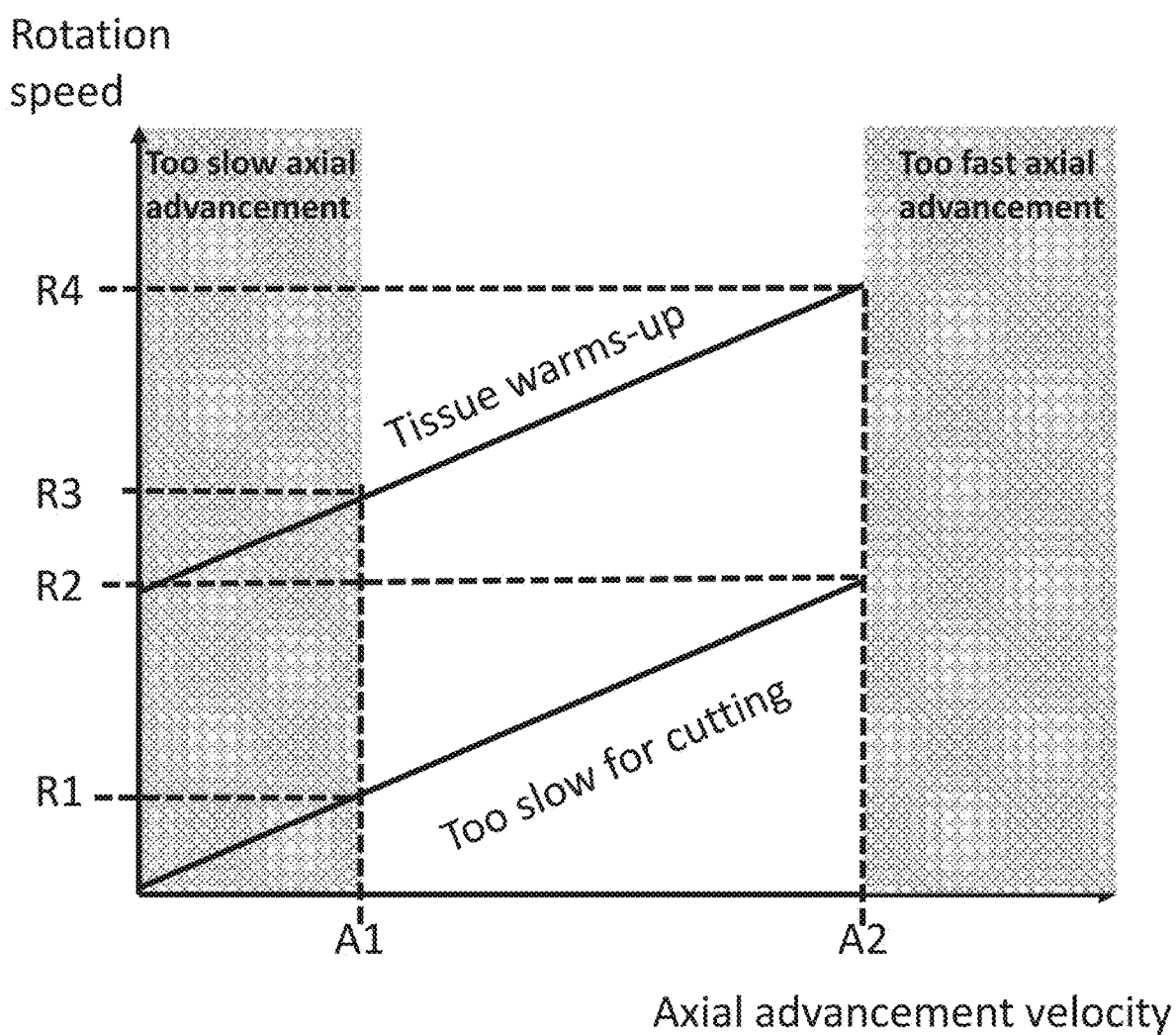
FIG. 3A is a graph showing a relation between axial advancement velocity and rotation speed, according to some embodiments of the invention

According to some exemplary embodiments, a shaft of a biopsy device is rotated while axially advancing into a tissue. In some embodiments, a ratio between the rotation speed and the axial advancement velocity is set, for example to allow efficient sampling without causing damage to the surrounding tissue, for example damage from the kinetic energy of the moving shaft. Reference is now made to FIG. 3A, depicting a graph showing a desired ratio between rotation speed and axial advancement velocity of the shaft, according to some exemplary embodiments of the invention.

According to some exemplary embodiments, an axial advancement velocity value of the shaft into a tissue is set to be higher than a minimal axial advancement velocity value A1. In some embodiments, velocity values smaller than A1 extend the duration of the sampling procedure and therefore are not optimal from the user perspective (e.g. to remain concentrate) or too time consuming. In some embodiments, a maximal axial advancement velocity value of the shaft is set to be smaller than a maximal velocity value A2. In some embodiments, velocity values larger than A2 when the rotation speed is too slow, will cause the moving shaft to compress the tissue without cutting and therefore they do not allow efficient cutting of the tissue. In addition, too high axial velocity will compromise the ability to control the exact location of the needle and imply a risk for the patient especially in the vicinity of important sensitive organs, for example blood vessels and/or nerves. In some embodiments, the axial advancement velocity value of the shaft is set between A1 and A2.

According to some exemplary embodiments, a desired axial advancement velocity value is determined based on at least one parameter of the shaft or the sampling portion of the shaft, for example the diameter of the sampling portion, the shape and/or the width of the cutting edge of the sampling portion. Alternatively or additionally, the axial advancement velocity value is determined based on at least one parameter of the tissue, for example the tissue type and/or tissue density.

According to some exemplary embodiments, a minimal rotation speed value is set to be larger than R1. In some embodiments, rotation speed values smaller than R1 do not allow efficient cutting of the tissue, for example due to weak cutting forces and/or shearing forces and/or tensile forces applied on the tissue by the shaft, optionally by the cutting edge of the shaft. In some embodiments, a maximal rotation speed is set to be smaller than R4. In some embodiments, rotation speed values larger than R4 will generate excessive heat that will cause damage to tissue warm-up.

According to some exemplary embodiments, the minimal and maximal rotation speed values are determined per axial advancement velocity value. In some embodiments, for the minimal axial advancement velocity value A1, the desired rotation speed value is set to be in a range between R1 and R3. In some embodiments, for the maximal axial advancement value A2, a desired rotation speed value is set to be in a range between R2 and R4.

According to some exemplary embodiments, a rotation speed value is determined based on at least one parameter of the shaft or the sampling portion of the shaft, for example the diameter of the sampling portion, the shape and/or the width of the cutting edge of the sampling portion. Alternatively or additionally, the axial advancement velocity value is determined based on at least one parameter of the tissue, for example the tissue type and/or tissue density. In some embodiments, the rotation speed is determined according to a selected axial velocity and/or the axial velocity is determined according to a selected rotation speed.

According to some exemplary embodiments, the axial advancement velocity and/or the rotation speed are determined according to safety parameters of the biopsy device, for example maximal allowed rotation speed of the shaft. Alternatively or additionally, the axial advancement velocity and/or the rotation speed are determined according to safety parameters related to the clinical procedure or target region, for example maximal allowed axial advancement velocity in the vicinity of blood vessels, nerves or other tissue types that need to be avoided during the sampling process.

According to some exemplary embodiments, for example as shown in Table 1 when increasing RPM values, the tissue sample volume of muscle tissue increases, when comparing the sampling volume of different tissues in a fixed axial advancement velocity of 15 mm/sec and in varying rotational velocities.

TABLE 1

| Tissue type | | Rotational velocity [RPM] | | | | |
|---|---|---|---|---|---|---|
| | | 400 | 600 | 800 | 1000 | 1300 |
| Pancreatic tumour simulating tissue | Vol [mm^3] | 2.01 | 2.30 | 2.32 | 2.23 | 2.49 |
| Pancreatic tumour simulating tissue | STD | 0.41 | 0.73 | 0.08 | 0.46 | 0.29 |
| Liver tissue | Vol [mm^3] | 2.10 | 2.04 | 2.15 | 1.94 | 2.06 |
| Liver tissue | STD | 0.65 | 0.41 | 0.16 | 0.57 | 0.58 |
| Muscle tissue | Vol [mm^3] | 1.06 | 0.84 | 1.40 | 1.49 | 2.09 |
| Muscle tissue | STD | 0.17 | 0.22 | 0.11 | 0.20 | 0.18 |

Figure 3B:
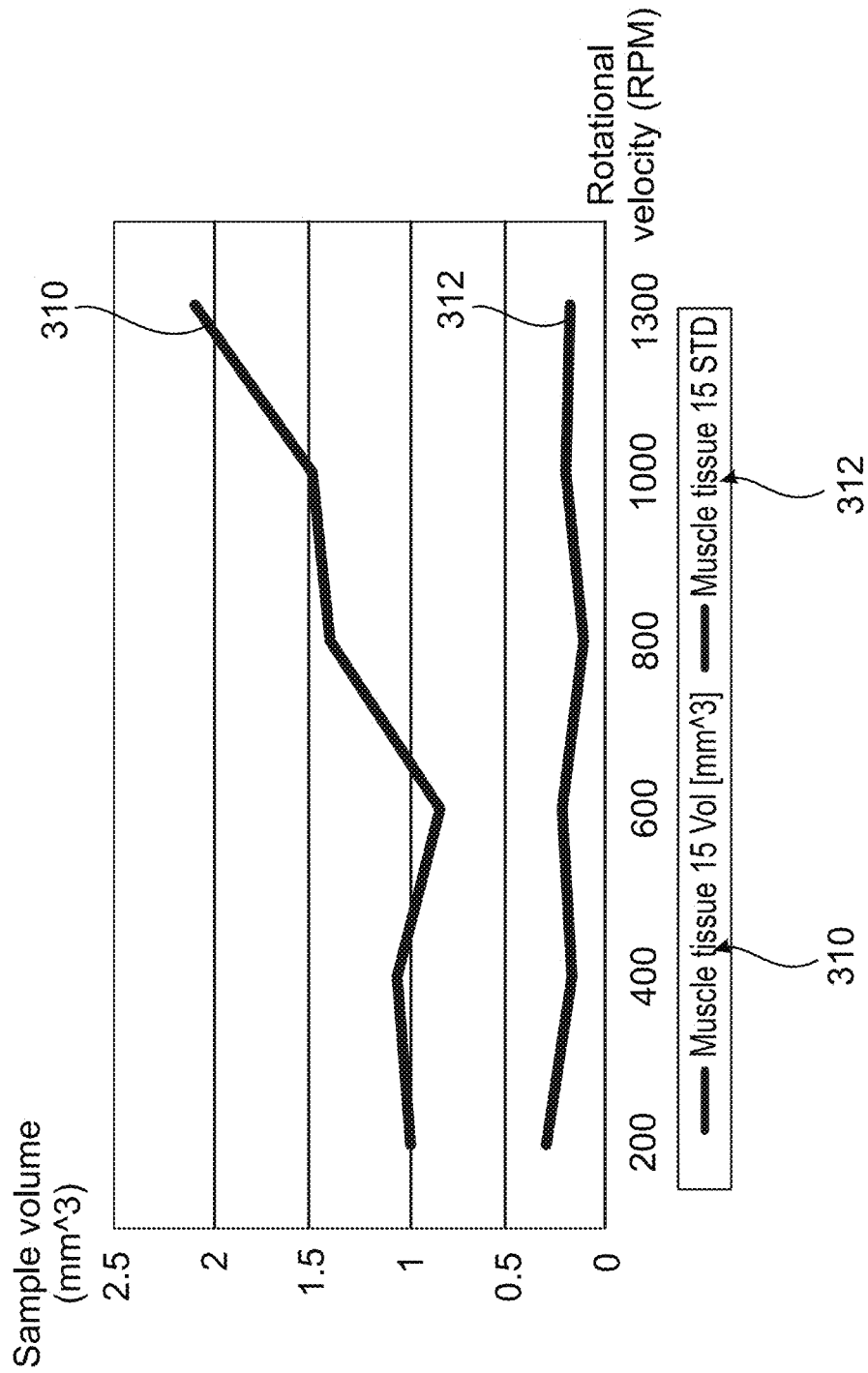
FIG. 3B is a graph showing the change in muscle tissue sample volume in a fixed advancement velocity of 15 mm/sec in different rotational velocities, according to some embodiments of the invention.

According to some exemplary embodiments, for example as shown in table 2 and as shown in FIG. 3B, axial advancement velocity of 15 mm/sec with increasing RPM values results with an increase in muscle tissue sample volume, compared to axial velocities of 1 mm/sec and 5 mm/sec.

TABLE 2

| Tissue type | Axial velocity [mm/sec.] | | Rotational velocity [RPM] | | | | | |
|---|---|---|---|---|---|---|---|---|
| Muscle tissue | | | 200 | 400 | 600 | 800 | 1000 | 1300 |
| Muscle tissue | 1 | Vol [mm^3] | 2.7 | 1.89 | 2.17 | 2.76 | 1.96 | |
| Muscle tissue | 1 | STD | 0.17 | 0.23 | 0.20 | 0.12 | 0.28 | |
| Muscle tissue | 5 | Vol [mm^3] | 0.84 | 2.16 | 1.88 | 1.94 | 1.73 | |
| Muscle tissue | 5 | STD | 0.07 | 0.34 | 0.34 | 0.36 | 0.15 | |
| Muscle tissue | 15 | Vol [mm^3] | 0.99 | 1.06 | 0.84 | 1.40 | 1.49 | 2.09 |
| Muscle tissue | 15 | STD | 0.3 | 0.17 | 0.22 | 0.11 | 0.20 | 0.18 |

Exemplar Sampling Needle Rotation

According to some exemplary embodiments, a sampling needle for example a braided needle, a sampling portion, a sampling portion of a braided coil, or a braided sampling portion, rotates during a tissue sampling process. In some embodiments, the sampling needle rotates during a needle penetration into the tissue and/or as the sampling needle retracts from the tissue.

According to some exemplary embodiments, the sampling needle rotates in different speeds and/or in different rotation angles, for example in rotation angles smaller than 360°, for example rotation angles smaller than 90°, rotation angles smaller than 180°, rotation angles smaller than 270° or any intermediate, smaller or larger rotation angle. Additionally or alternatively, the sampling needle rotates in different directions, for example in a clockwise directions and a counterclockwise direction. Optionally, the sampling needle rotation alternates between a clockwise direction and a counter clockwise direction. In some embodiments, the sampling needle intermittently rotates, for example in pulses. Alternatively, the sampling needle rotates continuously. Optionally, the sampling needle rotates in a fixed or a variable speed. Reference is now made to FIGS. 3C and 3D, depicting rotation angles and/or rotation sequences of a sampling needle, for example a sampling portion, according to some exemplary embodiments of the invention.

According to some exemplary embodiments, the sampling needle rotates for a selected time period in a range of 0.01 seconds-10 seconds, for example 0.01 seconds-2 seconds, 1 second-5 seconds, 2 seconds-10 seconds or any intermediate, smaller or larger rotation duration range.

According to some exemplary embodiments, for example as shown in FIG. 3C, a sampling needle rotates to a maximal rotation angle, for example maximal rotation angle 320, which is in a range of 0-360° degrees, for example 10°, 45°, 90°, 180°, 270° or any intermediate, smaller or larger rotation angle. In some embodiments, the sampling needle rotates to a maximal rotation angle 320 during a time period which is up to 20 seconds. In some embodiments, the sampling portion rotates to a maximal rotation angle 320 in a first direction and then back to a baseline rotation angle, for example a baseline rotation angle is a rotation angle when rotation initiates. In some embodiments, the sampling portion rotates to a maximal rotation angle 320 and back to a baseline rotation angle during time period 321. In some embodiments, time period 321 is in a range of 1-40 seconds, for example 1-20 seconds, 5-30 seconds, 25-40 seconds or any intermediate, smaller or larger range of values.

According to some embodiments, the sampling needle rotates to a maximal rotation angle which is equal or larger than 360° degrees, for example maximal rotation angle 322, for example 360°, 720°, 1440° or any intermediate, smaller or larger maximal rotation angle. In some embodiments, the sampling needle rotates to a maximal rotation angle 322 in one direction and back to a baseline rotation angle, optionally during time period 321 or any shorter or longer time period. In some embodiments, the sampling needle rotates to a maximal rotation angle 320 and back to a baseline rotation angle during time period 324 which is longer than time period 321, for example a time period in a range of 1-60 seconds, for example 1-20 seconds, 15-50 seconds, 40 seconds-60 seconds or any intermediate, smaller or larger range of values.

According to some exemplary embodiments, the sampling needle rotates in a train of rotation pulses, for example rotation pulses train 326. In some embodiments, a rotation pulses train comprises two or more consecutive rotation pulses, for example rotation pulses 328 and 330. In some embodiments, in each pulse the sampling needle rotates to maximal rotation angle, for example maximal rotation angle 320 or 322, and back to a baseline rotation angle. Optionally, the maximal rotation angle varies between two or more consecutive pulses. Alternatively or additionally, the time duration of each pulse is similar between all pulses in a train or varies between at least some of the pulses of a train.

According to some exemplary embodiments, a rotation pulses train comprises two or more rotation pulses with a time interval between them, for example time interval 331 between pulse 330 and pulse 332. In some embodiments, the time interval comprises a time interval with a maximal duration in a range of 0.1 second-10 seconds, for example in a range of 0.1 seconds-2 seconds, 1 second-7 seconds, 6 seconds-10 seconds or any intermediate, smaller or larger value or range of values. In some embodiments, all rotation pulses in a train have a similar rotation angle, a similar rotation speed and/or similar rotation duration. Alternatively, at least one of rotation angle, rotation speed, rotation duration is different between two or more rotation pulses of a rotation pulses train.

According to some exemplary embodiments, a rotation pulses train comprises two or more rotation pulses, each comprises a maximal rotation angle which is smaller than 360°, for example as shown by rotation pulses train 326. Alternatively, each of the two or more rotation pulses have a rotation angle which is larger than 360°, for example rotation pulses 336, 338 and 340 of rotation pulses train 334. Optionally, some of the rotation pulses in a rotation pulses train comprise a maximal rotation angle which is larger than 360° degrees and optionally some of the rotation pulses in the rotation pulses train comprise a maximal rotation angle which is smaller than 360° degrees.

According to some exemplary embodiments, for example as shown in FIG. 3D, the sampling needle rotates to a first maximal rotation angle in a first direction and to second maximal rotation angle in the opposite direction. In some embodiments, the first maximal rotation angle is similar to the second maximal direction. Alternatively, the first maximal rotation angle is different, for example smaller or larger than the second rotation angle. Optionally, a rotation duration at the first direction is similar or different from a rotation duration at the second duration. In some embodiments, the rotation of the sampling needle in a first direction is similar or different from the rotation of the sampling needle in an opposite direction, for example when the rotation in opposite directions is part of a train of rotation pulses.

According to some exemplary embodiments, for example as shown in FIG. 3D, a train of rotation pulses comprises two or more rotation pulses with maximal rotation angles at two different directions, for example maximal rotation angles 342, 344 and 346 of rotation pulses train 340. In some embodiments, two or more consecutive rotation pulses, comprise rotation at two opposite directions, for example one rotation pulse rotates in a clockwise direction and a second rotation pulse rotates in a counter clockwise direction. In some embodiments, at least one rotation pulse includes rotating a sampling needle in a maximal a rotation angle which is smaller than 0° degrees. As used herein, one or more rotation angles which are smaller than 0° degrees are a rotation angles in an opposite direction to one or more rotation angles which are larger than 0°.

According to some exemplary embodiments, one or more rotation pulses comprises rotation of the sampling needle to maximal rotation angles that are larger than 360° degrees in a first direction followed by rotating the sampling needle in an opposite direction to maximal rotation angles larger than 360° degrees, for example maximal rotation angles 348 and 350 shown in FIG. 3D.

Figure 1B:
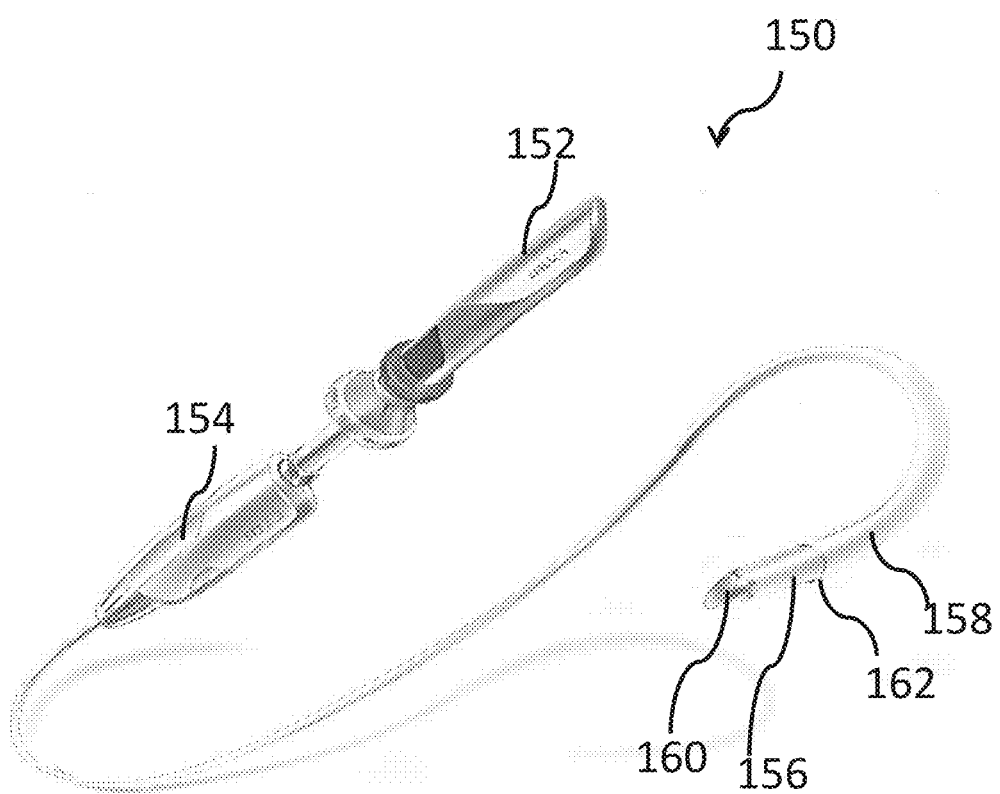
FIG. 1B is an image of a biopsy device, according to some embodiments of the invention.

According to some exemplary embodiments, a control unit of the biopsy device, for example control unit 112 of device 102 shown in FIG. 1A, controls one or more of rotation parameters comprising rotation angle, maximal rotation angle, rotation direction, rotation speed, and/or number of rotations and rotation parameters of each rotation pulse in a train of rotation pulses. In some embodiments, the control unit controls the one or more rotation parameters based on values stored in a memory of the biopsy device and/or based on signals received from a user interface of the device, for example user interface 114 shown in FIG. 1A.

A potential advantage of rotating a sampling needle in small angle rotations, rotation pulses, and/or varying speeds is that it may allow efficient tissue separation from different tissue types with various density and/or different cell composition.

Exemplary Detailed Sampling Process

Figure 4A:
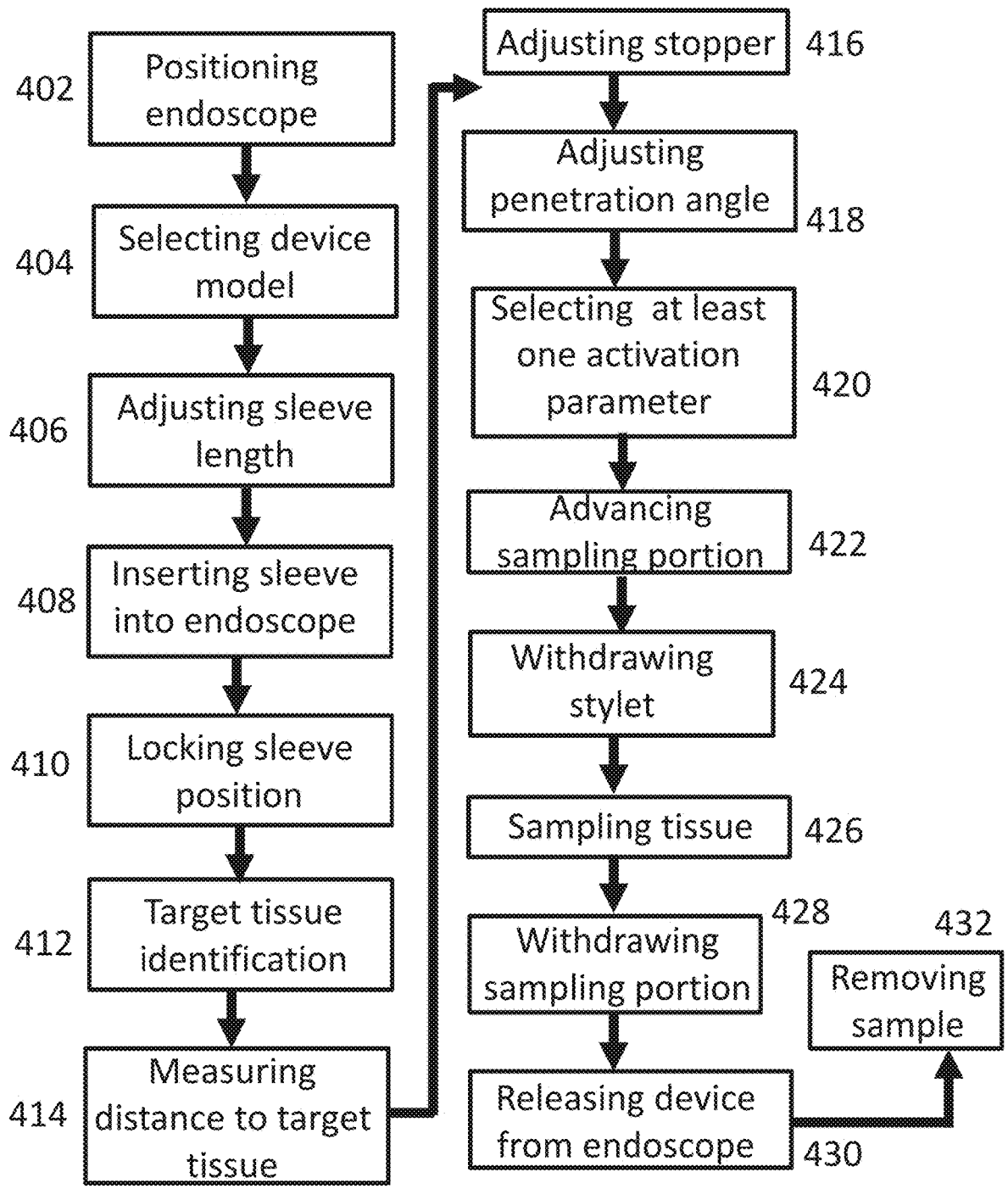
FIG. 4A is a detailed flow chart of a tissue sampling process, according to some embodiments of the invention.

Reference is now made to FIG. 4A, depicting a detailed tissue sampling process, according to some exemplary embodiments of the invention.

According to some exemplary embodiments, an endoscope, for example a flexible endoscope, optionally an ultrasound endoscope is introduced into the body and positioned at a desired location at 402. In some embodiments, a distal end of the endoscope, for example a leading end of the endoscope facing a tissue, is positioned near a target tissue.

According to some exemplary embodiments, a biopsy device model is selected at 404. In some embodiments, the biopsy device is selected based on a desired ratio between axial advancement velocity of the biopsy device shaft and a rotation speed of the shaft. Optionally, the desired ratio is determined based on the tissue type and/or tissue properties, for example tissue density. In some embodiments, the biopsy device is selected according to a target tissue type, for example a biopsy device designed for sampling muscle tissues is selected when the target tissue is muscle. In some embodiments, a biopsy device designed for sampling pancreatic tissue is selected at 404 when the target tissue is pancreatic tissue.

According to some exemplary embodiments, the biopsy device model is selected based on the endoscope type. Alternatively or additionally, the biopsy device is selected based on the size, for example the inner width or inner diameter of the working channel of the endoscope. In some embodiments, the selected biopsy device comprises a shaft surrounded by a sleeve with an outer diameter smaller than the diameter of the working channel of the endoscope.

According to some exemplary embodiments, the biopsy device is selected at 404 based on the position of the distal end of the endoscope within the body. Alternatively or additionally, the biopsy device is selected based on the distance between the distal end of the endoscope from the target tissue and/or an angle between the distal end of the endoscope and the target tissue.

According to some exemplary embodiments, a length of the biopsy device sleeve, for example sleeve 118 or sleeve 158, is adjusted at 406. In some embodiments, the sleeve is adjusted according to the length of the working channel of the endoscope. Alternatively or additionally, the sleeve length is adjusted according to the distance between the endoscope distal end and the target tissue.

According to some exemplary embodiments, the sleeve is inserted into the endoscope at 408. In some embodiments, the sleeve is inserted, optionally threaded, into the working channel of the endoscope.

According to some exemplary embodiments, a locking mechanism is activated, for example to lock the position of the sleeve at the desired position within the working channel at 410. In some embodiments, the sleeve locking mechanism comprises an interference fit locking mechanism, for example a press-fit, a taper-fit and/or a shrink-fit mechanism. In some embodiments, the taper-fit mechanism comprises a luer lock. Optionally, the luer lock is tightened at 410.

According to some exemplary embodiments, a target tissue is identified at 412. In some embodiments, the target tissue comprises a tumor, for example submucosal lesions, mediastinal masses, lymph nodes and intraperitoneal masses within or adjacent to the gastrointestinal tract. In some embodiments, the tumor is a solid tumor. In some embodiments, the tumor is identified by visualization means, for example a camera connected to the endoscope. Alternatively or additionally, the tumor is identified by imaging means, for example an imaging unit connected to the endoscope or an external imaging device. In some embodiments, the imaging means comprises ultrasound imaging. In some embodiments, the ultrasound imaging is performed by an ultrasound probe positioned inside the body, optionally connected to the endoscope, or by an ultrasound probe positioned outside the body.

According to some exemplary embodiments, a distance to the target tissue is measured at 414. In some embodiments, the distance to the target tissue is measured using the camera or the ultrasound device. Optionally, the distance to the target tissue is measured, for example to limit the axial advancement of a sampling portion of the shaft, for example a needle, within the sleeve.

According to some exemplary embodiments, a stopper is adjusted at 416. In some embodiments, a stopper, for example a mechanical stopper position is adjusted, optionally based on the distance measured at 414. In some embodiments, the position of a stopper is adjusted to limit the axial advancement distance of the sampling portion of the shaft. Optionally, the axial advancement distance is determined by limiting the rotations number of the shaft or by limiting any other parameter controlling the axial advancement of the shaft.

According to some exemplary embodiments, the penetration angle is adjusted at 418. In some embodiments, the penetration angle is the angle between the sampling portion of the shaft and the outer surface of the target tissue.

According to some exemplary embodiments, at least one activation parameter of the biopsy device is selected at 420. In some embodiments, the at least one activation parameter comprises shaft rotation speed, shaft axial advancement velocity, and/or sampling duration and/or number of cycles and/or the axial advancement distance.

According to some exemplary embodiments, the sampling portion of the shaft is advanced towards a target tissue at 422. In some embodiments, the sampling portion is advanced through body lumen and cavities towards the target tissue. In some embodiments, the sampling portion is advanced through the stomach and/or duodenum wall towards the target tissue.

According to some exemplary embodiments, an elongated stylet positioned within the shaft is withdrawn or retracted at 424. In some embodiments, the elongated stylet positioned within the sampling portion of the shaft is withdrawn. In some embodiments, the stylet is withdrawn to a distance of at least 20 mm from the distal end of the shaft, for example 30 mm, 50 mm, 80 mm, 100 mm or any intermediate smaller or larger distance.

According to some exemplary embodiments, the target tissue is sampled at 426. In some embodiments, the tissue is sampled by penetration of the sampling portion of the shaft into the target tissue. In some embodiments, the sampling portion is rotated while penetrating into the target tissue. Optionally, the sampling portion rotates in at least 100 RPM. In some embodiments, the sampling portion is moved by a motor into the target tissue, optionally according to a fixed ratio between rotation speed and axial advancement velocity. In some embodiments, the sampling portion penetrates into the target tissue at different locations, and optionally if different penetration angles.

According to some exemplary embodiments, the target tissue is sampled by applying friction forces on part of the target tissue positioned inside a lumen of the sampling portion, and shearing and/or cutting and/or tensile forces that are applied on a different part of the target tissue located closer to the distal opening of the sampling portion. In some embodiments, the applied shearing and/or tearing and/or tensile forces cause the part of the tissue positioned inside the lumen of the sampling portion to separate from the target tissue located outside the sampling portion. In some embodiments, a suction force is applied to keep the target tissue sample inside the sampling portion and/or inside the lumen of the shaft.

According to some exemplary embodiments, the sampling portion is retracted at 428. In some embodiments, the sampling portion of the shaft is retracted from the target tissue, and optionally into the sleeve. In some embodiments, the sampling portion is retracted while rotation is stopped.

According to some exemplary embodiments, the biopsy device is released from the endoscope at 430. In some embodiments, the biopsy device is released from the endoscope by inactivating the interference fit locking mechanism activated at 410. In some embodiments, the biopsy device is released from the endoscope by unlocking the press-fit, taper-fit and/or shrink-fit mechanisms locked at 410. Optionally, the biopsy device is released from the endoscope at 430 by unlocking the luer lock.

According to some exemplary embodiments, the tissue sample is removed at 432. In some embodiments, the tissue sample is removed by advancing forward the stylet, for example to push the tissue sample out from the shaft. Alternatively or additionally, saline or air is blown through the shaft lumen to push the tissue sample out from the shaft. In some embodiments, the sampling portion and/or part of the shaft holding the tissue sample is removed to release the tissue sample. Alternatively, fluid is pumped into the shaft lumen to release the tissue sample. In some embodiments, vacuum forces are applied from at least one opening of the shaft to remove the tissue sample, for example by suction.

According to some exemplary embodiments, the tissue sample is analyzed while in the biopsy device. In some embodiments, the tissue sample is analyzed by a microscope and/or by an imaging device. Alternatively or additionally, the tissue sample is analyzed by at least one sensor, for example a sensor that measures the emission of radioactive energy from the tissue sample, for example when the target tissue is treated by brachytherapy or any other type of radioactive therapy.

Exemplary Tissue Sampling

According to some exemplary embodiments, a sampling portion, for example a needle, of a flexible shaft is engaged with a target tissue. In some embodiments, the sampling portion engages with the target tissue, for example to remove a tissue sample from the target tissue without causing damage to the target tissue. Reference is now made to FIGS. 4B-4E depicting a sampling process of a target tissue, according to some exemplary embodiments of the invention.

Figure 4B:
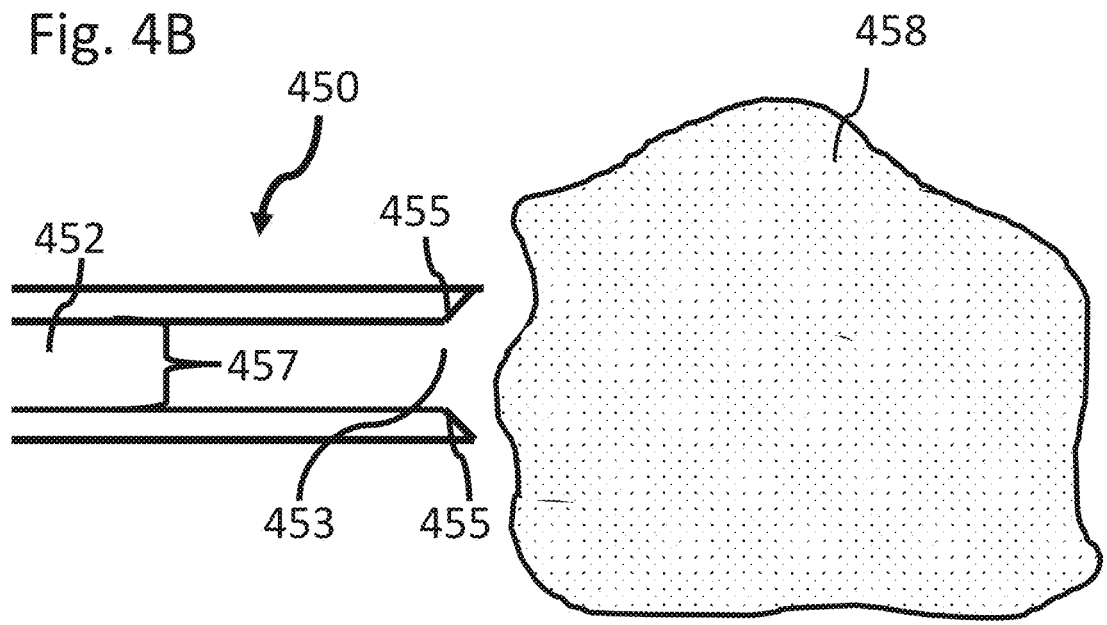
FIGS. 4B-4E are schematic illustrations of a tissue sampling process using a biopsy device with a rotating hollow shaft, according to some embodiments of the invention.

According to some exemplary embodiments, for example as shown in FIG. 4B, a sampling portion 450 is positioned near or in a target tissue 458 where a distal opening 453 of the sampling portion faces the target tissue 458. In some embodiments, the sampling portion 450 is located at a distal end of a shat and includes a lumen 452 extending from the distal opening 453 of the sampling portion 450. In some embodiments, an inner diameter of the sampling portion, for example the diameter 457 is at least 0.2 mm, for example 0.3 mm, 0.5 mm, 0.7 mm, 1 mm or any intermediate smaller or larger diameter.

According to some exemplary embodiments, the sampling portion 450 comprises a circumferential leading edge 455 at the distal end of the sampling portion 450. In some embodiments, the leading edge 455 is shaped and sized for cutting the target tissue when the sampling portion 450 advanced into the target tissue 458. In some embodiments, the leading edge 455 is a tapered or angled edge.

According to some exemplary embodiments, the outer surface 454 of the sampling portion 450 is shaped to reduce friction forces between the sampling portion 450 and the target tissue. Additionally or alternatively, the outer surface 454 of the sampling portion 450 is shaped to reduce tearing and/or warm up of the tissue, for example by having a smooth surface area or a flat surface area. Optionally, the outer surface of the sampling portion is covered with a layer of a low friction material.

According to some exemplary embodiments, at least part of the inner surface 451 of the sampling portion 450 is shaped to apply sufficient friction forces on an inner tissue found inside the lumen 452, for example to allow gripping of the tissue. In some embodiments, the inner surface comprises at least one geometrical element shaped and to increase a contact area with the inner tissue. In some embodiments, the geometrical element comprises at least one bulge and/or at least one protrusion, for example an axial protrusion or a circumferential protrusion. In some embodiments, the circumferential protrusion comprises a helical protrusion at least partially surrounding the lumen 452.

Figure 4C:
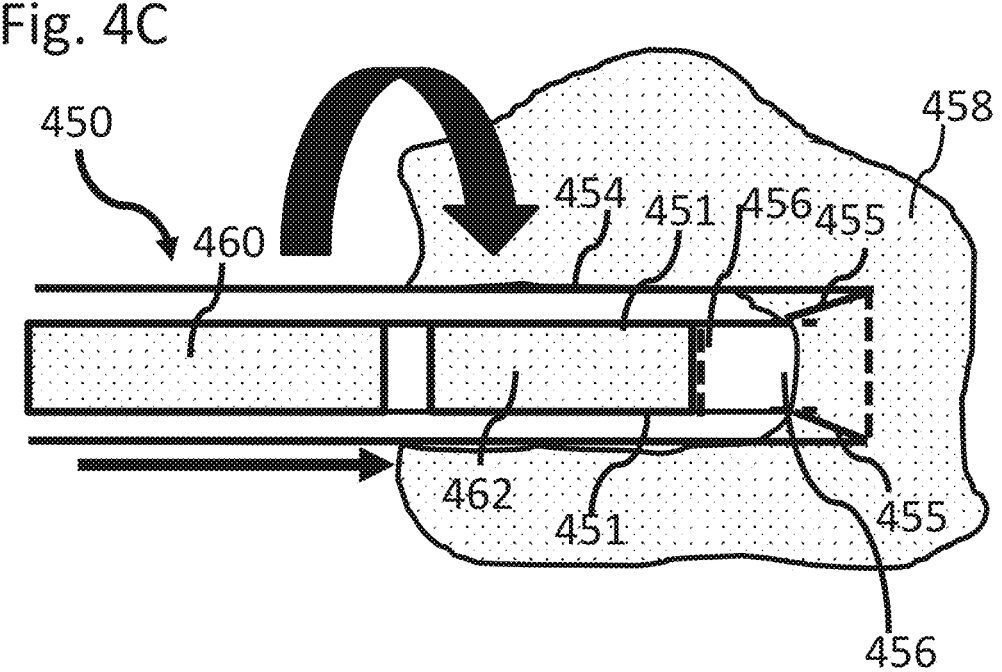
Figure 4D:
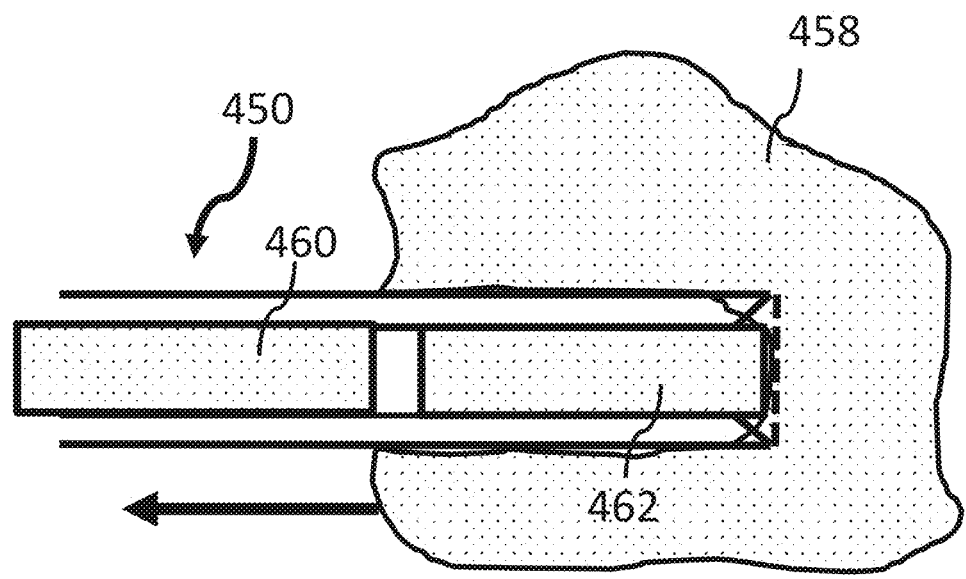

According to some exemplary embodiments, for example as shown in FIG. 4C, the sampling portion 450 rotates clockwise or counterclockwise while axially advancing forward into the target tissue 458. In some embodiments, as the sampling portion 450 advances into the target tissue 458, the leading edge 455 cuts through the target tissue 458. In some embodiments, the leading edge 455 performs a circular cut in the target tissue 458 while an uncut area of the target tissue in the center of the circular cut enters through the distal opening 453 into the internal lumen 452 of the sampling portion 450.

According to some exemplary embodiments, the inner surface 451 of the sampling portion 450 applies friction forces on the uncut tissue found inside the sampling portion, also termed herein as inner tissue, for example tissue 462 found inside the lumen. In some embodiments, the friction forces applied by the inner surface 451 of the sampling portion reduces the movement velocity of the inner tissue relative to the movement velocity of the sampling portion. In some embodiments, the difference between relative movement velocities of the inner tissue and the target tissue located outside the internal lumen 452 of the sampling portion 450 or partly within the lumen generates a shearing area 456 where shearing and/or cutting forces and/or tensile forces are applied on the inner tissue. In some embodiments, the shearing forces in the shearing area 456 and/or the tensile forces separate the inner tissue from the target tissue.

According to some exemplary embodiments, a ratio between a rotation speed and an axial advancement velocity of the sampling portion 450 is predetermined, for example to allow efficient cutting of the target tissue by the leading edge 455 and/or to generate sufficient shearing and/or tensile forces to separate a tissue sample, for example the inner tissue from the target tissue 458. In some embodiments, and as previously described in FIG. 3A, the ratio is predetermined or adjusted according to the target tissue type, the target tissue composition and/or the target tissue properties, for example size and/or density of the target tissue.

According to some exemplary embodiments, as the sampling portion advances through the target tissue 458, the outer surface 454 of the sampling portion applies friction forces on part of the target tissue surrounding the sampling portion 458. In some embodiments, and as described above, the outer surface 454 is shaped to reduce the friction forces, for example to reduce tissue heating which optionally leads to tissue damage.

According to some exemplary embodiments, once the amount of sampled tissue is sufficient and/or when reaching a maximal predetermined penetration depth, the sampling portion 450 is retraced. In some embodiments, during the retraction, the rotation of the sampling portion 450 is stopped, for example to reduce friction forces applied by the outer surface of the sampling portion on the surrounding target tissue.

According to some exemplary embodiments, the sampling portion 450 advances again into the target tissue 458, optionally in a different region of the target tissue 458 to remove at least one additional tissue sample from the target tissue 458. In some embodiments, to reach a different region of the target tissue 458 the sampling portion is bend in an angle of up to 50 degrees, for example 10 degrees, 20 degrees, 40 degrees or any intermediate, smaller or larger angle.

Figure 4E:
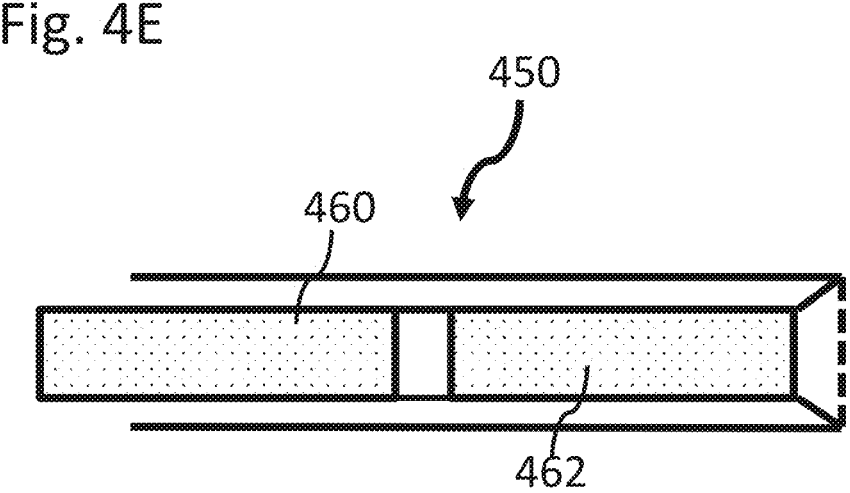

According to some exemplary embodiments, for example as shown in FIG. 4E, the sampling portion 450 is retracted from the target tissue, and contains at least one tissue sample, for example 2, 3, 4 or any larger number of tissue samples. In some embodiments, the sampling portion 450 applies sufficient friction forces on the at least one tissue sample, for example tissue samples 460 and 462, to hold the tissue samples within the sampling portion lumen during the retraction.

Exemplary Biopsy Device with an Operation Control

Figure 4F:
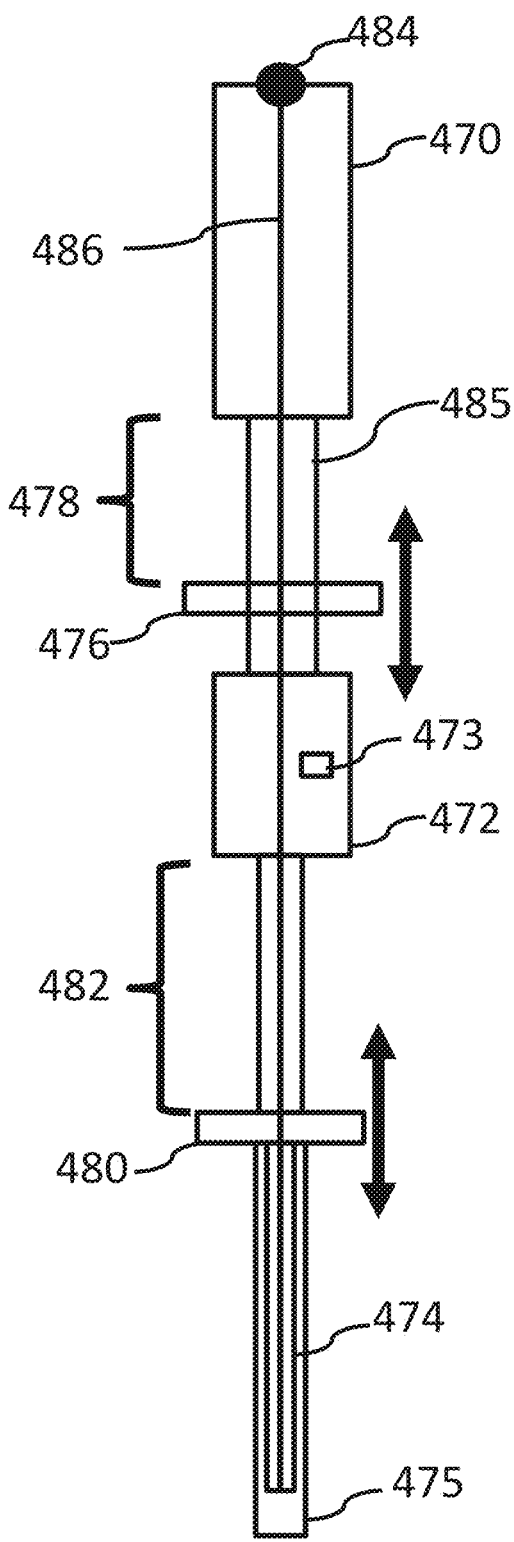
FIGS. 4F-4H are schematic illustrations of a handle and a control unit of a biopsy device, according to some embodiments of the invention.
Figure 4G:
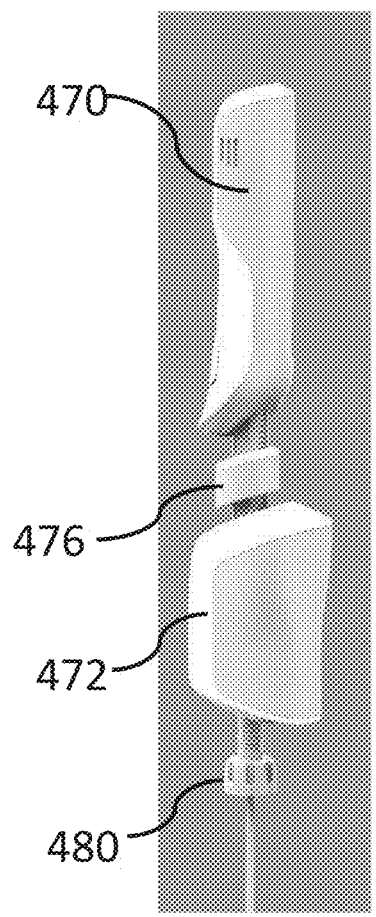
Figure 4H:
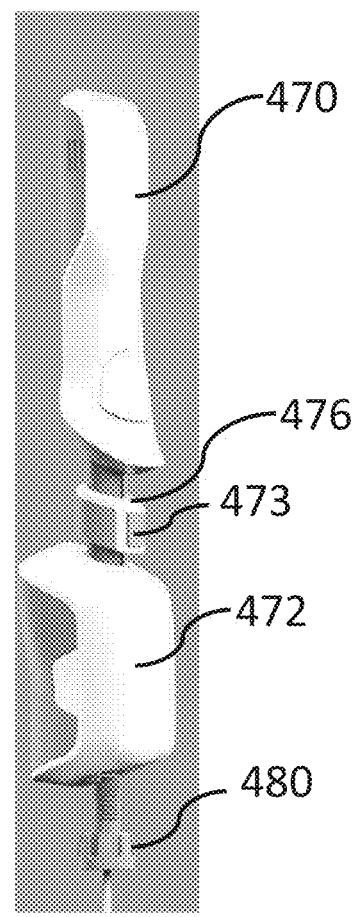

According to some exemplary embodiments, a biopsy device comprises a handle connected to an elongated shaft with a sampling portion. In some embodiments, the handle at least partially controls the movement of the elongated shaft, for example rotation and/or axial movement towards a target tissue. Alternatively or additionally, a control unit is connected to the shaft with the sampling portion. In some embodiments, the control unit at least partially controls the movement of the elongated shaft, for example rotation and/or axial movement of the shaft towards a target tissue. Reference is now made to FIGS. 4F-4H depicting a handle with a control unit of a biopsy device, according to some exemplary embodiments of the invention.

According to some exemplary embodiments, a biopsy device comprises a handle, for example handle 470 connected to an elongated shaft 474. In some embodiments, the shaft is placed within a sleeve, for example sleeve 475. In some embodiments, the handle 470 comprises at least one gripping member for holding the handle by a user of the biopsy device as the shaft is introduced into the body towards a target tissue. Alternatively or additionally, the at least one gripping member of the handle is used for holding the handle 470 by a user of the biopsy device during a tissue sampling process, for example during the rotation and/or axially advancement of the shaft 474. In some embodiments, the handle 470 controls the axial advancement of the shaft 474. Alternatively or additionally, the handle 470 is used to adjust the length of the sleeve 475.

According to some exemplary embodiments, the biopsy device comprises a control unit 472, functionally connected to the sleeve 475 and/or to the shaft 474. In some embodiments, the control unit 472 is used to adjust the length of the sleeve 475, for example to adjust the length of the sleeve according to the distance to the target tissue or according to the length of a working channel of an endoscope. In some embodiments, the control unit 472 is used to axially move the sleeve 475 and optionally a connector coupled to the sleeve, for example connector 480. Optionally, the connector is part of a locking mechanism, for fixing the sleeve 475 length at a desired length. Alternatively, the locking mechanism is part of the control unit 472.

According to some exemplary embodiments, the handle 470 is connected to the control unit 472 by an elongated tube 485, optionally a hollow tube. In some embodiments, a stopper, for example stopper 476, optionally connected to the tube limits the advancement distance 478 between the handle 470 and the control unit 472. In some embodiments, when the shaft is advanced towards the target tissue, handle moves towards the control unit. In some embodiments, the stopper 476 limits the movement range of the handle 470. In some embodiments, the stopper 476 is a movable stopper configured to axially move along the tube 485 length, and optionally to be tightened or locked around the tube 485 at a desired position. Optionally, the stopper 476 moves by pressing a button, for example button 473. In some embodiments, when button 473 is pressed a locking mechanism, for example an interference locking mechanism is released to allow the movement of the stopper 476. In some embodiments, when the button 473 is in a relaxed state, the locking mechanism is engaged, for example to prevent the movement of the stopper 476.

According to some exemplary embodiments, a stylet, for example stylet 486 passes along a lumen of the shaft, through the control unit 472, and optionally through the handle 470. In some embodiments, the stylet 486 is a movable stylet and axially moves within the shaft 474, for example prior to the rotation of the shaft and/or penetration of at least part of the shaft into a target tissue. In some embodiments, the stylet is automatically axially retracted by pushing a sampling button, for example activation button 560 and preventing the ability to forget to retract it. Alternatively or optionally, if the stylet is in a distal position it disables the activation of the sampling by a mechanical mechanism or by a sensor connected to the control unit.

According to some exemplary embodiments, a movement control mechanism located at the handle 470 for example control mechanism 484, and/or in the control unit, controls the advancement and/or the retraction of the stylet 486. In some embodiments, the control mechanism retracts the stylet 486 prior to sampling, for example to form a lumen within the shaft sized for holding a tissue sample. In some embodiments, the control mechanism pushes the stylet 486 forward, for example to release a tissue sample trapped inside the shaft or inside a sampling portion of the shaft. In some embodiments, when the stylet 486 is retracted, the control mechanism locks the stylet 486 in a retracted position.

Figure 5A:
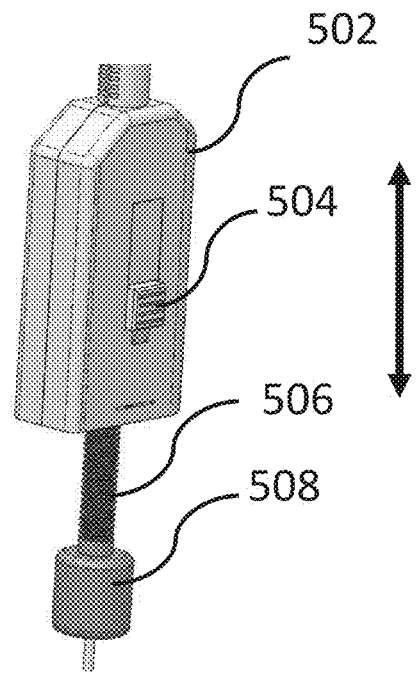
FIGS. 5A-5P are schematic illustrations of parts of a biopsy device during a tissue sampling process, according to some embodiments of the invention.
Figure 5B:
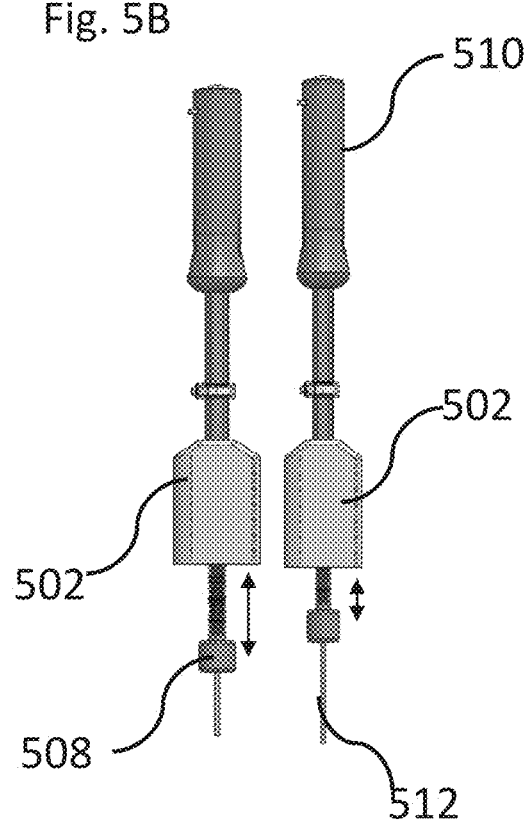
FIGS. 5Q-5S are schematic illustration of a handle and a control unit with a user interface, according to some embodiments of the invention.
Figure 5C:
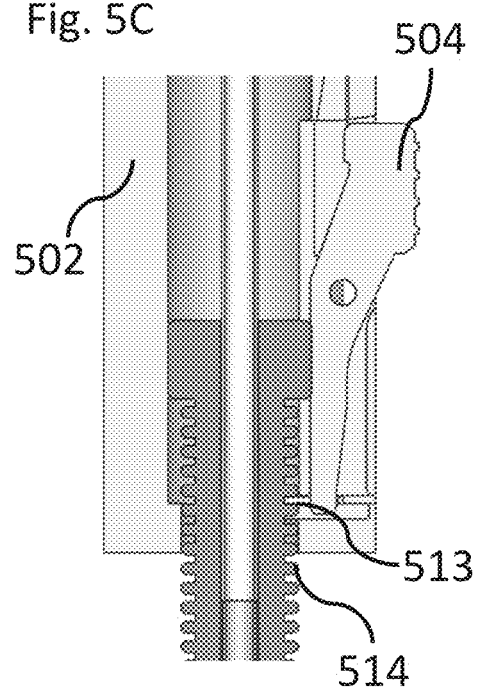

Reference is now made to FIGS. 5A-5C depicting a process for adjusting the sleeve length, according to some exemplary embodiments of the invention.

According to some exemplary embodiments, a biopsy device comprises a control unit 502, connected to a sleeve connector 508 through an elongated adaptor 506. In some embodiments, the adaptor 506 is configured and operable to slide within the control unit 502, for example by moving a sliding button 504 at least partially extending from the control unit. In some embodiments, the button 504 is connected to a protrusion 513 placed inside a slit or a notch, for example notch 514 in the outer surface of the adaptor.

Figure 5D:
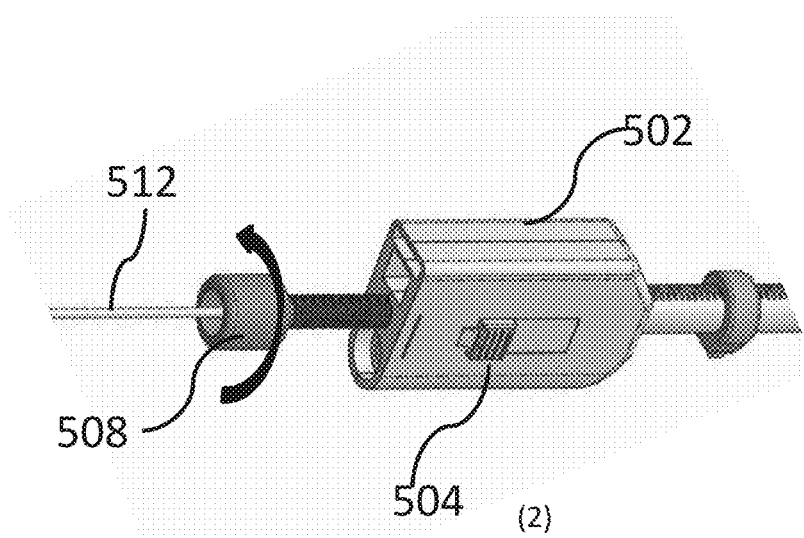

According to some exemplary embodiments, a user slides the sliding button 504, for example to adjust a sleeve 512 length. In some embodiments, when reaching a desired length of the sleeve 512, the sleeve connector is locked, for example to prevent any axial movement of the sleeve. In some embodiments, for example as shown in FIG. 5D, the sleeve connector comprises an interference fit locking mechanism. In some embodiments, the interference fit locking mechanism comprises a press-fit, a taper-fit or a shrink-fit mechanism. In some embodiments, the taper-fit mechanism comprises a luer lock. Optionally, a luer lock is tightened to prevent any further axial movement of the sleeve. Alternatively, the interference fit locking mechanism is positioned in the control unit 502 and is optionally connected to the sliding button 504.

Figure 5E:
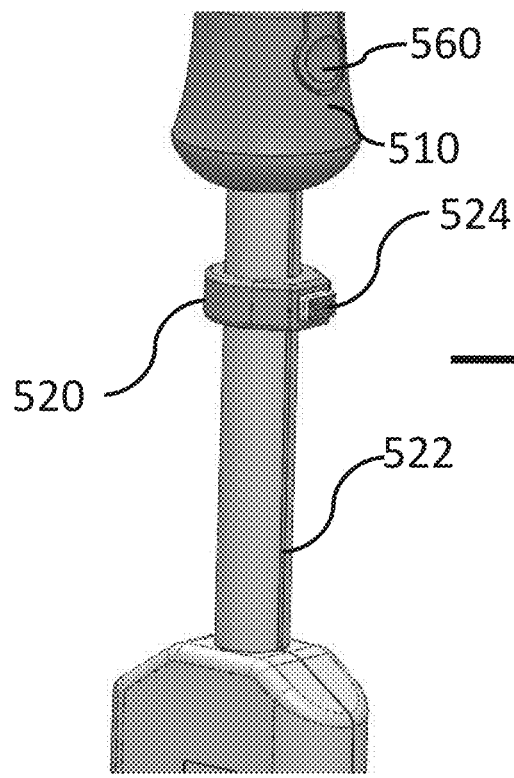
Figure 5F:
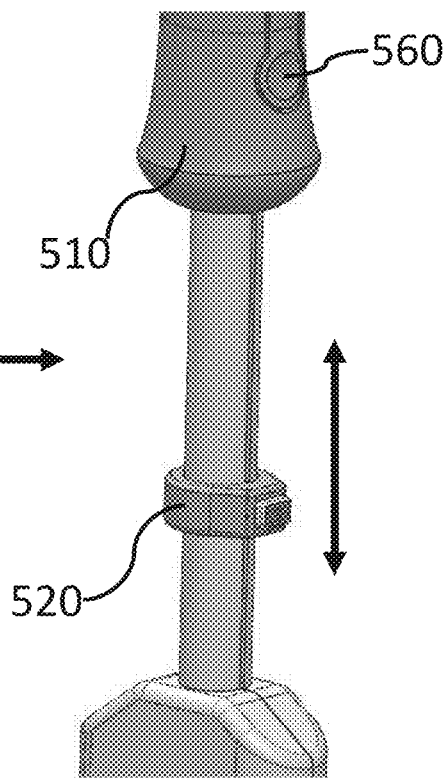
Figure 5G:
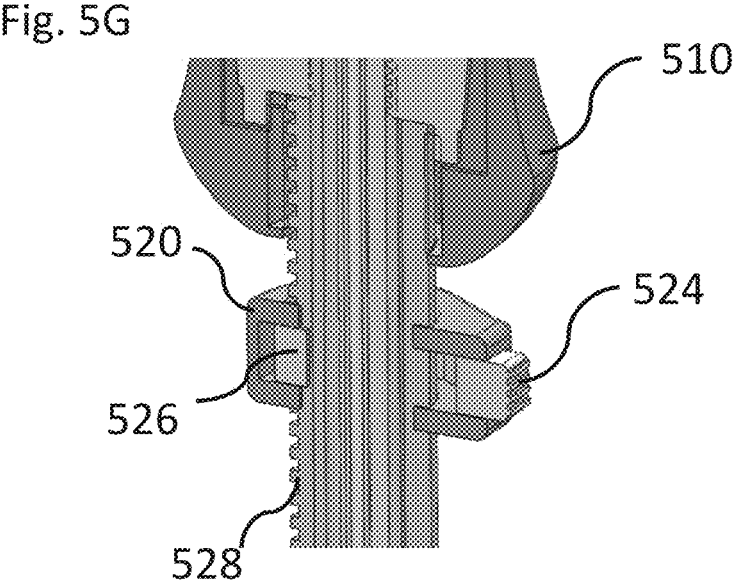

Reference is now made to FIGS. 5E-5G depicting the adjustment of a stopper position, according to some exemplary embodiments of the invention.

According to some exemplary embodiments, a stopper 520 is positioned in contact with or around a shaft, connecting the handle 510 and the control unit 502. Optionally the shaft is a tubular shaft, for example tubular shaft 522. In some embodiments, the stopper 520 comprises a stopper button, for example bulge 524 at least partly extending out from the stopper 520. In some embodiments, pressing bulge 524, optionally against a force applied by a spring within the stopper 520, moves away a protrusion 526 mechanically connected to the button 524 from a slit on the outer surface of the tubular shaft 522, for example slit 528. In some embodiments, when the button 524 is in a relaxed state, the protrusion 526 mechanically interferes with the slit on the outer surface of the tubular shaft 522.

According to some exemplary embodiments, deactivating a mechanical interference between the stopper 520 and the tubular shaft 522 allows, for example axially sliding of the stopper 520 along the tubular shaft 522, for example as shown in FIG. 5F. In some embodiments, the stopper 520 is moved along the tubular shaft 522 according to a measured distance between a sampling portion of the shaft located at the distal end of the shaft, and a target tissue, for example as described at 414 in FIG. 4A. Alternatively, the stopper 520 moves along the tubular shaft 522 according to a measured distance between the sampling portion of the shaft and a distal opening of the sleeve or a distal opening of an endoscope working channel.

According to some exemplary embodiments, when reaching a desired position according to the measured distance, the button 524 is released and the protrusion 526 mechanically interferes with a slit on the tubular shaft 528. In some embodiments, the stopper 520 limits the travelling distance of the shaft within the sleeve.

Figure 5H:
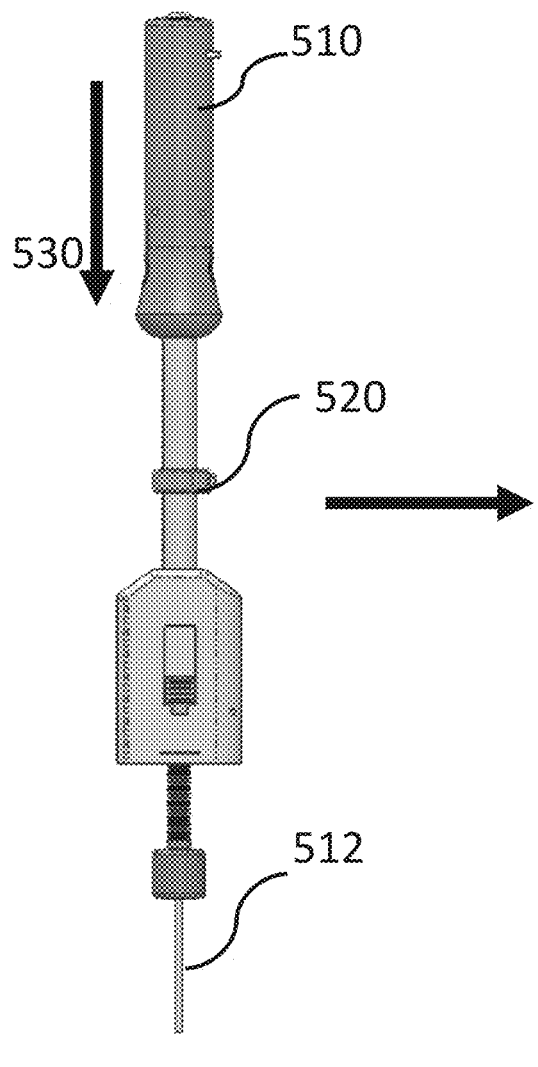
Figure 5I:
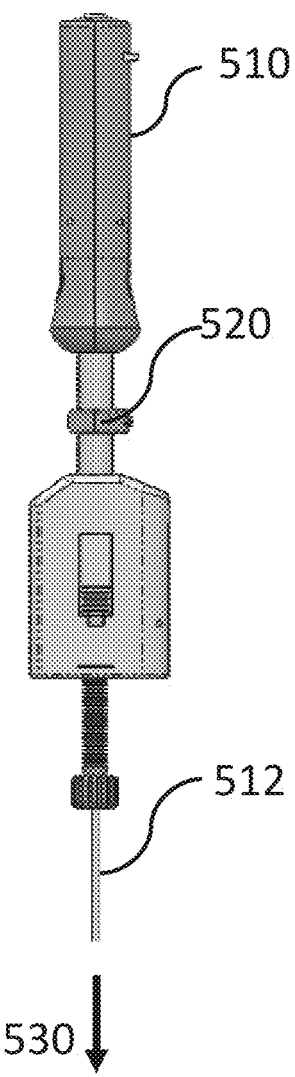
Figure 5J:
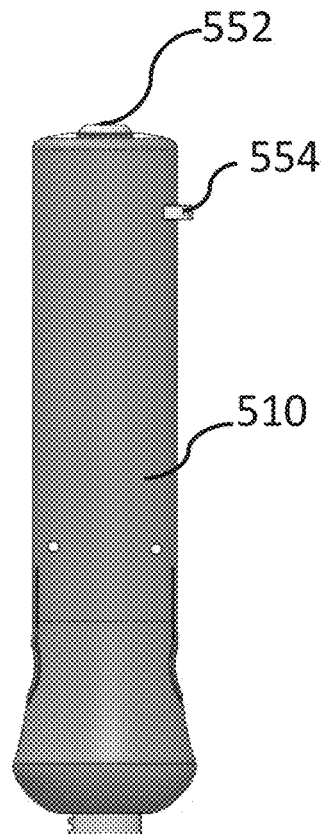
Figure 5K:
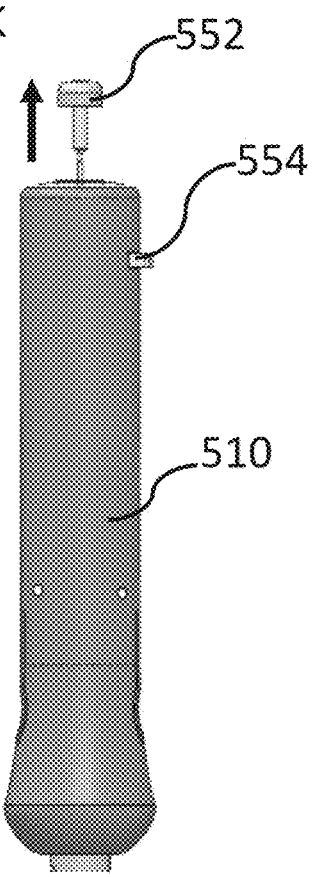
Figure 5L:
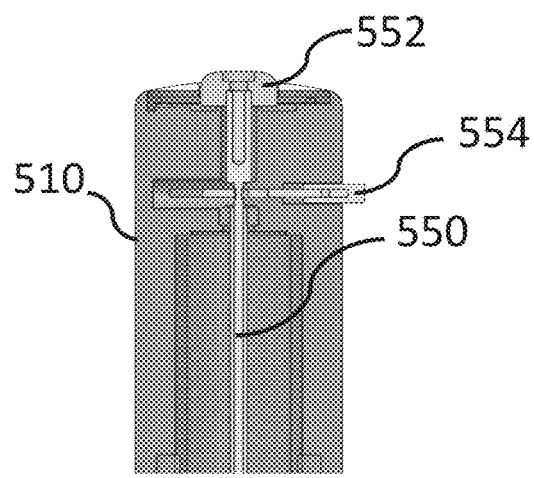
Figure 5M:
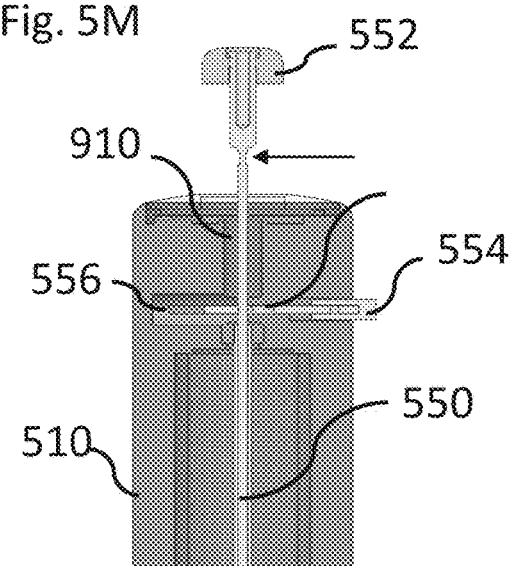

According to some exemplary embodiments, for example as shown in FIGS. 5H and 5I, the shaft is advanced within the sleeve 512 towards a target tissue, for example by moving handle 510 in direction 530 towards stopper 520. In some embodiments, the shaft advances until the sampling portion at the distal end of the shaft, for example sampling portion 450 shown in FIG. 4B is positioned at a desired distance from an essential organ or tissue, for example blood vessel.

According to some exemplary embodiments, for example as shown in FIGS. 5J-5M, a stylet, for example stylet 550 is retracted prior to sampling the target tissue. Optionally, the stylet 550 is retracted prior to insertion of the sampling portion of the shaft into the target tissue. In some embodiments, the stylet is retracted at least 30 mm, for example 30 mm, 40 mm, 50 mm, 100 mm or any intermediate, smaller or larger value. In some embodiments, the stylet is retracted by pulling a button 552 mechanically connected to the stylet 550. In some embodiments, the button 552 is pulled when a pressure applied by a pin, for example pin 554, on the stylet 550 is relieved. In some embodiments, when pin 554 is moved and optionally disconnects from the stylet 550 the stylet 550 can be moved. In some embodiments, the stylet is automatically or at least partly manually axially retracted by pushing the sampling button, for example activation button 560, optionally against a retracting force, for example applied by a spring which forces the retraction of the stylet. Alternatively or optionally, if the stylet is in a distal position it disables the activation of the sampling by a mechanical mechanism or by a sensor connected to the control unit.

According to some exemplary embodiments, when the pin 554 is in a resting state, a spring, for example spring 556 within handle 510, pushes the pin against the stylet. Optionally, when the stylet 550 is retracted to a desired distance, the pin 554 is released and is pushed against the stylet 550, for example to prevent the return of the stylet to a previous position prior to retraction. Optionally, when the stylet 550 is retracted to a desired distance, the stylet rotates around its axis for example to prevent the return of the stylet to a previous position prior to retraction. Optionally, the stylet is retracted, to release a locking mechanism preventing the forward advancement of the stylet.

According to some exemplary embodiments, for example as shown in FIGS. 5N-5P, the shaft is rotated while rotating and axially advancing the sampling portion of the shaft into the target tissue. In some embodiments, pushing at least one activating button comprised in the handle 510, for example button 560 shown also in FIGS. 5E and 5F, activates a motor to rotate the shaft in at least 100 RPM. Alternatively, pushing the at least one button engages the motor to the shaft through a gear unit. In some embodiments, the motor axially advances the sampling portion of the shaft into the target tissue. Alternatively, the axially advancement of the sampling portion is performed manually.

According to some exemplary embodiments, when the sampling portion axially advances into the shaft, the handle 510 axially advances in the same direction and optionally in a similar ratio to the advancement of the sampling portion. Alternatively, the handle axially advances in the same direction as the sampling portion but in a different ratio from the advancement of the sampling portion. In some embodiments, when the handle axially moves in a similar ratio to the axially advancement of the sampling portion, the travelling distance of the handle is similar to the travelling distance of the sampling. Optionally when the ratio is similar, a user of the device, for example an expert optionally a technician or a physician, receives a sensory and/or visual indication of the sampling portion travelling distance by sensing and/or visualizing the travelling distance of the handle. In some embodiments, the sensory indication is important in procedures when the user eye-sight is focused on an imaging screen (e.g. ultrasound, fluoroscopy or other)

According to some exemplary embodiments, the sampling portion axially advances into the target tissue by axially advancing the handle 510, optionally manually, towards the stopper 520. In some embodiments, the stopper

520 limits the axial advancement of the sampling portion within the target tissue to a selected and optionally predetermined sampling depth.

According to some exemplary embodiments, for example as shown in FIG. 5P, when reaching the desired sampling depth, the sampling portion is retracted from the target tissue, for example by retracting the handle away from the stopper 520. Optionally, when retracting the sampling portion out from the target tissue, the rotation of the sampling portion is stopped, for example to reduce friction with the surrounding tissue. In some embodiments, the motor is stopped or disengaged from the shaft by pressing the button 560 or pressing a different button in the handle. In some embodiments, the position and/or the angle of the sampling portion relative to the target tissue is changed, for example to allow sampling of a different region in the target tissue. In some embodiments, when the position and/or the angle of the sampling portion is changed, the sampling portion is advanced again into the target tissue, as described above.

Figure 5R:
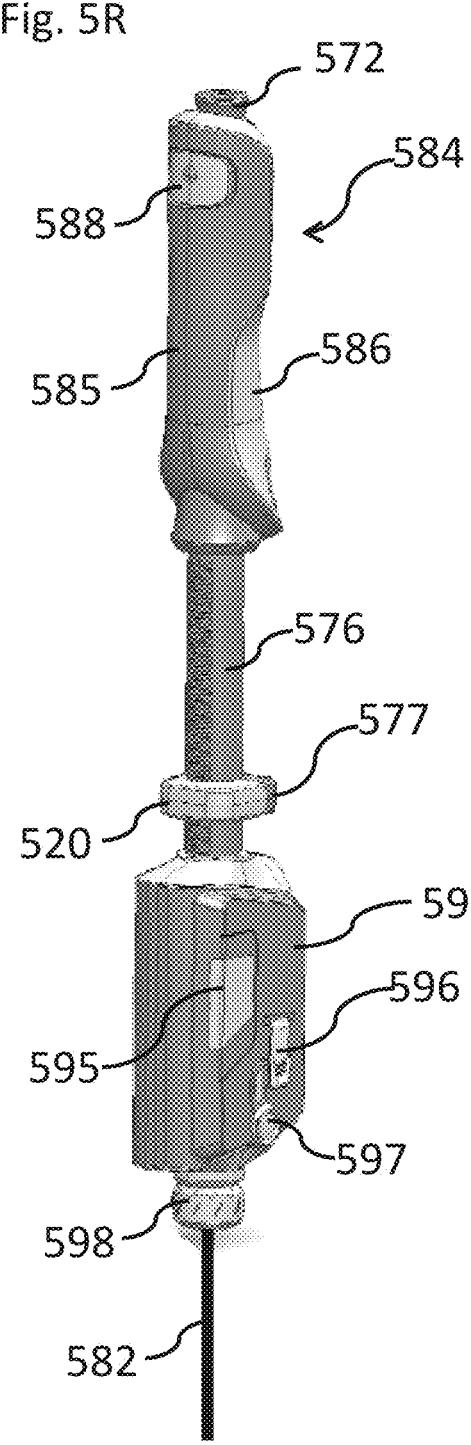
Figure 5S:
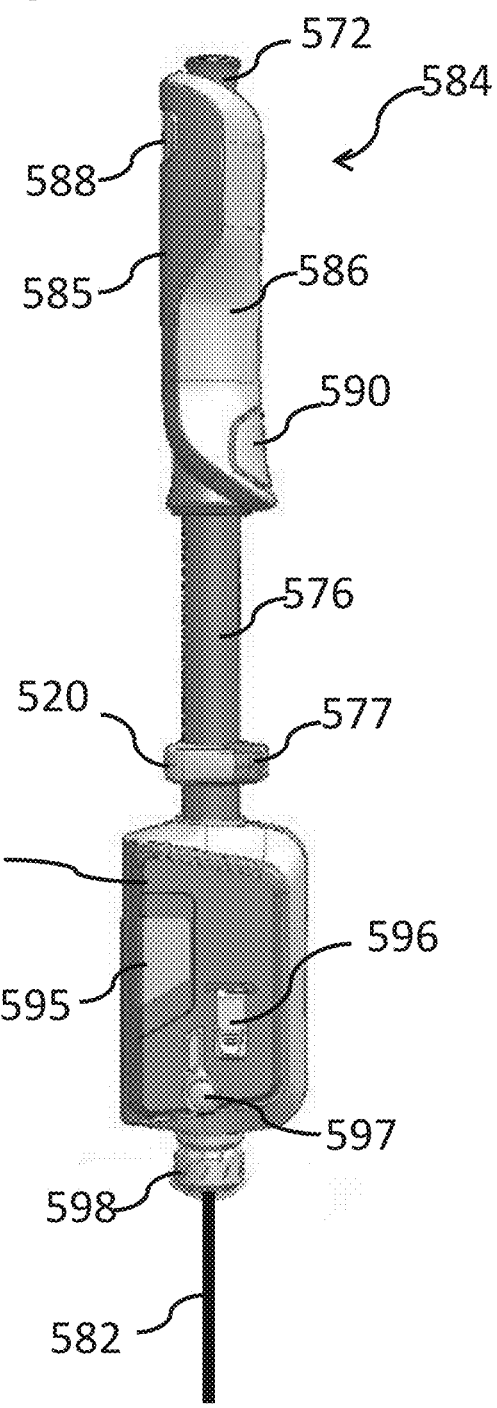

Reference is now made to FIGS. 5Q-5S depicting biopsy sampling devices having a control unit with a user interface, according to some exemplary embodiments of the invention.

According to some exemplary embodiments, a biopsy sampling device, for example sampling devices 570 shown in FIG. 5Q and sampling device 584 shown in FIGS. 5R-5S are configured to be used with an endoscope, for example an ultrasound endoscope for fine needle biopsy (FNB) of body tissues. Optionally, the body tissues are located within or adjacent to the gastrointestinal tract. In some embodiments, the body tissues comprise one or more of submucosal lesions, mediastinal masses, lymph nodes and/or intraperitoneal masses, within or adjacent to the gastrointestinal tract.

According to some exemplary embodiments, the biopsy sampling device is part of an endoscopic ultrasound-guided fine needle biopsy system, which comprises and controls an echogenic sampling portion, for example a biopsy needle used through an instrument channel of an ultrasound imaging endoscope. In some embodiments, the system is used to sample targeted sub☐mucosal and extramural gastrointestinal lesions through an accessory channel of an ultrasound endoscope by the needle rotation around its axis.

According to some exemplary embodiments, the sampling device is battery operated (internally powered), for example to allow physician-controlled sampling at a designated site. Alternatively, the sampling device is electrically connected to an external electrical source. Optionally, the sampling device comprises at least one preloaded energy source, for example a preloaded mechanical energy source. Optionally, the preloaded mechanical energy source comprises a spring.

According to some exemplary embodiments, the sampling device comprises a handle, for example handles 571 or 585. In some embodiments, the handle is shaped and sized to be held by a single hand of a user. Optionally, for example as shown in handle 585, the handle comprises a gripping area, for example an indented gripping area 585. In some embodiments, the gripping area is shaped and sized to fit at least part of a hand, for example the palm of the hand and/or one or more fingers.

According to some exemplary embodiments, the handle comprises a body and a cover, which include the device components. In some embodiments, the handle is made of a 3D printed Somos® XC WaterShed 11122. Optionally, the Somos® WaterShed XC 11122 allows the manufacturing of highly detailed parts with superior clarity and water resistance and/or durability. Alternatively or additionally, the handle and/or other parts of the sampling device are made using polymer injection, for example plastic injection, into molds or templates. In some embodiments, the handle controls the axial advancement of the needle in relation to the base and the stem.

According to some exemplary embodiments, the sampling device comprises a stylet passing through the handle. In some embodiments, a proximal end of the stylet is connected to a stylet knob 572, for example button 552 shown in FIGS. 5J-5O. In some embodiments, the stylet knob 572 is positioned within the handle, for example when the stylet is located at a most distal location within the needle. Alternatively, the stylet knob 572 is pushed out from the handle, for example handle 571 or handle 585. In some embodiments, the stylet knob 572 is pushed out from the handle when the stylet is retracted at least partly out from a sampling portion of the device, for example a sampling needle.

According to some exemplary embodiments, the handle, for example handle 585 comprises a gripping member, shaped and sized to be gripped by a portion of a hand, for example the palm of the hand.

According to some exemplary embodiments, the sampling device comprises a stylet control button, for example to control the axial and/or rotational movement of the stylet. In some embodiments, the stylet control button, for example a stylet release button 573 or stylet release button 588 is located in the handle. For example, the stylet release button 572 is located in handle 572, and stylet release button 588 is located in handle 585. In some embodiments, the stylet control button is located near an upper or proximal section of the handle, optionally near the stylet knob 572.

According to some embodiments, the stylet release button is pressed, for example, to enable the retraction of the stylet from at least part of the needle lumen. In some embodiments, clearing the needle lumen, allows tissue to penetrate into the lumen. In some embodiments, the stylet release button is used as a safety mechanism, for example to prevent an unintended ejection of the sample by locking the stylet in a retracted position.

According to some exemplary embodiments, the stylet knob 572 is pressed, for example to forward the stylet into the needle and to push a sampled tissue portion outside from the needle, for example into an external sample container.

According to some exemplary embodiments, the sampling device comprise an activation button, for example a sampling button 560 located in handle 571 or sampling button 590 located in handle 585. In some embodiments, pressing the sampling button or turning the button to an activation mode, initiates the sampling process for example by advancing and rotating the needle.

According to some exemplary embodiments, the handle is connected to a shaft, for example shaft 576 or tubular shaft 522. In some embodiments, the shaft is an elongated shaft, optionally a tubular shaft. In some embodiments, a stopper lock, for example stopper 520 positioned around shaft 576. In some embodiments, the stopper lock moves along the shaft 576, for example to adjust the puncturing or penetration depth of the needle. In some embodiments, the stopper lock is an interference stopper lock.

According to some exemplary embodiments, the stopper lock comprises a stopper button, for example stopper button 577. In some embodiments, pressing and/or turning the stopper button 577 allows for example, to release the stopper lock and allows the movement of the stopper lock. In some embodiments, release of the stopper button 577 locks the stopper lock 520 at a selected axial position along the shaft 576. In some embodiments, the selected position determines the needle penetration depth for example into a target tissue during the sampling process.

According to some exemplary embodiments, the sampling device comprises a control unit, connected to a proximal end of the shaft. In some embodiments, for example control unit 575 of sampling device 570, is connected to a distal end of shaft 576 located away from the handle 571. In some embodiments, the control unit comprises an interface, for example interface 578. In some embodiments, the interface is configured to deliver an indicator or an alert signal to a user related to the operation of the sampling device.

In some embodiments, the interface 578 comprises a display, for example an LCD display. Alternatively or additionally, the interface 578 comprises one or more indicators, for example LED light indicators. In some embodiments, the LED light indicators, are color indicators, and are configured to deliver an indication related to the operation of the device. In some embodiments, each LED light indicates a different status of the device, for example a green light indicates that the device is in a standby status, a blinking green light indicates that the device is in a sampling status, a blinking yellow light indicates a caution status, a red light indicates the completion of the device lifespan, a blinking red signal indicates warning. Optionally, the interface 578 comprises at least one audio generator, for example a speaker or a vibrator configured to generate human detectable vibrations.

According to some exemplary embodiments, the control unit, for example the control unit 575 comprises a sheath length adjuster lock, for example sheath length adjuster lock 579. In some embodiments, the sheath length adjuster lock 579 locks a sheath length adjuster, for example adjuster 580. In some embodiments, the sheath length adjuster, for example adjuster 580 is a rotatable component that upon manipulation, allows adjustment of the Sheath length.

According to some exemplary embodiments, the sheath length adjuster lock 579 is configured to lock the adjuster 580 in an axial direction. Optionally, the sheath length adjuster lock is configured not to lock the adjuster 580 in a circumferential direction, for example to allow rotation of the adjuster 580 and sheath 582 in a circumferential direction relative to a working channel of the endoscope.

According to some exemplary embodiments, control unit 594 of the sampling device 584 shown in FIGS. 5R and 5S comprise a window 595 located at the external surface of the control unit cover. In some embodiments, the window 595, for example a transparent window, is shaped and sized to allow visualization of a display or one or more indicators, for example LED light indicators positioned inside the control unit 594. Optionally, the display, for example an LCD display and/or the LED light indicators are positioned underneath the window 595.

According to some exemplary embodiments, the control unit 594 of the sampling device 584 comprises a sheath length adjuster lock 597. In some embodiments, the sheath length adjuster lock 597 is a lever lock. In some embodiments, the sheath length adjuster lock 597 locks a sheath length adjuster, for example adjuster 598. In some embodiments, the sheath length adjuster, for example adjuster 598 is a rotatable component that upon manipulation, allows adjustment of the sheath length.

According to some exemplary embodiments, the sheath length adjuster lock 597 is configured to lock the adjuster 598 in an axial direction. Optionally, the sheath length adjuster lock 597 is configured not to lock the adjuster 598 in a circumferential direction, for example to allow rotation of the adjuster 598 and sheath 582 in a circumferential direction relative to a working channel of the endoscope.

According to some exemplary embodiments, the control unit, for example control unit 594 comprises at least one battery for operating the sampling device. In some embodiments, a latch 596 extending at least partly out from the control unit 594 separates between the electrical connections of the at least one battery and an electrical circuitry of the sampling device located within the control unit. In some embodiments, removing or pulling the latch allows electrical connection between the at least one battery and the electrical circuitry of the sampling device.

According to some exemplary embodiments, the handle, for example handle 585 is shaped and sized to be held and optionally functionally activated by a single hand of a user.

Examplying Sampling Portion of a Biopsy Device

According to some exemplary embodiments, a sampling portion, for example sampling portion is a hollow section located at the distal end of a shaft facing a target tissue, shaped and sized for sampling the tissue. In some embodiments, the sampling portion is a hollow needle, optionally a replaceable needle. In some embodiments, the sampling portion length is in a range of 0-300 mm, for example 30 mm, 50 mm, 80 mm, 100 mm or any intermediate, smaller or larger value. In some embodiments, the sampling portion is a hollow cylindrical sampling portion with an outer diameter in a range of 0.5-5 mm, for example 0.5 mm, 1 mm, 2 mm, 2.5 mm 3 mm or any intermediate, smaller or larger value. In some embodiments, the sampling portion comprises and/or outer sharpening. In some embodiments, at least part of the internal surface inner sharpening and/or the outer surface of the sampling portion is sharpened, for example to allow cutting of the target tissue.

Figure 6A:
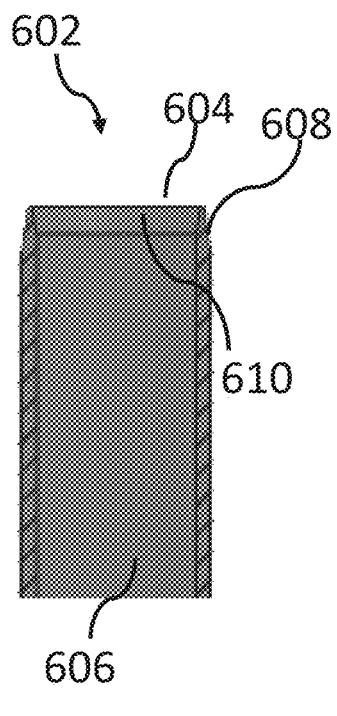
FIGS. 6A-6N are schematic illustrations of a sampling portion of a hollow shaft, according to some embodiments of the invention.

Reference is now made to FIG. 6A depicting a sampling portion of a biopsy device with a circumferential sharpened section, according to some exemplary embodiments of the invention.

According to some exemplary embodiments, sampling portion 602 is a cylindrical hollow sampling portion comprises a distal opening 604 and an internal lumen 606. In some embodiments, the outer diameter of the sampling portion 602 is 0.5-5 mm, for example 0.6 mm, 0.7 mm, 0.72 mm, 1 mm or any intermediate, smaller or larger value. In some embodiments, the sampling portion 602 has an internal diameter in a range of 0.3-4 mm, for example 0.5 mm, 0.6 mm, 0.9 mm or any intermediate, smaller or larger value. In some embodiments, the sampling portion 602 has a circumferential tapered outer surface 608, optionally an outer sharpening surface surrounding the distal opening 604. In some embodiments, the circumferential tapered outer surface 608 is shaped and sized for cutting a circular portion of the target tissue, for example when the sampling portion 602 penetrates into the target tissue. In some embodiments, sampling portion 602 comprises a circumferential internal sharpening surface 610, shaped and sized for cutting, for example a sample of the target tissue positioned within the lumen 606.

Figure 6B:
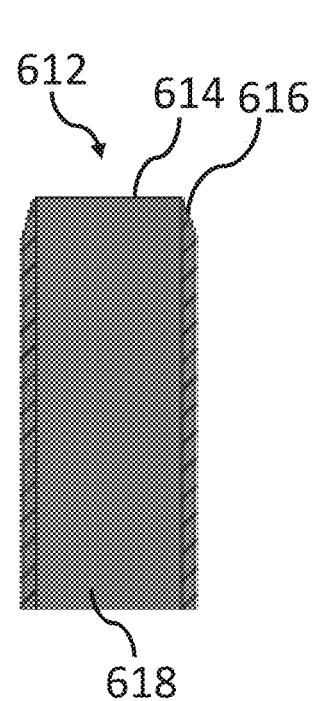

According to some exemplary embodiments, for example as shown in FIG. 6B sampling portion 612 is a cylindrical hollow sampling portion comprising a distal opening 614 and an internal lumen 618. In some embodiments, the outer diameter of the sampling portion 612 is 0.5-5 mm, for example 0.6 mm, 0.7 mm, 0.72 mm, 1 mm or any intermediate, smaller or larger value. In some embodiments, the sampling portion 612 has an internal diameter in a range of 0.3-4 mm, for example 0.5 mm, 0.6 mm, 0.9 mm or any intermediate or smaller value. In some embodiments, the sampling portion 612 has a circumferential tapered outer surface 616, optionally an outer sharpening surface surrounding the distal opening 614. In some embodiments, the circumferential tapered outer surface 616 is shaped and sized for cutting a circular portion of the target tissue, for example when the sampling portion 612 penetrates into the target tissue.

Figure 6C:
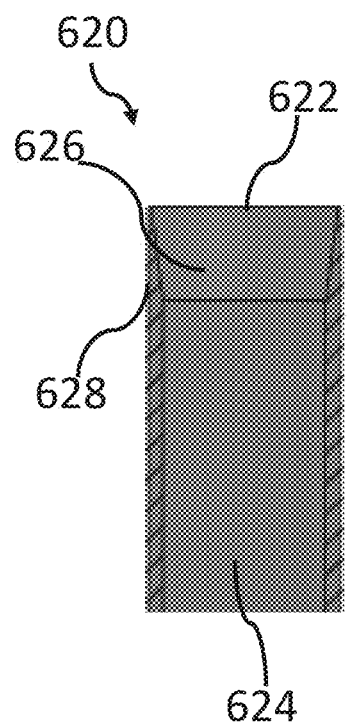

According to some exemplary embodiments, for example as shown in FIG. 6C sampling portion 620 is a cylindrical hollow sampling portion comprising a distal opening 622 and an internal lumen 624. In some embodiments, the outer diameter of the sampling portion 620 is in a range of 0.5-5 mm, for example 0.6 mm, 0.7 mm, 0.72 mm, 1 mm or any intermediate, smaller or larger value. In Some embodiments, the distal opening 622 of the sampling portion 620 has a diameter is in a range of 0.5-5 mm, for example 0.6 mm, 0.7 mm, 0.72 mm, 1 mm or any intermediate, smaller or larger value. In some embodiments, the internal diameter of the sampling is smaller than the distal opening diameter, for example to compress tissue within the lumen 624. In some embodiments, an internal diameter smaller than an opening diameter increases friction forces applied by the internal surface of the sampling portion 620 on a tissue positioned within the lumen 624, for example to increase gripping of the tissue. In some embodiments, the sampling portion 620 has an internal diameter in a range of 0.4-4 mm, for example 0.5 mm, 0.6 mm, 0.9 mm or any intermediate or smaller value. In some embodiments, sampling portion 620 comprises a circumferential internal sharpening surface 626, shaped and sized for cutting, for example a sample of the target tissue positioned within the lumen 624.

Figure 6D:
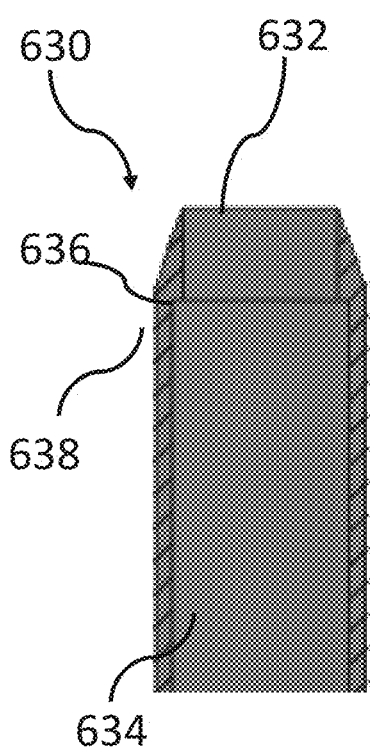

According to some exemplary embodiments, for example as shown in FIG. 6D sampling portion 630 is a cylindrical hollow sampling portion comprising a distal opening 632 and an internal lumen 634. In some embodiments, the outer diameter of the sampling portion 620 is in a range of 0.5-5 mm, for example 0.6 mm, 0.7 mm, 0.72 mm, 1 mm or any intermediate, smaller or larger value. In Some embodiments, the distal opening 622 of the sampling portion 620 has a diameter in a range of 0.3-4 mm, for example 0.3 mm, 0.5 mm, 0.72 mm, 0.8 mm or any intermediate, smaller or larger value. In some embodiments, the internal diameter of a distal section of the sampling portion closer to the distal opening, for example distal section 636 has the same diameter as the distal opening diameter. In some embodiments, the sampling portion comprises at least one step or gradation, for example stem 638, from a narrower section of the internal lumen to a wider section of the internal lumen. In some embodiments, the sampling portion 630 has an internal diameter in a range of 0.4-4 mm, for example 0.5 mm, 0.6 mm, 0.9 mm or any intermediate or smaller value. In some embodiments, the step or gradation is shaped and sized to hold a tissue sample positioned within the lumen 634, for example by blocking at least partly a passage towards the distal opening 632. In some embodiments, the distal section 636 comprises a circumferential internal sharpening surface, shaped and sized for cutting a sample of the target tissue entering through the distal opening 632 into the internal lumen of the sampling portion 630.

Figure 6E:
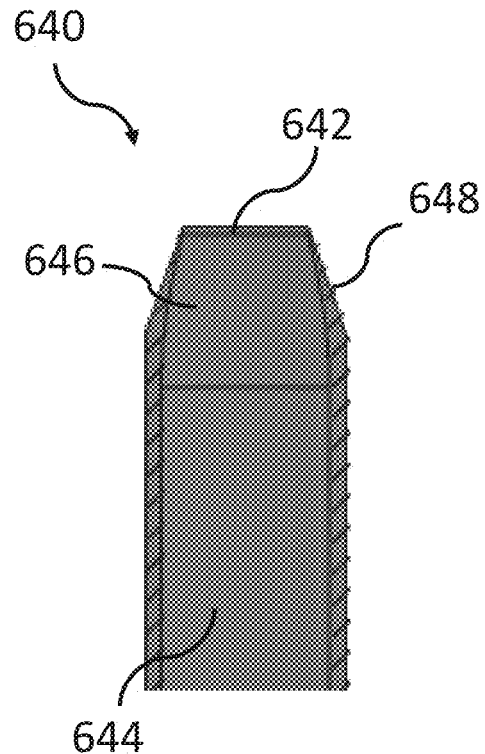

According to some exemplary embodiments, for example as shown in FIG. 6E sampling portion 640 is a cylindrical hollow sampling portion comprising a distal opening 642 and an internal lumen 644. In some embodiments, the outer diameter of the sampling portion 640 is in a range of 0.5-5 mm, for example 0.6 mm, 0.7 mm, 0.72 mm, 1 mm or any intermediate, smaller or larger value. In Some embodiments, the distal opening 642 of the sampling portion 640 has a diameter in a range of 0.2-1 mm, for example 0.3 mm, 0.5 mm, 0.72 mm, 0.8 mm or any intermediate, smaller or larger value. In some embodiments, the internal diameter of a distal section of the sampling portion closer to the distal opening, for example distal section 646 has a gradually increasing internal diameter, for example from the distal opening diameter value to an internal diameter in a range of 0.5-2 mm, for example 0.5 mm, 0.6 mm, 0.9 mm or any intermediate or smaller value. In some embodiments, the gradual increase in internal diameter is shaped and sized to hold a tissue sample positioned within the lumen 634, for example by narrowing at least partly a passage towards the distal opening 632. In some embodiments, the distal section 646 comprises a circumferential internal sharpening surface, shaped and sized for cutting a sample of the target tissue entering through the distal opening 642 into the internal lumen of the sampling portion 640.

Figure 6F:
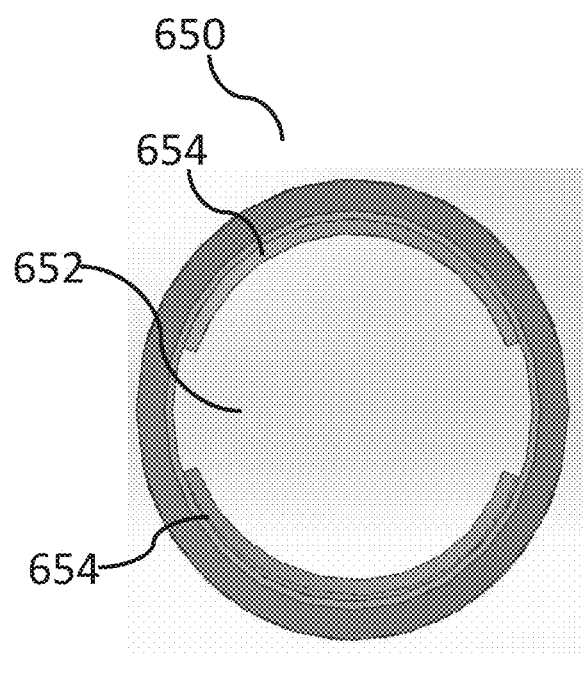
Figure 6G:
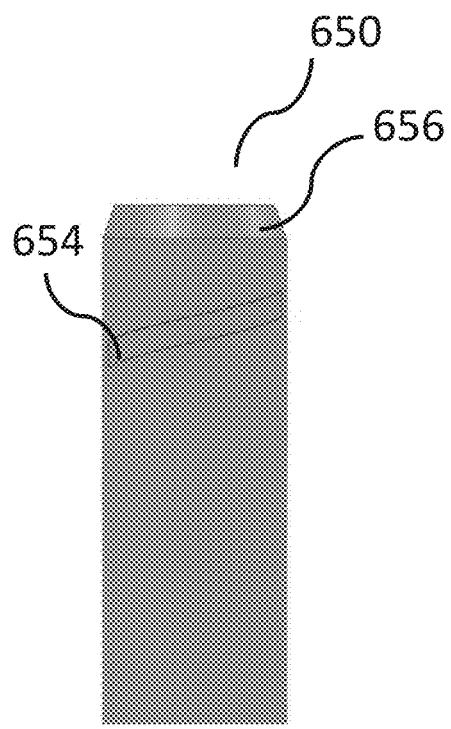
Figure 6H:
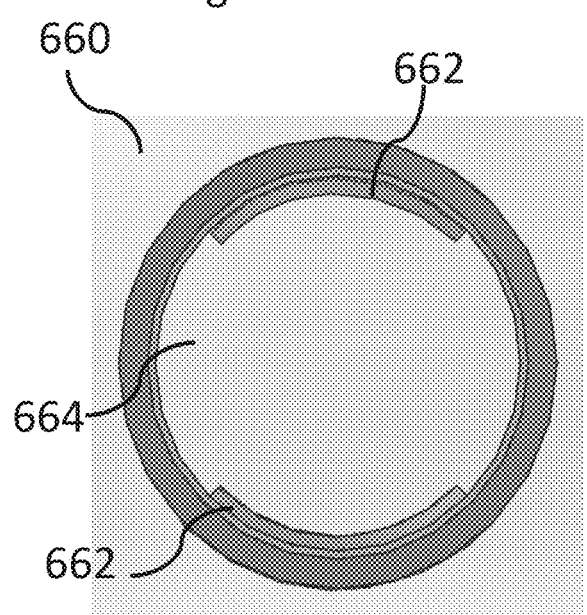
Figure 6I:
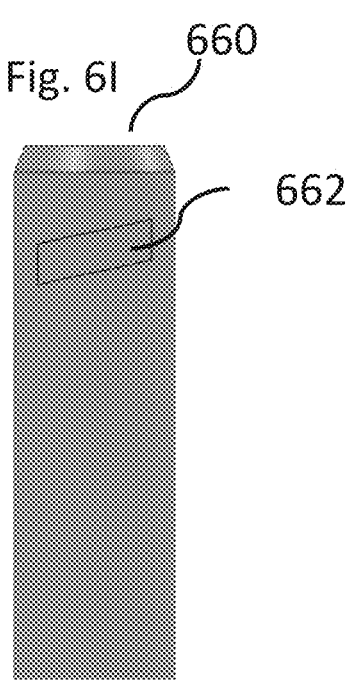

Reference is now made to FIGS. 6F-6N depicting sampling portions of a biopsy device with internal protrusions, according to some exemplary embodiments of the invention. According to some exemplary embodiments, for example as shown in FIGS. 6F and 6G, sampling portion 650 comprises an internal helical protrusion 654. Optionally the internal helical protrusion is at least partly circumferences the internal lumen 652 of the sampling portion 650. In some embodiments, for example as shown in FIGS. 6H and 6I, the sampling portion, for example sampling portion 660 comprises a wide internal helical protrusion 662, optionally at least partly surrounds the internal lumen 664 of the sampling portion 660. In some embodiments, the width of the internal helical protrusion is in a range of 0.03 mm to 1 mm, for example 0.05 mm, 0.08 mm. 0.1 mm, 0.5 mm or any intermediate, smaller or larger value.

Figure 6J:
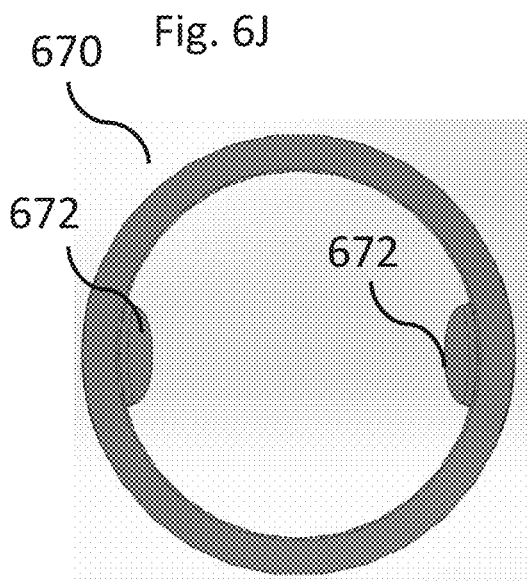
Figure 6K:
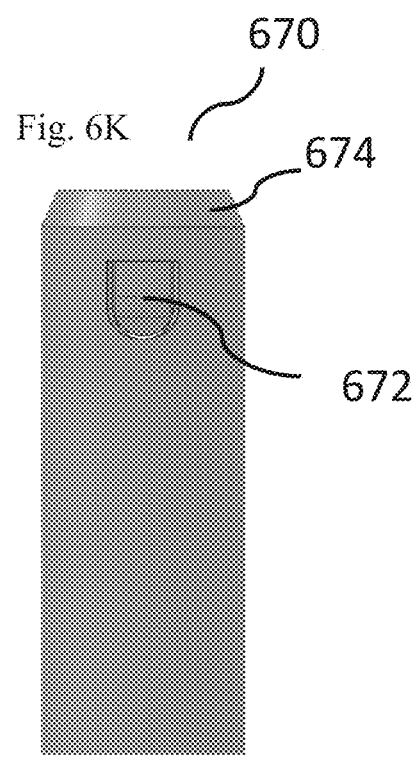
Figure 6L:
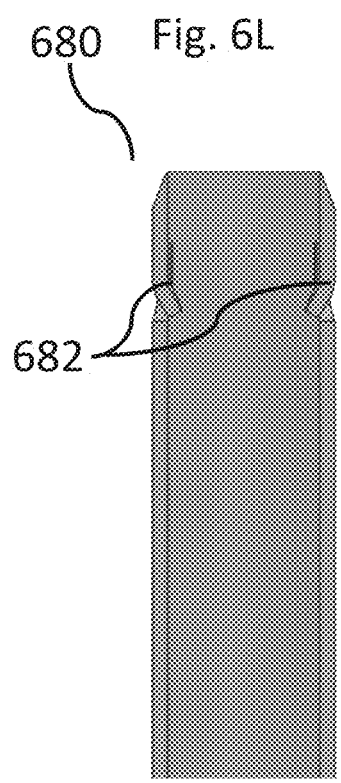
Figure 6M:
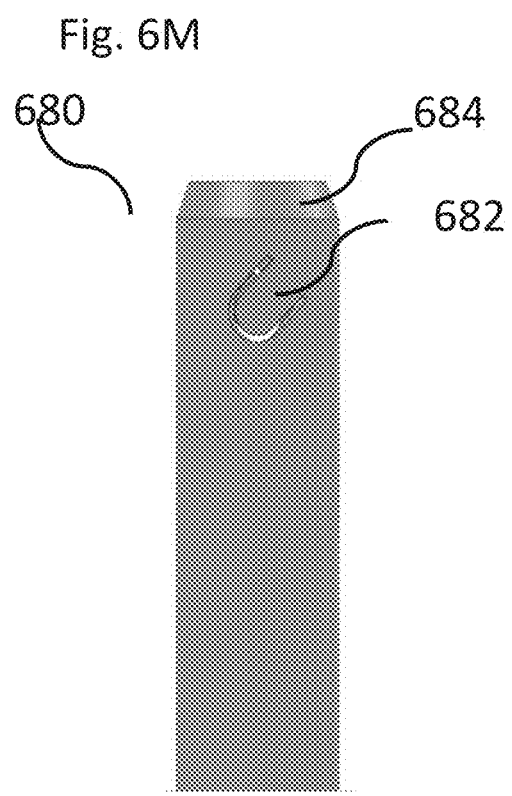
Figure 6N:
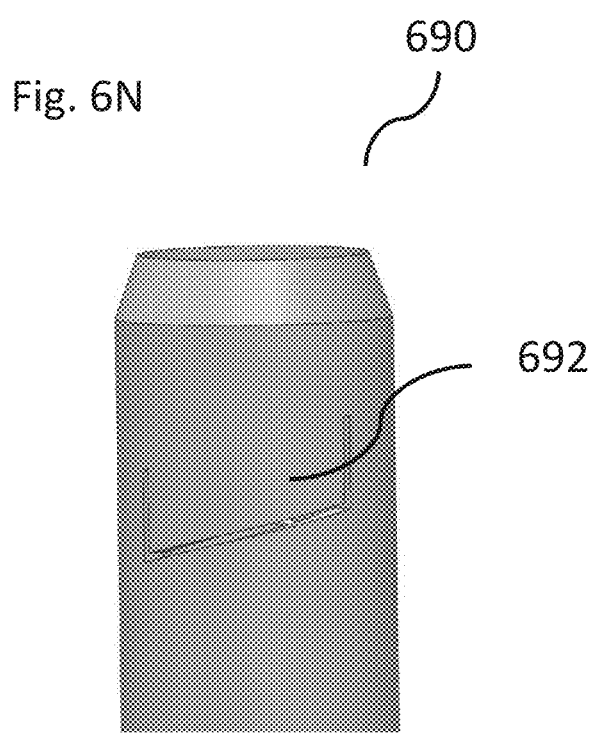

According to some exemplary embodiments, for example as shown in FIGS. 6J and 6K, the sampling portion, for example sampling portion 670 comprises at least one internal protrusion, for example protrusions 672 positioned on the internal surface of the sampling portion. In some embodiments, the protrusions are aligned along the long axis of the sampling portion, for example protrusions 672. Alternatively, the protrusions are placed at an angle relative the long axis of the sampling portion, for example protrusions 682 of sampling portion 680 shown in FIGS. 6L and 6M.

According to some exemplary embodiments, the protrusions are semi-circular or curved protrusions, for example protrusions 672 or 682. Alternatively, the protrusions are semi-rectangular protrusions, for example rectangular protrusion 692 of sampling portion 690.

Exemplary Sampling by Vacuum

According to some exemplary embodiments, an elongated shaft of a biopsy device is at least partly hollow and is connected to a pump or a syringe, optionally a vacuum pump. In some embodiments, the vacuum pump applies vacuum pressure to keep a sample tissue of the target tissue within a lumen of the shaft during a sampling process.

Figure 7:
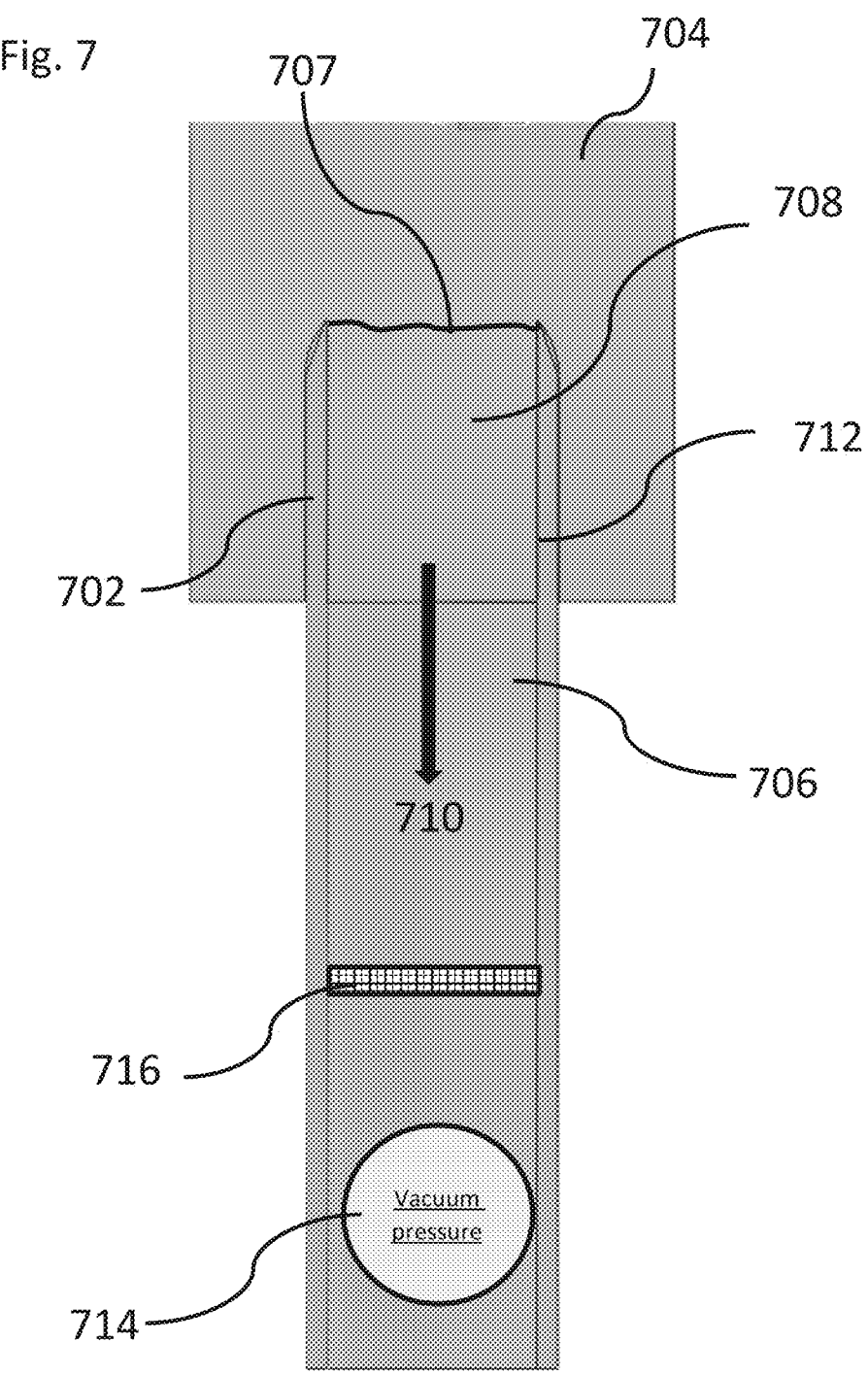
FIG. 7 is a schematic illustration of a biopsy device using suction force for tissue sampling, according to some embodiments of the invention.

Reference is now made to FIG. 7 depicting the use of vacuum pressure during a sampling process of a target tissue, according to some exemplary embodiments.

According to some exemplary embodiments, a sampling portion 702 of a biopsy device penetrates into a target tissue 704. In some embodiments, a circumferential external cutting edge 706, optionally a tapered cutting edge, surrounding a distal opening 707 of the sampling portion 702 cuts a section of the target tissue 704. In some embodiments, the tissue section 708 is pushed into a lumen 706 of the sampling portion as the sampling portion advances into the target tissue 704. In some embodiments, during the advancement of the sampling portion into the tissue, a vacuum pressure 714 is applied by a pump connected to the lumen, for example to force the tissue section 708 to enter into the lumen 706 in direction 710. Alternatively, the vacuum pressure 714 is applied when the sampling portion is retracted away from the target tissue 704, for example to keep the target tissue within the lumen 706 of the sampling portion 702. In some embodiments, the sampling portion comprises a filter 716 placed within the lumen 706, shaped and sized to prevent parts of the tissue section 708 to pass through the lumen of the shaft into the vacuum pump.

Exemplary Shaft

Figure 8A:
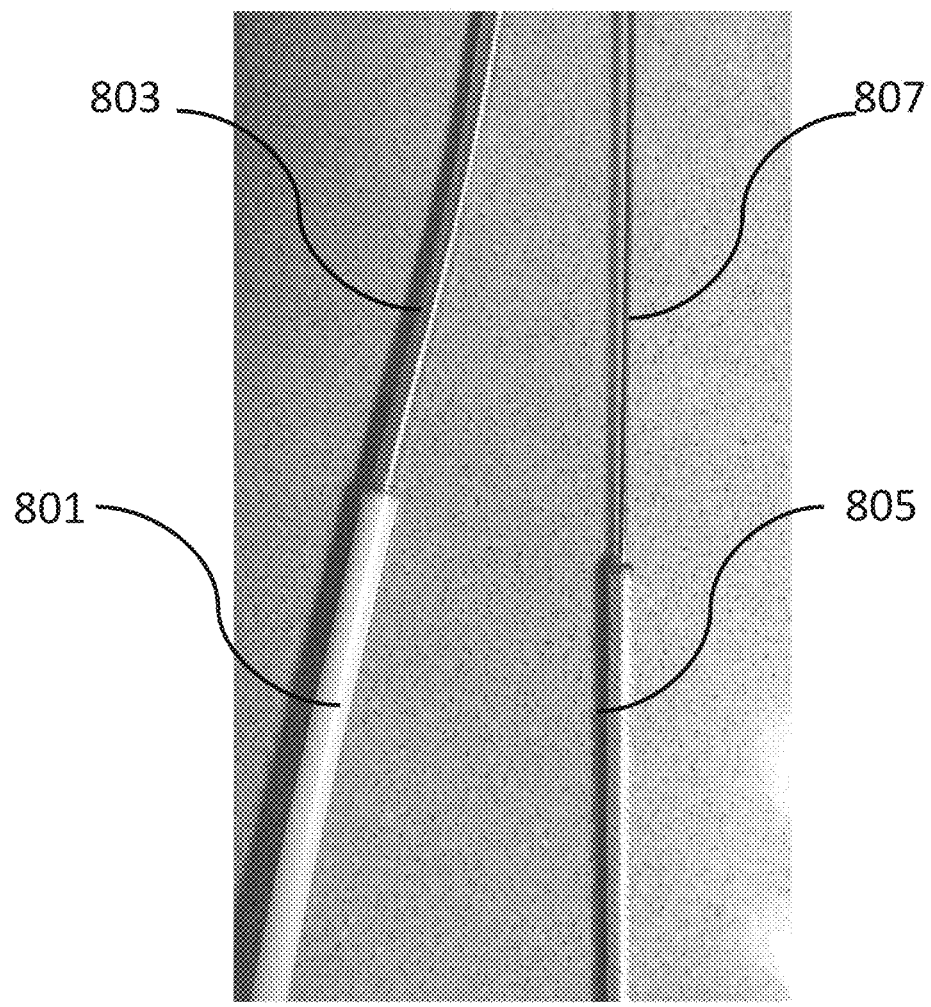
FIG. 8A is an image of a shaft within a sleeve of a biopsy device, according to some embodiments of the invention.

Reference is now made to FIG. 8A depicting a shaft of a biopsy device, according to some exemplary embodiments of the invention.

According to some exemplary embodiments, a shaft comprises a proximal section shaped and sized to allow delivery of high torque flexibility or range, and fatigue resistance and a distal section shaped and sized to allow torque transfer, and flexibility for example improved flexibility during angular adjustments of the shaft and/or sampling portion of the shaft, and/or fatigue resistance. Optionally, the distal section has a smaller diameter, for example to allow better penetration through the tissue. In some embodiments, the proximal section of the shaft comprises a sleeve 801 made of Polyether ether ketone (PEEK), and/or PEBAX and/or other materials and optionally coated with Polytetrafluoroethylene (PTFE), and/or HDPE and/or other materials for example to maintain stability and/or to reduce friction with surrounding tissue. In some embodiments, the distal section of the shaft comprises a spring 803 covered with a heat shrink, for example to allow optimal radius at the angular adjustment, for example elevation region, and to prevent damage to the surrounding tissue.

According to some exemplary embodiments, in the proximal section of the shaft, the shaft comprises a braided hollow cable 805, for example a Torque transmission cable, or a section that is formed from twisting one or more wires. In some embodiments, the torque transmission cable is an ActOne Braided and/or coiled cable. In some embodiments, the distal section of the shaft comprises a hollow tube 807, for example a Nitinol tube or a coiled hollow strand with a small diameter. Optionally, the hollow tube is a needle. In some embodiments, a sharp stylet passes within the shaft, for example to improve penetration characteristic, for example penetration through gastric or duodenum wall and/or through other tissues. Optionally, the stylet is also used to prevent the obstruction of the needle or contamination of the sample before reaching to the target tissue.

Exemplary Stylet

Figure 8B:
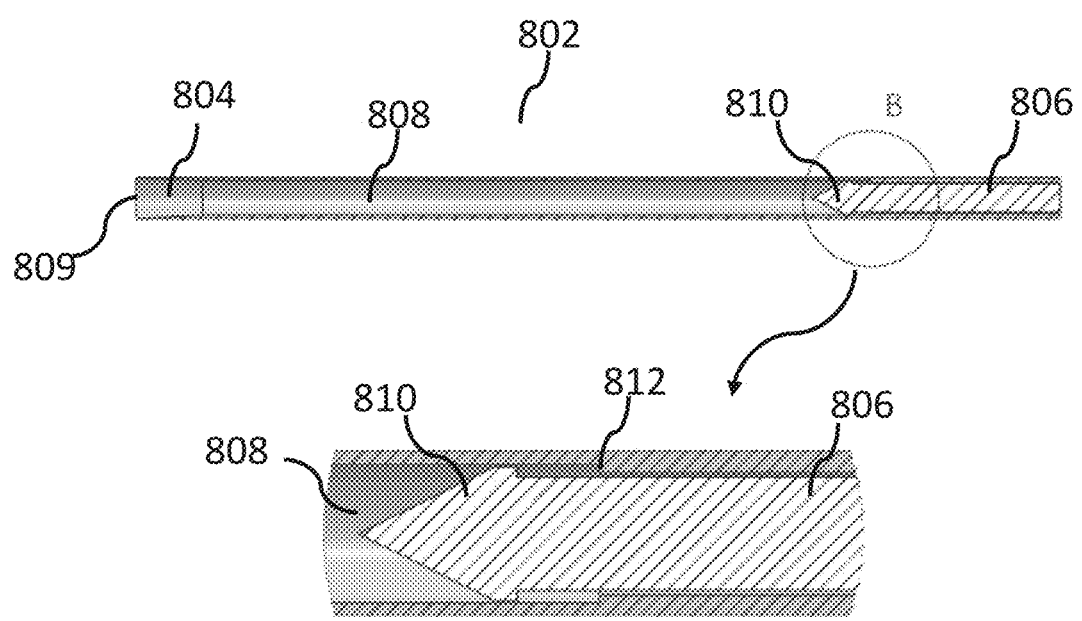
Figure 8C:
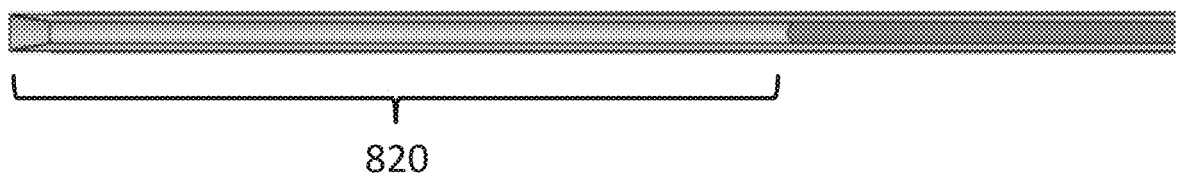

Reference is now made to FIGS. 8B and 8C depicting a stylet within a hollow shaft 802 of a biopsy device, according to some exemplary embodiments of the invention.

According to some exemplary embodiments, a flexible stylet 806 is movable within an axial internal lumen 808 of a shaft. In some embodiments, the stylet 806 comprises a distal end 810, optionally a sharpened distal end shaped and sized to penetrate through tissue when the distal end extends out from a distal opening 809 of the shaft. In some embodiments, the stylet is made from Nitinol or Stainless steel. In some embodiments, in order to sample a tissue, the stylet is retracted away from the distal opening 809, for example to allow tissue entry into the lumen 808.

According to some exemplary embodiments, the distal end 810 of the stylet 806 has a larger diameter than an inner diameter of a proximal section of the shaft 802. Alternatively, the shaft comprises at least one protrusion positioned with the lumen 808 at a distance from the distal opening 809, which narrows the lumen diameter to a diameter smaller than the diameter of the distal end 810 of the stylet. In some embodiments, the larger diameter of the distal end 810 of the stylet compared to the inner diameter of the shaft lumen limits the retraction distance of the stylet 806.

According to some exemplary embodiments, for example as shown in FIG. 8C, the stylet is retracted to a distance 820 in a range of 5-70 mm within the shaft, for example to a distance in a range of 5-40 mm, 10-50 mm, 25-70 mm or any intermediate, smaller or larger value or range of values. In some embodiments, the retraction distance is pre-determined. Alternatively, the retraction distance is selected by the user, for example according to the desired sample volume, tissue type, and/or desired number of samples. Alternatively, the style is static and the needle advancement make the room for the sample according to the needle advancement stroke. In some embodiments, the stylet is retracted when a stylet release button is pressed. Optionally, the stylet is retracted by activation of a pre-loaded energy source, for example a spring.

According to some exemplary embodiments, for example as shown in FIG. 8D, the stylet distal end 810 is conical, having a tip 811 facing the distal opening 809 of the shaft 806. Alternatively, the stylet distal end is sharpened in pyramid geometry in order to better cut through the tissue.

According to some exemplary embodiments, a distal end of the stylet comprises at least one flat surface, for example 2, 3, 4 or any larger number of flat surfaces. In some embodiments, one flat surface of the distal end of the stylet is a beveled edge. Optionally, the distal end of the stylet comprises at least one curved surface. In some embodiments, the at least one flat surface and/or the at least one curved surface are formed by sharpening the distal end of the stylet. Alternatively, the at least one flat surface and/or the at least one curved surface are formed by pressing the distal end of the stylet against a template or a mold of at least part of a desired shape.

Reference is now made to FIGS. 8E-8J depicting a distal end of a stylet having at least one flat surface, according to some exemplary embodiments of the invention. According to some exemplary embodiments, for example as shown in FIG. 8E, a distal end 820 of a stylet comprises at least one flat surface, for example flat surface 822. Additionally, the distal end 820 comprises at least one curved surface, for example curved surface 824. In some embodiments, for example as shown in FIG. 8F, a distal end of the stylet, for example distal end 826 comprises at least two flat surfaces, for example surfaces 828 and 830. Additionally, the distal end 826 comprises at least one curved surface, for example surface 832. In some embodiments, for example as shown in FIG. 8G, all of the surfaces of the distal end of the stylet, for example distal end 834 are flat surfaces, for example surfaces 836, 838, 840 and 842. In some embodiments, the surfaces have a similar surface area and/or have a similar angle relative to a longitudinal axis of the stylet. Alternatively, one or more of the surfaces have a different surface area and/or have a different angle relative to the longitudinal axis of the stylet, compared to other surfaces of the distal end.

Figure 8H:
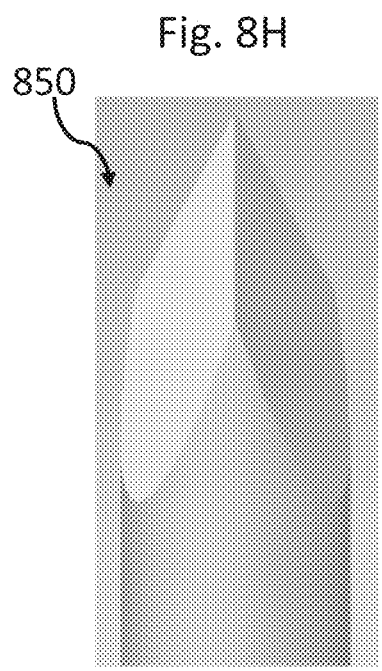
FIGS. 8H-8J are schematic side view illustrations of a distal end of a stylet having at least one flat surface, according to some embodiments of the invention.
Figure 8I:
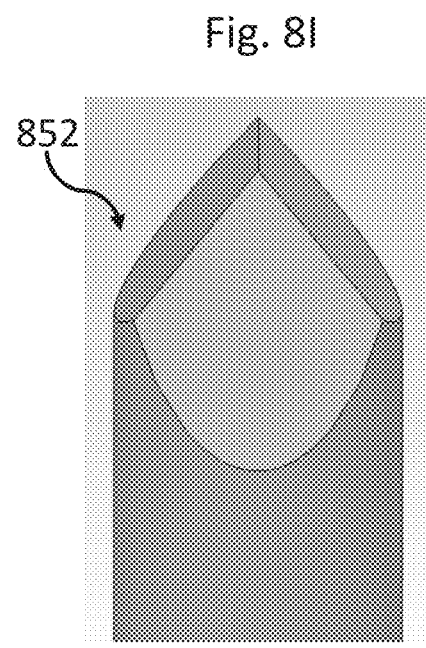
Figure 8J:
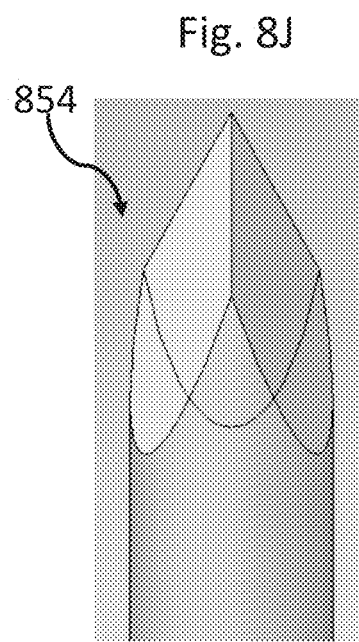

According to some exemplary embodiments, for example as shown in FIGS. 8H to 8J and as described in FIGS. 8E-8G, a distal end of a stylet, for example distal ends 850, 852 and 854 comprise at least one flat surface. Additionally or optionally, the distal end of the stylet comprises at least one curved surface.

Figure 8K:
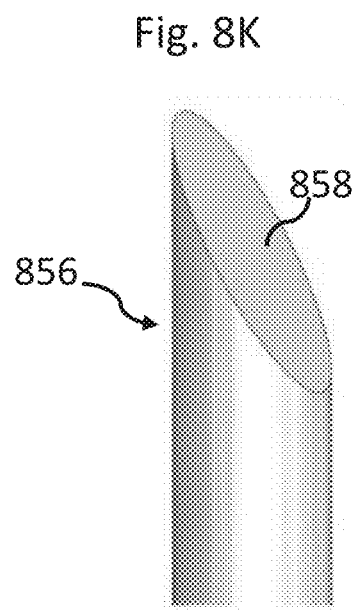
FIG. 8K is a schematic illustration of a distal end of a stylet comprising a beveled edge, according to some embodiments of the invention.

According to some exemplary embodiments, for example as shown in FIG. 8K, a distal end of a shaft, for example distal end 858 comprises at least one beveled edge, for example beveled edge 858.

According to some exemplary embodiments, when the shaft at least partly breaks at a sampling section, for example a needle and/or in a point between the narrowed shaft lumen or the protrusion and a proximal end of the shaft, the stylet is retracted, for example to retrieve the at least partly broken sampling portion, for example a needle into the biopsy device sleeve.

According to some exemplary embodiments, in order to allow retrieval of an at least partly broken sampling portion, for example a needle, back to the sleeve, the sampling portion is covered at least partly by a cover, for example a cover tube, a polymeric tube, a shrinked tube and/or any coating. In some embodiments, the cover allows to retract the at least partly broken sampling portion into the sleeve.

In some embodiments, the cover is braided from optionally round and/or flat wire made from stainless steel, steel, Nitinol, Cobalt, Chromium steel or any other material. Alternatively or additionally, the cover is made from compound material with fibers made of Aramid (e.g. Kevlar), Carbon, Glass or other fibers, optional flat fibers, in order to reduce the thickness of the cover layer.

Exemplary Control Unit

Figure 9A:
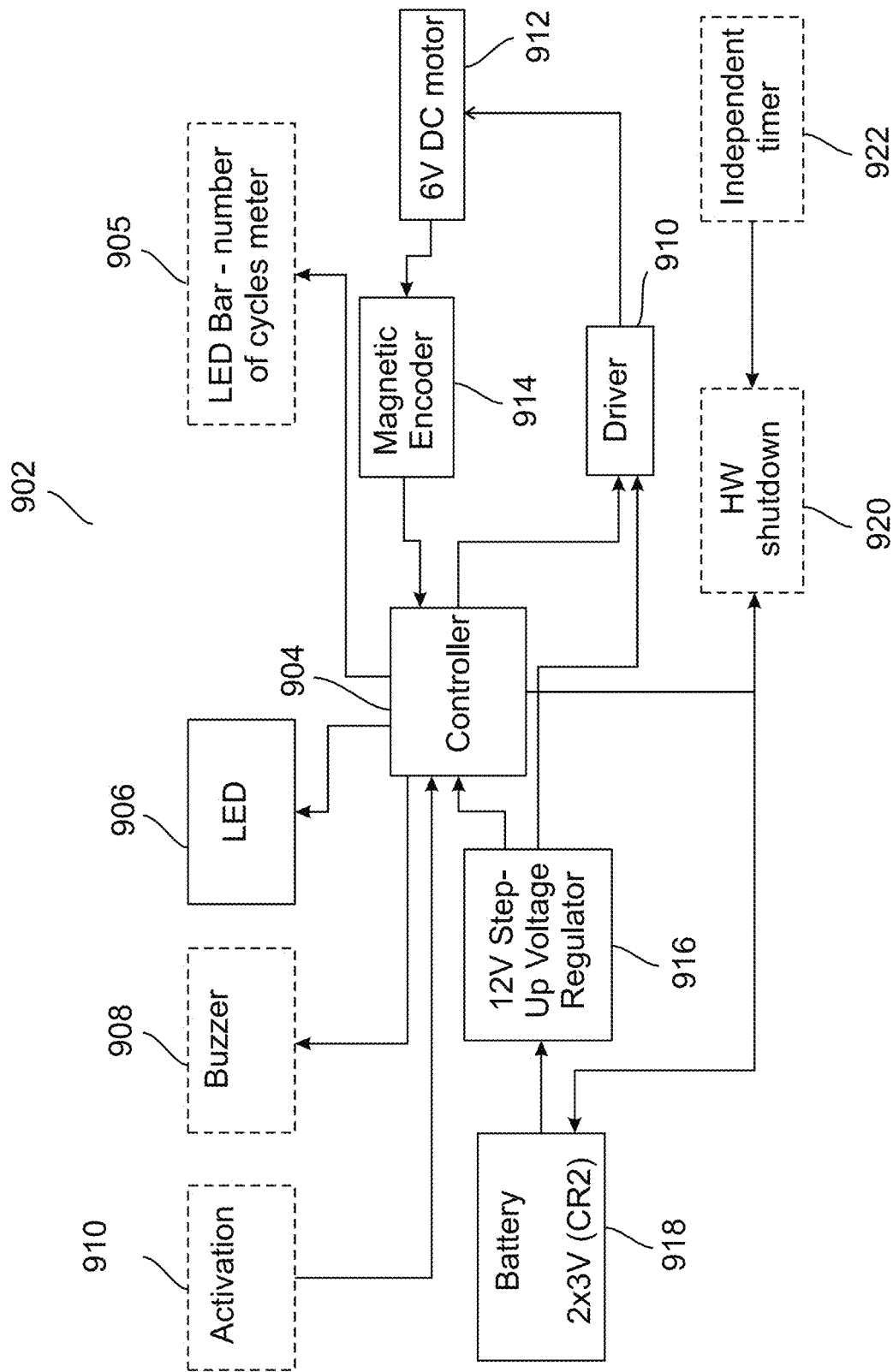
FIG. 9A is a block diagram of a control unit of a biopsy device, according to some embodiments of the invention.

According to some exemplary embodiments, a shaft comprising a sampling portion at the distal end of the shaft is connected to a control unit through the proximal end of the shaft. In some embodiments, the shaft is connected to a driving unit, optionally comprising a motor connected to a controller. In some embodiments, the controller controls the movement of the shaft by regulating the motor. Reference is now made to FIG. 9A depicting a control unit of a biopsy device, according to some exemplary embodiments of the invention.

According to some exemplary embodiments, a control unit 902 comprises a controller 904. In some embodiments, the controller is connected to a driver 910. In some embodiments, the driver 910 is connected to a motor 912, for example an electric motor. Optionally, the electric motor is a 6V DC motor. In some embodiments, the controller 904 controls at least one activation parameter of the motor 912, for example rotation duration, rotation speed and/or rotation direction by controlling driver 910.

According to some exemplary embodiments, the motor 912 is connected to a magnetic encoder 914, configured to measure one or more of rotation speed, rotation duration and/or rotation direction of the motor 912. In some embodiments, the controller 904 is connected to the magnetic encoder 914. In some embodiments, the controller 904 monitors the activation of the rotor based on signals received from the magnetic encoder 914.

According to some exemplary embodiments, the controller 904 is electrically connected to an activation circuit 910. In some embodiments, the activation circuit is configured to receive an activation command from a user of the biopsy device, optionally through an interface, for example an activation button or an activation selecting button. In some embodiments, when an activation command is received, the activation circuit 910 signals the controller 904 to activate the motor 912.

According to some exemplary embodiments, the control unit comprises an interface, configured to provide at least one human detectable indication electrically connected to the controller 904. In some embodiments, the interface is configured to deliver a human detectable sound indication, for example through a buzzer 908 connected to the controller 904. Alternatively or additionally, the interface is configured to deliver a human detectable visual indication, for example using a light emitting diode (LED) 906 connected to the controller 904. Optionally, the interface comprises and indicator for presenting the axial advancement and/or the rotation of the biopsy device, for example LED bar 905.

According to some exemplary embodiments, the control unit comprises at least one power source, for example a Battery 918, which is optionally a rechargeable battery and/or a replaceable battery. Optionally Battery 918 is a 2X3V (CR2) Battery. In some embodiments, the battery 918 is electrically connected to an electric regulator, for example a step-up voltage regulator, optionally a 12V step-up voltage regulator 916. In some embodiments, the voltage regulator is electrically connected to the driver 910 or to the motor 912. Alternatively, the Battery 918 is electrically connected directly to the driver 910 or to the motor 912.

According to some exemplary embodiments, the Battery 918 and/or the voltage regulator are connected to a hardware shutdown circuit, for example shutdown circuit 920 of the control unit 902. In some embodiments, the shutdown circuit 920 is configured to stop at least partly the operation of the biopsy device, for example by disconnecting the power source from the motor, and/or by signaling the controller to stop the operation of the motor or other elements in the control unit. In some embodiments, the shutdown circuit is electrically connected to a timer, for example an independent timer 922. In some embodiments, the timer is configured to set the activation duration of the biopsy device and/or the activation duration of the motor. Optionally, the timer signals the controller and/or the shutdown circuit to stop the operation of the motor and/or the operation of the biopsy device, when a pre-set operation time is over.

Exemplary Operation Program

Figure 9B:
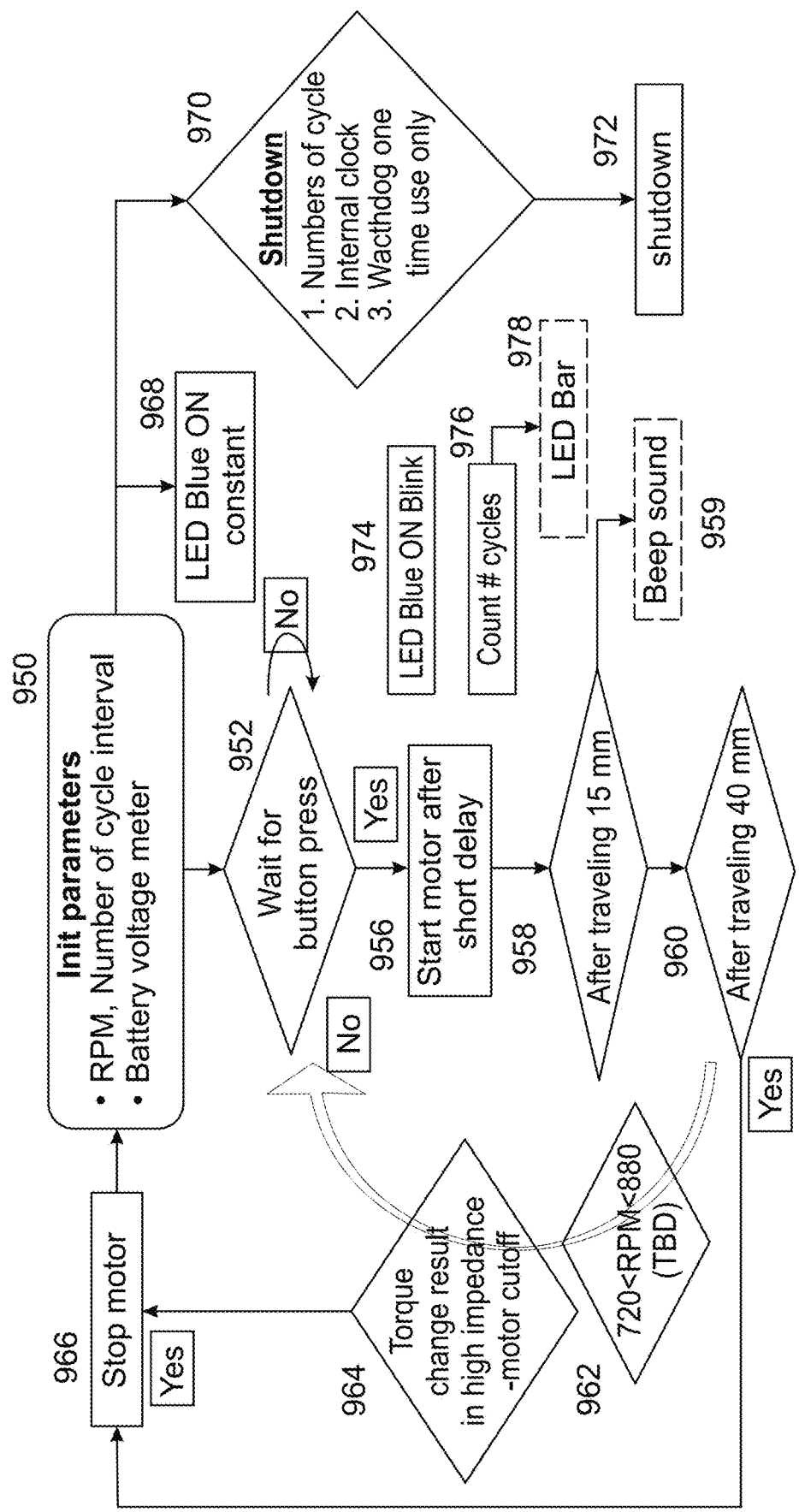
FIG. 9B is a flow chart of an activation process of a biopsy device, according to some embodiments of the invention.

Reference is now made to FIG. 9B depicting an operation process of a biopsy device, according to some exemplary embodiments of the invention.

According to some exemplary embodiments, when the biopsy device is activated, a controller, for example controller 904 shown in FIG. 9A sets values for some activation parameters at 950. In some embodiments, the activation parameters comprise RPM values, number of cycle intervals, duration of each rotation cycle and/or any activation parameter related to the activation of the biopsy device or to the biopsy sampling process. Optionally, the controller initiates a check to make sure that at least some of the hardware components of the biopsy device are intact and/or are connected to selected components of the device. Optionally, when the controller finishes the setting and checks, the controller shifts the device operation to a stand-by mode. N some embodiments, when the device is in a stand-by mode a visual indication is delivered to the user, for example a LED light is constantly on, by an interface of the control unit. Optionally, during the value setting and/or the hardware checking at 950 when encountering an error and/or when received values are not at desired range of values at 970, the device shuts down at 972.

According to some exemplary embodiments, the biopsy device waits for an activation command at 952. In some embodiments, the controller waits for an activation signal from activation circuit 910.

According to some exemplary embodiments, when an activation signal is received at 956, the motor starts to rotate. In some embodiments, when the motor rotates a visual indication is delivered to a user of the biopsy device at 974, for example by a blinking LED. Optionally, when the motor rotates, the number of rotor cycles, for example number of motor rotations is counted at 976 and optionally presented to the user by a visual indication at 978, for example by a LED bar.

According to some exemplary embodiments, after the motor rotates for a selected or a predetermined number of cycles and/or for a selected or predetermined time period, for example 15 minutes at 958, a visual and/or a sound indication is delivered to the user, for example by a beep sound at 959.

According to some exemplary embodiments, after the motor rotates for a maximal pre-determined or selected number of cycles, or for a maximal pre-determined time period at 960, the motor stops at 966. In some embodiments, if an activation button is released before reaching the pre-determined maximal activation period and/or before reaching the maximal number of cycles, the motor stops.

According to some exemplary embodiments, if the motor rotation is not at a predetermined RPM range at 962, the motor stops at 966. In some embodiments, if a torque change results in high temperature at 964, the motor stops at 966. In some embodiments, the device shutdown when the number of cycles excides, and/or when a controller failure is detected by watchdog timer and/or when the device is powered for more than a pre-determined time value.

Exemplary Sampling Portion Assembly

Figure 10A:
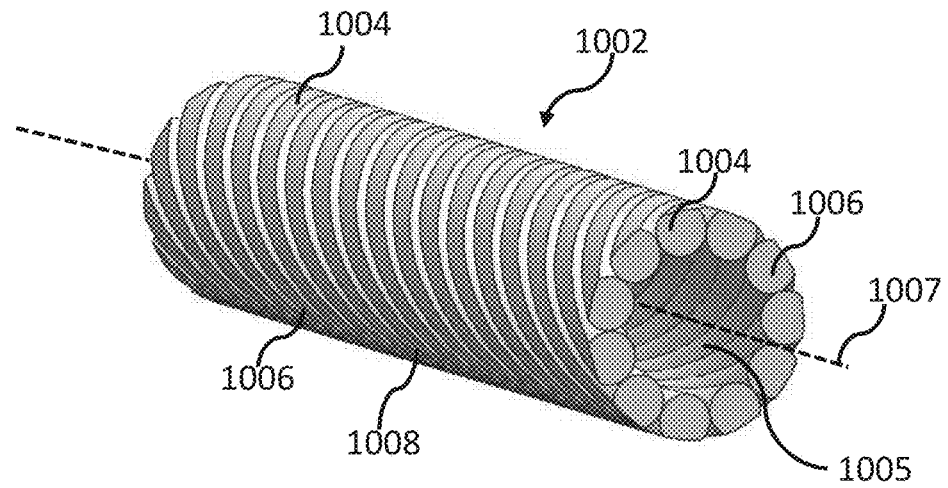
Figure 10B:
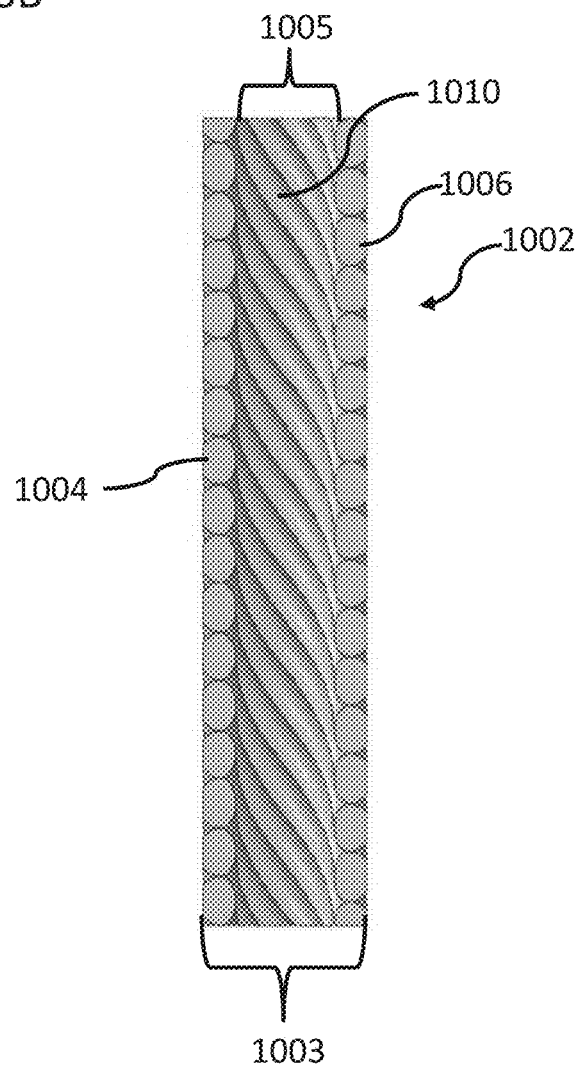

According to some exemplary embodiments, a sampling portion, for example a sampling needle or a sampling portion of a torque coil of the biopsy device is formed from at least one longitudinal extending wire, for example the at least one wire forming the torque coil. In some embodiments, the at least one longitudinal extending wire is twisted to form a tubular sampling needle having an inner lumen which is wide enough to accommodate a tissue sample. Reference is now made to FIGS. 10A and 10H, depicting a sampling needle assembly according to some exemplary embodiments of the invention.

According to some exemplary embodiments, a sampling portion 1002 comprises at least one wire, for example wires 1004 and 1006. Optionally, the at least one wire is a longitudinally extending wire. In some embodiments, the at least one wire is twisted, for example wires 1004 and 1006 are twisted together, to form a tubular hollow structure with an inner lumen 1005. In some embodiments, the inner lumen 1005 is shaped and sized to accommodate a tissue sample when the sampling portion penetrates into a tissue. In some embodiments, the at least one twisted wire is part of the hollow torque coil shaft.

According to some exemplary embodiments, an outer diameter (OD) of the sampling portion, for example sampling portion 1002 is in a range of 0.5 mm-3 mm, for example 0.5 mm-2 mm, 1 mm-2.5 mm, 1.8 mm-3 mm or any intermediate, smaller or larger range of values. In some embodiments, an inner diameter (ID) of the sampling portion, for example sampling portion 1002 is in a range of 0.1 mm-1.5 mm, for example 0.1 mm-0.8 mm, 0.5 mm-1.2 mm, 0.7 mm-1.5 mm or any intermediate, smaller or larger range of values. In some embodiments, a thickness of a wall of the sampling portion, for example sampling portion 1002 is in a range of 0.04 mm-1.5 mm, for example 0.04 mm-0.3 mm 0.1 mm-0.5 mm, 0.3 mm-0.8 mm, 0.7 mm-1.2 mm, 0.9 mm-1.5 mm or any intermediate, smaller or larger range of values.

According to some exemplary embodiments, the at least one twisted wire, for example wires 1004 and 1006, forms a sampling portion having grooves and/or indentations on the external surface of the sampling portion, for example external surface 1008. Alternatively or additionally, the at least one twisted wire forms a sampling portion having grooves and/or indentations on the internal surface of the sampling portion, for example internal surface 1010. Optionally, the external surface 1008 and/or the internal surface 1010 comprise one or more helical grooves extending along a longitudinal axis, for example axis 1007 of the sampling portion 1002. In some embodiments, the grooves and/or indentations form a pattern on the external surface of the sampling portion. Optionally, the grooves and/or indentations form a randomized pattern.

According to some exemplary embodiments, the sampling portion assembly is at least partly sharpened, for example to allow better gripping and/or collection of the tissue sample. Alternatively or additionally, the sampling portion assembly is at least partly sharpened, for example to form external and/or internal cutting edges to allow easier separation of the tissue sample from the tissue. Reference is now made to FIGS. 10C-10E depicting sharpening of the sampling portion assembly, according to some exemplary embodiments of the invention.

According to some exemplary embodiments, for example as shown in FIG. 10D the inner sampling portion assembly is internally remodeled, for example by internally sharpening. Alternatively or additionally, the sampling portion is remodeled by pressing the sampling portion against an element inserted into the lumen of the sampling portion. In some embodiments, internal diameter of the sampling portion 1014 near a distal opening 1016 is larger than a diameter of a proximal section 1019 of the sampling portion assembly 1014. In some embodiments, tissue penetrating through the distal opening 1016 into the sampling portion 1014, while the sampling portion 1014 axially advances into the tissue are condensed by an internal inverted tapered section 1018 of the sampling portion. A potential advantage of tissue condensation is that it increases the friction between the condensed tissue and the internal surface of the sampling portion, which optionally leads to an easier separation of the tissue sample from the tissue.

According to some exemplary embodiments, for example as shown in FIG. 10E, the sampling portion assembly, for example sampling portion assembly 1022 is externally remodeled. In some embodiments, the sampling portion assembly 1002 is externally remodeled to have a narrow external diameter near a distal opening 1024 of the sampling portion compared to an external diameter of a more proximal section, for example proximal section 1025 of the sampling portion assembly. In some embodiments, the externally remodeled sampling portion assembly 1022 comprises a tapered section 1026 towards the distal opening 1024.

According to some exemplary embodiments, the sampling portion assembly 1022 is externally remodeled by external sharpening of the sampling portion to form the tapered section 1026. Alternatively or additionally, the tapered section 1026 is formed using a shaping mold pressed against the internal surface of the sampling portion 1022.

According to some exemplary embodiments, in comparison to a sampling needle formed from Nitinol, for example sampling needle 1011, the sampling portion assemblies, optionally made from a hollow torque coil shaft, have a thicker wall, for example walls 1020 and 1025 of the sampling portions 1014 and 1022 respectively. In some embodiments, the thickness of the wall of the needle assemblies made from at least one twisted wire, for example needles formed from a torque coil, is at least 0.10 mm, for example 0.12 mm, 0.15 mm, 0.2 mm or any intermediate, smaller or larger value.

Figure 10F:
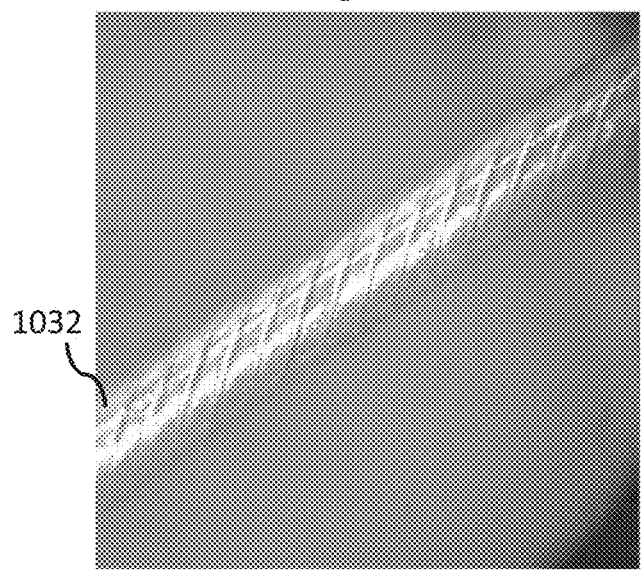
FIGS. 10F-10H are images of a sampling portion connected to a torque coil, according to some embodiments of the invention.
Figure 10G:
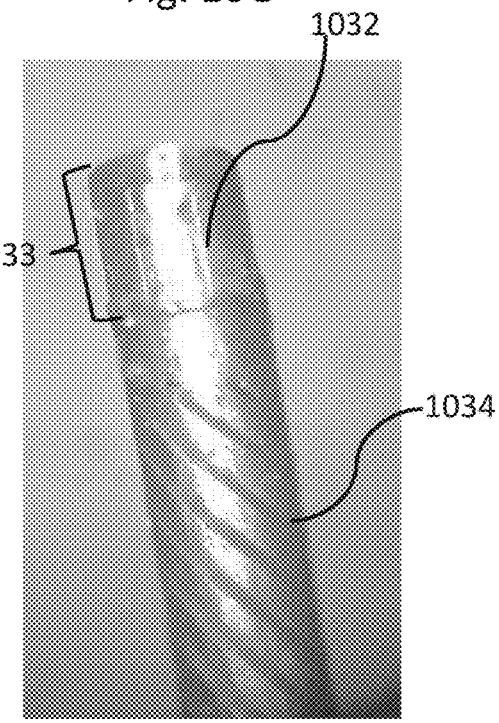
Figure 10H:
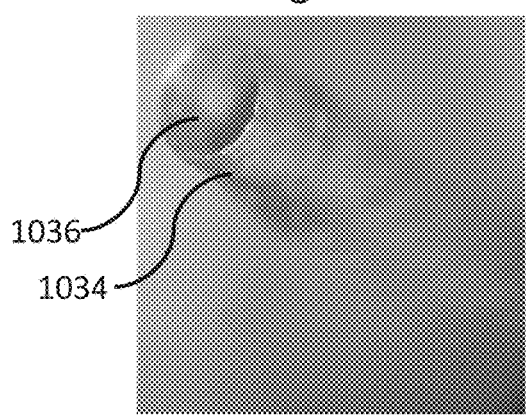

According to some exemplary embodiments, for example as shown in FIGS. 10F-10H, the sampling portion is welded or soldered to a hollow torque coil shaft. In some embodiments, a sampling portion 1032 having a length in a range of 2-40 mm, for example 2-30 mm, 10-35 mm, 25-40 mm or any intermediate smaller or larger range of values, is welded to a distal end of a hollow torque coil, for example coil 1034. In some embodiments, for example as shown in FIGS. 10G and 10H, the sampling portion 1032 is externally remodeled, optionally by sharpening the external surface of the sampling portion 1032. In some embodiments, the wall thickness of the sampling portion 1032 near a distal opening 1036 is narrower compared to the wall of the coil 1034. In some embodiments, the sampling portion is pre-formed. Optionally, the sampling portion is made from stainless components, for example stainless steel.

According to some exemplary embodiments, at least part of the sampling portion 1002 is covered by a covering tube, for example a heat shrink tubing, which is optionally a heat shrink PET, having a thickness in a range of 10-100 µm, for example a thickness in a range of 10-20 µm, 10-30 µm, 25-50 µm or any intermediate, smaller or larger value or range of values.

According to some exemplary embodiments, the sampling portion, for example sampling portion 1032 is formed by interweaving a plurality of wires, for example interweaving 2, 3, 4, 5, 6, 7, 8 or any larger number of wires. In some embodiments, the sampling portion is braided.

According to some exemplary embodiments, the sampling portion, for example a sampling portion which is part of a torque coil or attached to a torque coil or is a Nitinol sampling needle, axially advances into a target tissue without rotation, for example during a sampling process of the target tissue.

Exemplary Sampling Portion Assembly Echogenicity

Figure 11:
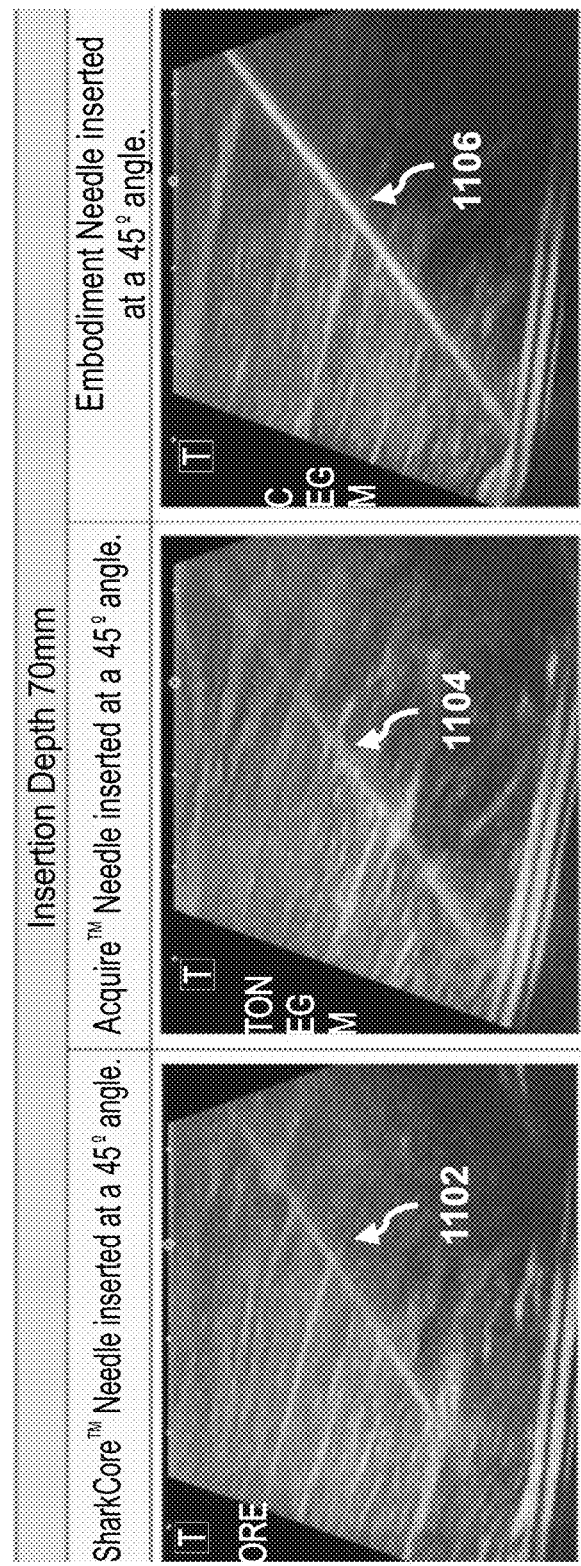
FIG. 11 is an image showing a comparison of echogenicity between a sampling portion assembly and other sampling needles, according to some embodiments of the invention.

According to some exemplary embodiments, a sampling portion formed from at least one wire, for example as shown in FIGS. 10A and 10B have better echogenicity compared to other sampling needles, for example as shown in FIG. 11.

According to some exemplary embodiments, a sampling portion assembly embodiment needle 1106, inserted at angle between 0-90 degrees, for example 45° degrees, has a better echogenicity compared to an Acquire™ needle 1104 and/or SharkCore™ needle 1102. In some embodiments, and without being bound by any theory, a patterned external surface of the sampling portion assembly which comprises grooves and/or indentations in different directions, for example helical grooves and/or angular grooves compared to the sampling portion longitudinal axis, reflect ultrasound waves more efficiently compared to a smooth external surface or an external having unidirectional grooves.

Exemplary Sampling Portion Assembly Bending

Figure 12A:
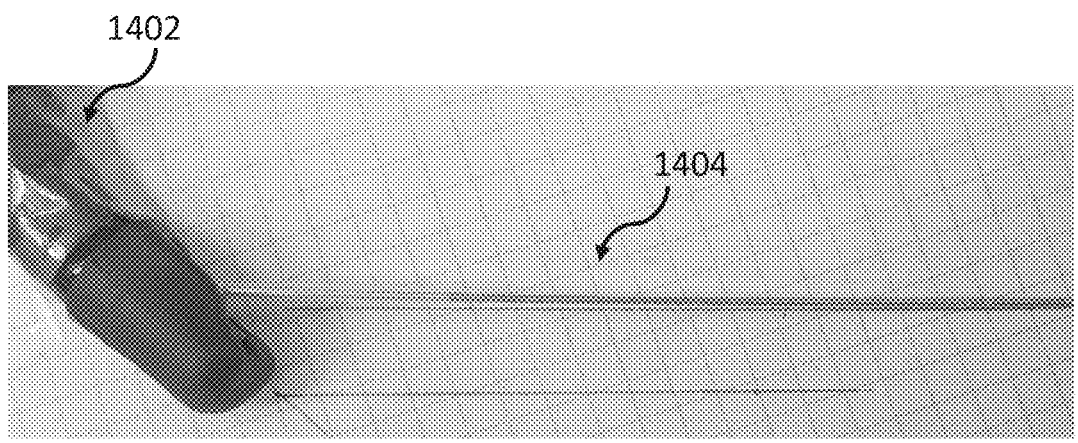
FIGS. 12A-12B are images showing bending of a sampling portion assembly according to some embodiments of the invention and in comparison with other sampling needles.
Figure 12B:
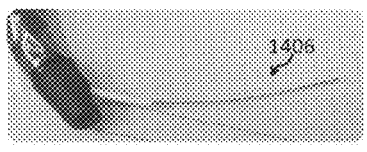
Figure 12B:
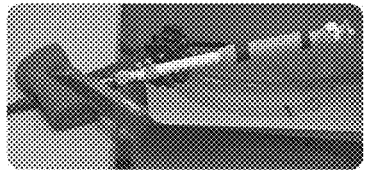
Figure 12B:
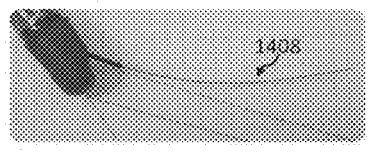
Figure 12B:
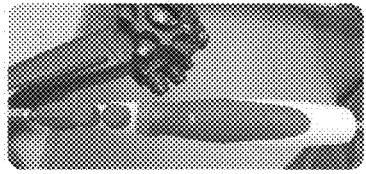
Figure 12B:
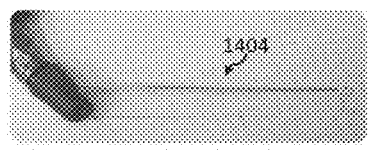
Figure 12B:

Reference is now made to FIGS. 12A and 12B depicting sampling portion assembly bending, according to some exemplary embodiments of the invention.

According to some exemplary embodiments, using a sampling portion assembly comprising at least one twisted wire, for example a sampling portion made from a torque coil shaft, allows elevating the sampling portion relative to an endoscope with less resistance compared to single unit sampling needles, for example Nitinol needles. In some embodiments, for example as shown in FIG. 12A, a torque coil shaft 1404 including a sampling portion is bend in about 45 degrees compared to an endoscope 1402. In some embodiments, the bended section is aligned with a deviation of less than 5% from fully alignment.

According to some exemplary embodiments, for example as shown in FIG. 12B, bending of standard biopsy needles, for example the SharkCore™ needle 1406 and the Acquire™ needle generates a deviation of at least 20 mm from fully alignment, along the bended section after more than 10 stabs of the needle. On the other hand, bending of the sampling portion assembly 1404, generates a deviation of less than 5% from fully alignment after 10 stabs.

A potential advantage of bending a sampling portion with less deviations after several stabs is that it allows to maintain sampling accuracy and/or safety during the tissue sampling process.

Exemplary Stylet Movement Control Mechanism

Reference is now made to FIGS. 13A-13D depicting a stylet movement control mechanism, according to some exemplary embodiments of the invention.

According to some exemplary embodiments, a tissue sampling device, for example sampling device 1302, comprises a stylet 1304 traveling in an inner lumen and along a longitudinal axis of the sampling device 1302. In some embodiments, the stylet 1304 is configured to move between a distal position, where the stylet occupies a sampling portion of the sampling device, and a proximal position, where the stylet is retracted from the sampling portion, for example to allow tissue sampling.

According to some exemplary embodiments, the device comprises at least one sensor positioned in the handle, for example a stylet position sensor 1310. In some embodiments, the stylet position senses whether the stylet is in a distal position or is retracted to a proximal position. Optionally, the device comprises at least two stylet positioning sensors, one sensor senses if the stylet is in a distal position and a second sensor senses if the stylet is in a proximal position. In some embodiments, the one or more stylet positioning sensors comprise an optical sensor configured to sense changes in light, for example when the stylet is retracted to a proximal position. Alternatively, the one or more stylet positioning sensors comprise an electrical sensor, configured to sense changes in one or more of electrical current, electrical voltage, and/or electrical impedance when the stylet moves.

According to some exemplary embodiments, the stylet 1304 is mechanically connected to a stylet knob, for example stylet knob 572 shown in FIGS. 5Q-5S. In some embodiments, when the stylet 1304 is at a distal position, the stylet knob 572 is located near a proximal end of a handle, optionally near an external surface of the handle. In some embodiments, a stylet movement control button, for example a stylet release button 1306 is mechanically connected to the stylet 1304 by a connecting shaft, for example plate 1308. In some embodiments, when the stylet 1304 is at a distal position, the stylet release button extends out from a handle surface, optionally through a side wall of the handle.

According to some exemplary embodiments, the stylet comprises at least two indentations at two different axial locations, for example a proximal indentation and a distal indentation. In some embodiments, the plate 1308 is configured to interact with the indentations, for example to lock the stylet at the distal position by interacting with the proximal indentation, or in a proximal position, for example by interacting with the distal indentation. Optionally, the plate 1308 is configured for interference locking of the stylet indentations, for example by at least one groove in the plate.

Figure 13A:
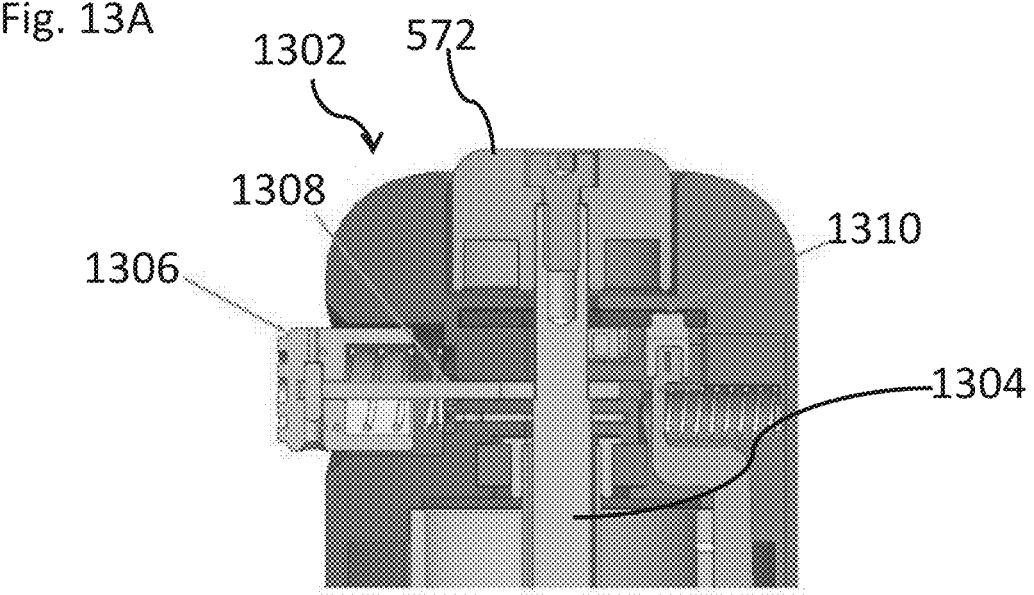
FIGS. 13A-13D are schematic illustration of a stylet movement control mechanism, according to some embodiments of the invention.
Figure 13B:
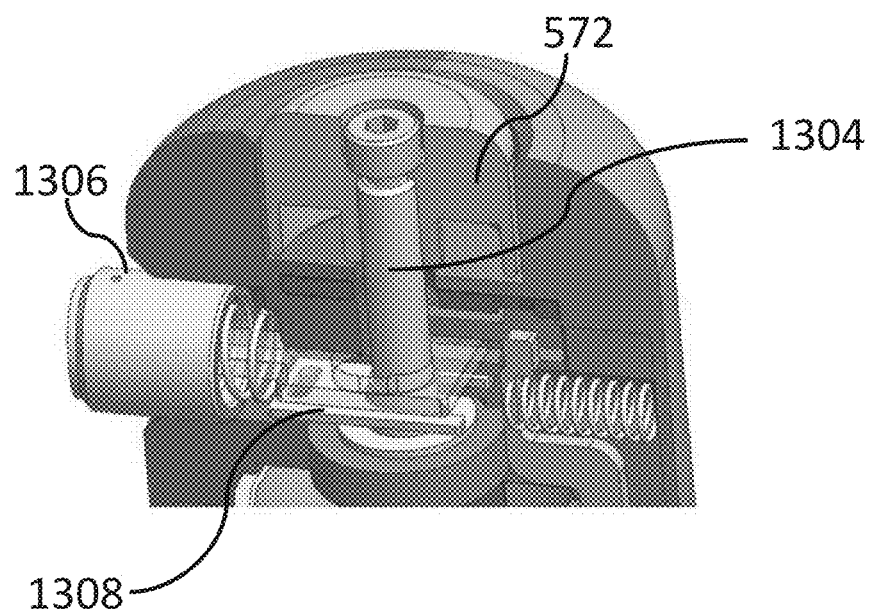
Figure 13C:
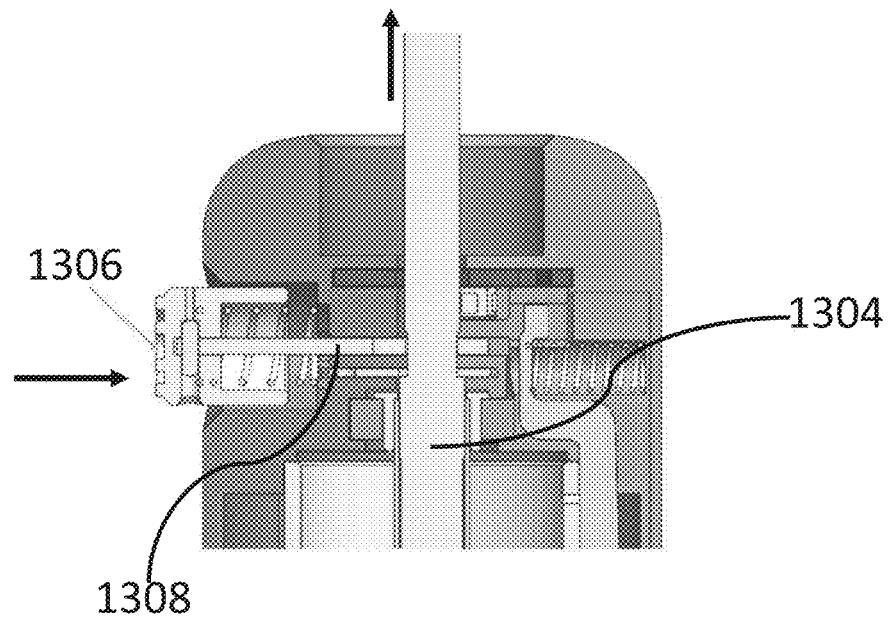
Figure 13D:
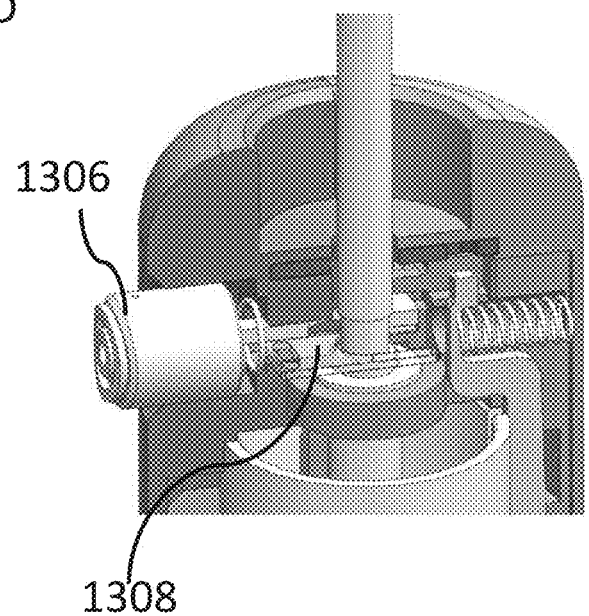

According to some exemplary embodiments, for example as shown in FIGS. 13C and 13D, when the stylet release button is pressed, the plate 1308 moves and releases the stylet, for example releases an indentation on the stylet. In some embodiments, when the stylet 1304 is released, the stylet is retracted to the proximal position. In some embodiments, the stylet 1304 is retracted to a pre-determined distance. Alternatively, the retraction distance of the stylet is adjusted by the user, for example according to tissue type and/or desired sample tissue volume. Optionally, the stylet is retracted by a pre-loaded energy source, for example a spring mechanically connected to the stylet. In some embodiments, when the stylet 1304 is retracted, the stylet knob 572 extends out from the handle.

According to some exemplary embodiments, when the stylet 1304 is at a proximal position, the plate 1308 locks the stylet, for example by interference locking with an indentation of the stylet, as described previously. In some embodiments, only when the stylet is at a proximal position, for example based on signals from one or more stylet positioning sensors, a control unit of the device signals a motor to axially advance the sampling portion into the tissue.

Exemplary Sheath Length Adjuster Lock

Figure 14A:
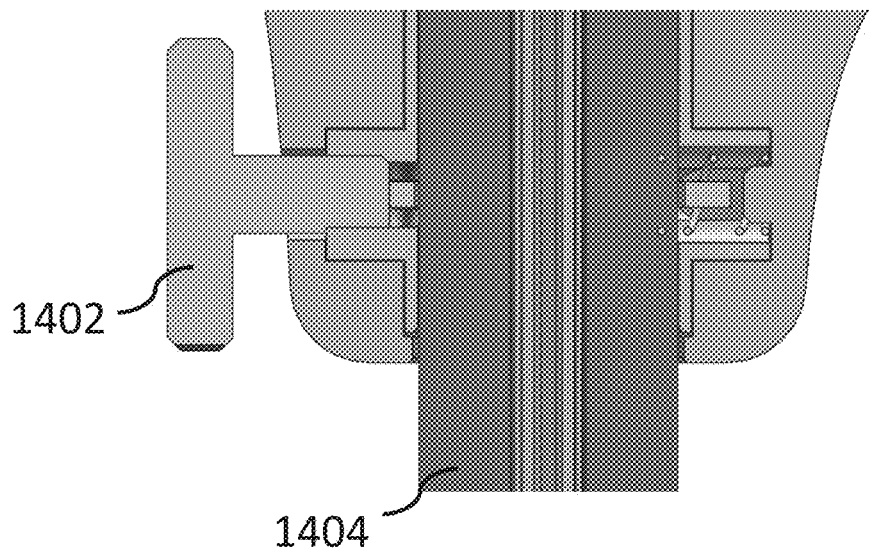
FIGS. 14A-14C are schematic illustrations of a sheath length adjuster lock, according to some embodiments of the invention.
Figure 14B:
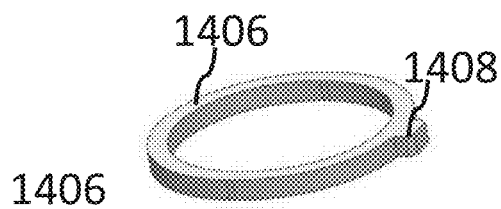
Figure 14C:
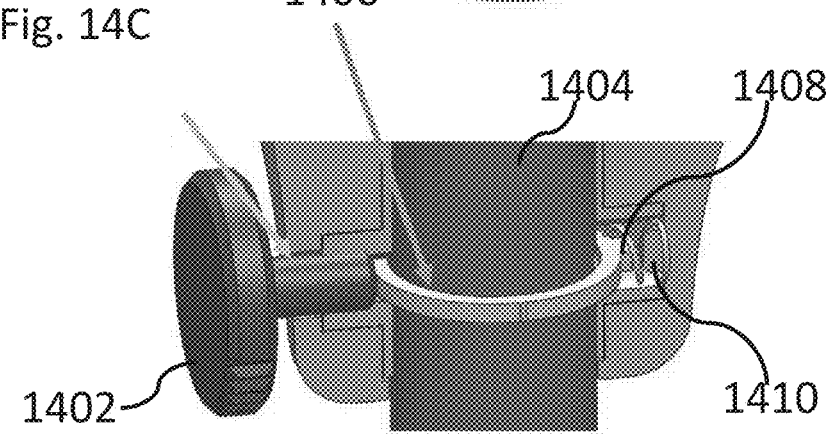

According to some exemplary embodiments, a user adjusts the length of the sheath prior to the sampling process, for example according to the length of the working channel of the endoscope. In some embodiments, once adjusted, the sheath is locked in an axial direction, for example to prevent lengthening or shortening of the sleeve during the sampling process. In some embodiments, locking the sheath movement in an axial direction allows rotation of the sleeve. Reference is now made to FIGS. 14A-14C depicting a sheath, also termed herein as a sleeve, length adjuster locking mechanism, according to some exemplary embodiments of the invention.

According to some exemplary embodiments, a sleeve length adjuster lock comprises a locking handle, for example a lever or a knob 1402, mechanically connected to a sleeve 1404. In some embodiments, the lock comprises a tightening interface having a flat surface which is shaped and sized to fit an external flat surface of the sleeve. Optionally, the tightening interface surrounds at least partly the sleeve. In some embodiments, the tightening interface, for example an arc or a ring, for example ring 1402, has a curved flat surface which fits a flat curved external surface of the sleeve 1404. In some embodiments, for example as show in FIG. 14C, pressing a flat surface of the curved interface, for example ring 1406 against the external curved surface of the sleeve 1404, locks the sleeve movement in an axial direction while allowing rotation of the sleeve.

According to some exemplary embodiments, the interface comprises at least one bulge, for example bulge 1408 at an opposite direction to the knob 1402. In some embodiments, pressing the knob 1402 against the interface, for example against the ring 1406, presses the bulge 1408 against a spring 1410 causing the spring 1410 to contract. In some embodiments, contraction of the spring 1410 causes the spring to apply a force on the tightening interface in an opposite direction to the force applied by the knob 1402 on the tightening interface. In some embodiments, the two opposite forces simultaneously tighten the interface, for example ring 1406 to the sleeve 1404.

Exemplary Preloaded Energy Source

Figure 15:
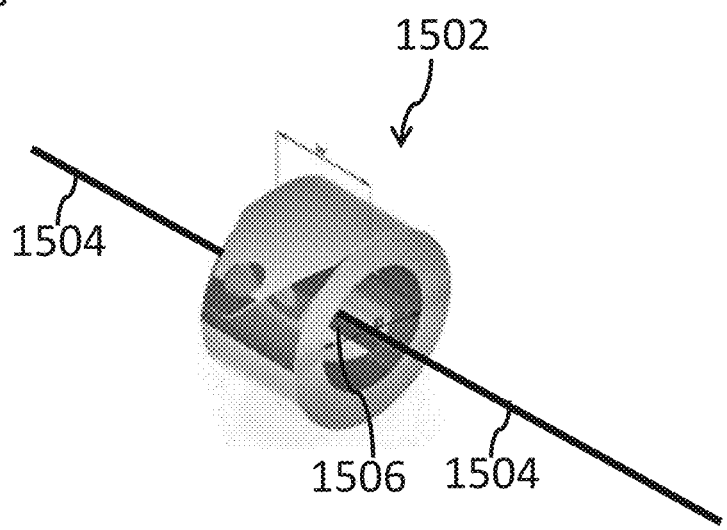
FIG. 15 is a schematic illustration of a pre-loaded spring of the sampling device, according to some embodiments of the invention.

According to some exemplary embodiments, the sampling device comprises at least one preloaded energy source, for example at least one spring, for example spring 1502 shown in FIG. 15. In some embodiments, the spring is a constant force spring. In some embodiments, the at least one preloaded energy source turns and/or axially advances the sampling portion, for example the sampling needle, during the sampling process. In some embodiments, the at least one preloaded energy source replaces an electrical energy. In some embodiments, the at least one preloaded energy source is loaded by a user, for example by turning a lever or a shaft mechanically connected to the at least one preloaded energy source.

According to some exemplary embodiments, the at least one preloaded energy source, for example spring 1502, is positioned in the handle of the biopsy device. In some embodiments, the torque coil, for example torque coil 1504 passes through an inner channel, for example channel 1506. In some embodiments, the channel 1506 is perpendicular to the rotational axis of the spring 1502.

According to some exemplary embodiments, the at least one preloaded energy source is replaceable. In some embodiments, the preloaded energy source is replaced through an opening in the biopsy device, for example through an opening in the handle of the biopsy device. In some embodiments, the preloaded energy source is replaced during the sampling process, for example between each stabbing of the tissue. In some embodiments, the at least one preloaded energy is combined with an operation of an electric motor. In some embodiments, the electric motor provides energy for axially advancing the biopsy needle into the tissue and the preloaded energy source rotates the biopsy needle.

Exemplary Biopsy Guide

According to some exemplary embodiments, a biopsy guide comprises an elongated handle and an elongated shaft passing through an internal lumen of the handle. In some embodiments, the elongated shaft comprises a sampling portion, for example a biopsy needle at a distal end of the shaft facing the tissue. In some embodiments, the shaft comprises a braided coil or a braided tube, for example braided tube 805 shown in FIG. 8A.

According to some exemplary embodiments, the sampling portion, for example sampling portion 1002 shown in FIGS. 10A and 10B, is a braided coil. In some embodiments, for example as shown in FIG. 10G, the sampling portion is formed by sharpening the distal end of the braided coil, for example coil 1034. Alternatively, a sharpened sampling portion is welded or is attached to the braided coil.

According to some exemplary embodiments, the biopsy guide comprises the components of the biopsy devices described in FIGS. 4F-4H, and/or in FIGS. 5A-5S, without a driving unit and a motor which is configured to rotate a shaft with a sampling portion, and without a control unit which is configured to control the rotation of the sampling portion. In some embodiments, the biopsy guide does not include a power source, for example a battery for delivery of electrical power to one or more of the biopsy guide components.

According to some exemplary embodiments, the biopsy guide is a motor-driven biopsy guide, comprising a driving unit having a motor which is configured to axially move the sampling portion into a tissue and/or axially retract the sampling portion from the tissue. In some embodiments, the motor-driven biopsy guide comprises a control unit, configured to control the axial movement of the sampling portion.

Figure 16A:
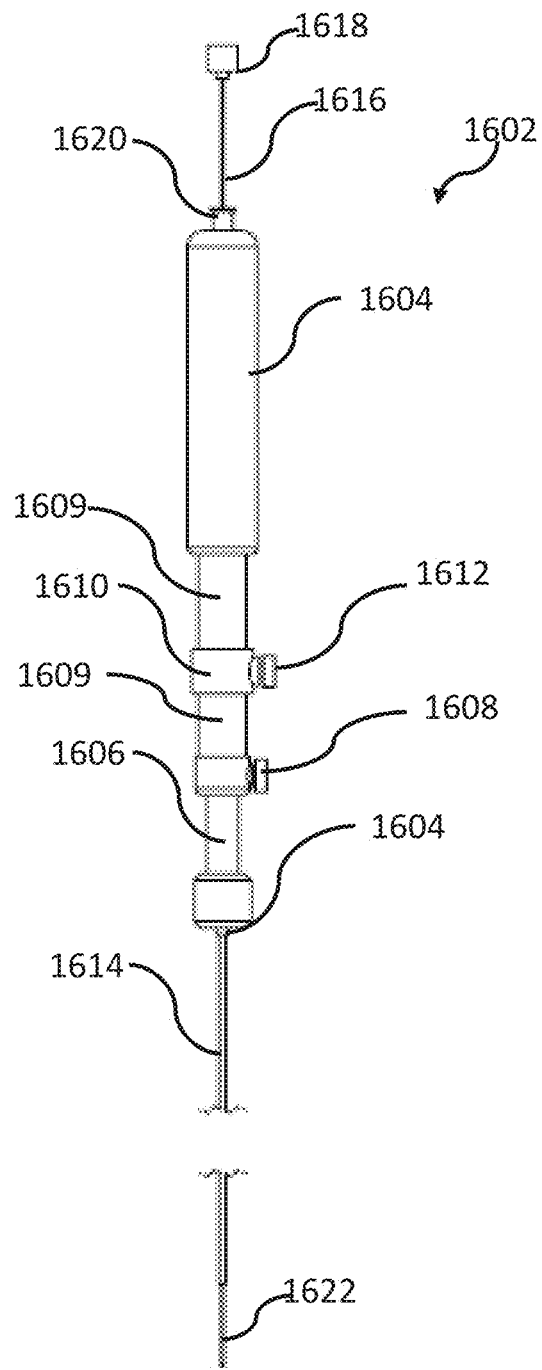
FIG. 16A is a schematic illustration of biopsy guide, according to some embodiments of the invention
Figure 16B:
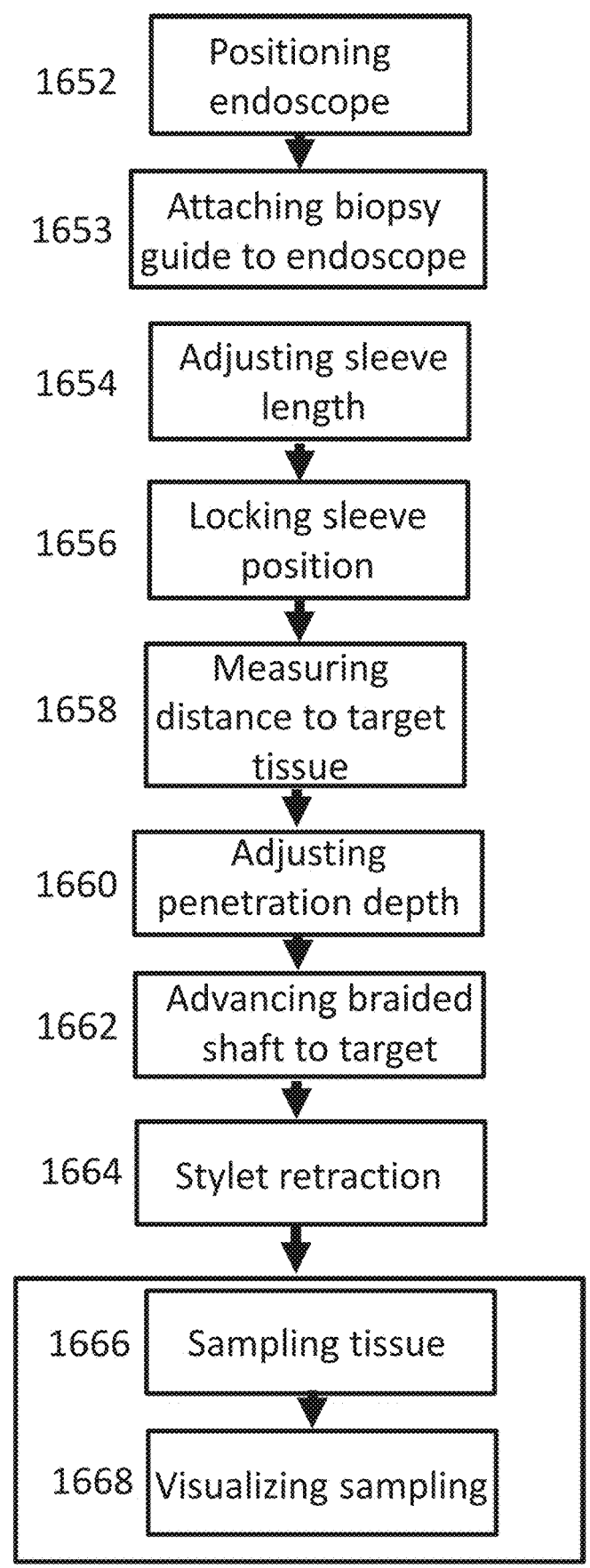
FIG. 16B is a flow chart of a detailed process for tissue sampling using a non-rotating sampling device, according to some embodiments of the invention.

Reference is now made to FIG. 16A, depicting a biopsy guide, according to some exemplary embodiments of the invention.

According to some exemplary embodiments, a biopsy guide comprises a sampling needle which is formed from two or more segments, for example two or more cables or wires, interweaved together, for example to form a braided sampling needle. In some embodiments, the sampling needle comprises a pattern on an external surface of the sampling needle that is formed by the merging of the two or more segments. Optionally, the pattern on the external surface reflects ultrasound waves more efficiently back towards an ultrasound transducer.

According to some exemplary embodiments, a biopsy guide, for example a biopsy guide 1602 comprises a handle 1604 with at least one inner channel, for example an inner longitudinal channel. In some embodiments, an elongated shaft, for example a braided coil comprising a sampling portion 1622, for example a biopsy needle, at a distal end of the elongated shaft, passes at least partly through the inner longitudinal channel. Optionally, the elongated shaft is a hollow shaft, for example a hollow braided coil. In some embodiments, the handle 1604 is fixatedly attached to the shaft, for example to control the axial movement of the sampling portion 1622. In some embodiments, the handle manually controls the axial advancement of the sampling portion. Alternatively, biopsy guide is a motor-driven biopsy guide, and a motor controls the axial advancement of the sampling portion.

According to some exemplary embodiments, the handle 1604 is configured to slide over or slide within a tubular biopsy guide body 1609. In some embodiments, the handle 1604 telescopically slides over or within the tubular biopsy guide body 1609.

According to some exemplary embodiments, the biopsy guide comprises a stylet, for example a stylet 1616. In some embodiments, the stylet is a flexible stylet, for example the flexible stylet 806 shown in FIGS. 8B and 8D. In some embodiments, the stylet 1616 passes through the hollow braided coil and the sampling portion, for example as shown 8B. In some embodiments, the flexible stylet 1616 passes through the sampling portion for example, to increase rigidity of the braided coil.

According to some exemplary embodiments, the stylet 1616 comprises a stylet knob 1618, for example to allow manual retraction of the stylet 1616. In some embodiments, the stylet knob 1618 is located at a proximal end of the stylet 1616, positioned outside the body.

According to some exemplary embodiments, the biopsy guide 1602 comprises a stopper, for example stopper 1610, configured to limit the handle 1604 axial range of movement, for example the sliding of the handle 1604 with respect to the biopsy guide body 1609. In some embodiments, the stopper 1610 comprises a stopper lock, for example a stopper knob 1612, configured to control the movement of the stopper 1610 over the biopsy guide body 1609. In some embodiments, in a relaxed state, the stopper knob 1612 applies friction forces between the stopper 1610 and the biopsy guide body 1609. In some embodiments, applying an external force on the stopper knob 1612 reduce the friction forces and allow re-positioning of the stopper 1610 on the body 1609.

According to some exemplary embodiments, the biopsy guide 1602 comprises a sleeve length adjuster 1606. In some embodiments, the braided coil is covered at least partly with a sleeve, also termed herein as sheath. In some embodiments, the sleeve is shaped and sized to protect bodily tissues from contacting the braided coil and/or the sampling portion as the braided coil advances into the body and optionally towards a selected tissue target. In some embodiments, the length of the sleeve is adjusted to fit a length of an endoscope's working channel.

According to some exemplary embodiments, the sleeve length adjuster is connected, optionally fixatedly connected, to a sleeve 1614. In some embodiments, the sleeve length adjuster is configured to axially slide within an internal lumen of body 1609. In some embodiments a sleeve adjuster lock, for example a sleeve adjuster knob 1608 is positioned on the body 1609. Optionally, the sleeve adjuster knob is positioned at least partly around the body 1609.

According to some exemplary embodiments, the sleeve adjuster knob 1608 is configured to limit the sliding movement of the sleeve adjuster 1606 with respect to the body 1609. In some embodiments, the sleeve adjuster knob 1608 applies external force on the body 1609, for example to press the inner surface of the body 1609 against the external surface of the sleeve adjuster 1606. In some embodiments, pressing the body 1609 against the sleeve adjuster 1606 applies friction forces on the sleeve adjuster 1606, which are sufficient to limit the movement, for example the sliding of the sleeve adjuster 1606.

According to some exemplary embodiments, a distal end of biopsy guide body 1609 comprises an endoscope lock 1604, for example a luer lock. In some embodiments, the endoscope lock is configured to lock the biopsy guide 1602 to an endoscope, for example to prevent bodily tissues and liquids to exit at an interface point between the endoscope and the biopsy guide body 1609.

According to some exemplary embodiments, the biopsy guide 1602 comprises an external fluid line connector 1620. In some embodiments, the connector 1620 is configured to allow connection of an external fluid flow path to the flow path within the hollow braided coil. In some embodiments, connecting an external fluid flow path to the braided coil allows to pass fluids through the hollow braided coil and the sampling portion into the body. In some embodiments, the connector 1620 is shaped and sized to allow connection of a syringe outlet to the braided coil. Optionally, the connector 1620 is a luer connector.

Exemplary Tissue Sampling Using a Biopsy Guide

According to some exemplary embodiments, the biopsy guide is used to guide a sampling portion, for example a biopsy needle, into a tissue. In some embodiments, the sampling portion axially advances into the tissue. Additionally or optionally, the sampling portion rotates at a rotation angle smaller than 90 degrees, for example at a rotation angle smaller than 5 degrees, at a rotation angle smaller than 10 degrees, at a rotation angle smaller than 20 degrees, at a rotation angle smaller than 30 degrees or any intermediate, smaller or larger rotation angle. Reference is now made to FIG. 16B and FIGS. 17A-17L, depicting a tissue sampling process using a biopsy guide, according to some exemplary embodiments of the invention.

According to some exemplary embodiments, an endoscope is introduced into the body and is positioned at a selected location at 1652. In some embodiments, a distal opening of the endoscope working channel is positioned at a desired distance from a target tissue.

According to some exemplary embodiments, a biopsy guide, is attached to the endoscope at 1653. In some embodiments, the biopsy guide, for example biopsy guide 1062 shown in FIGS. 17A and 17B is attached to a proximal opening of the endoscope's working channel.

According to some exemplary embodiments, a length of a biopsy guide sleeve is adjusted at 1654. In some embodiments, the sleeve length, for example sleeve 1614 length is adjusted according to an inner length of the endoscope working channel. In some embodiments, for example as shown in FIGS. 17C and 17D, the sleeve length is adjusted by sliding the sleeve length adjuster 1606 within an inner lumen of the biopsy guide body 1609. In some embodiments, the sleeve length adjuster shortens and/or extends the length of the sleeve.

According to some exemplary embodiments, once a desired sleeve length is reached, a sleeve adjuster lock, for example sleeve adjuster knob 1608 locks the sleeve position at 1656. In some embodiments, the sleeve adjuster lock locks the position of the sleeve adjuster 1606 by directly or indirectly applying force on a portion of the sleeve adjuster positioned within the body 1609.

According to some exemplary embodiments, a distance between a portion of the biopsy guide within the body and a selected target tissue is measured at 1658. In some embodiments, the distance between a distal end of the sleeve or a distal end of the sampling portion and a selected target tissue is measured at 1658.

According to some exemplary embodiments, a penetration depth of the sampling portion into the target tissue is adjusted at 1660. In some embodiments, the penetration depth is adjusted according to a type of the target tissue or according to the mix of tissue types at the target tissue. Alternatively or additionally, the penetration depth is adjusted according to a desired tissue sample volume. Alternatively or additionally, the penetration depth is adjusted according to a clinical application. In some embodiments, the penetration depth is adjusted by adjusting a position of a stopper, for example stopper 1610 on the biopsy guide body 1609, for example as shown in FIGS. 17E and 17F. In some embodiments, a stopper lock 1612 locks the stopper 1610 at a selected position on the body 1609.

Figure 17G:
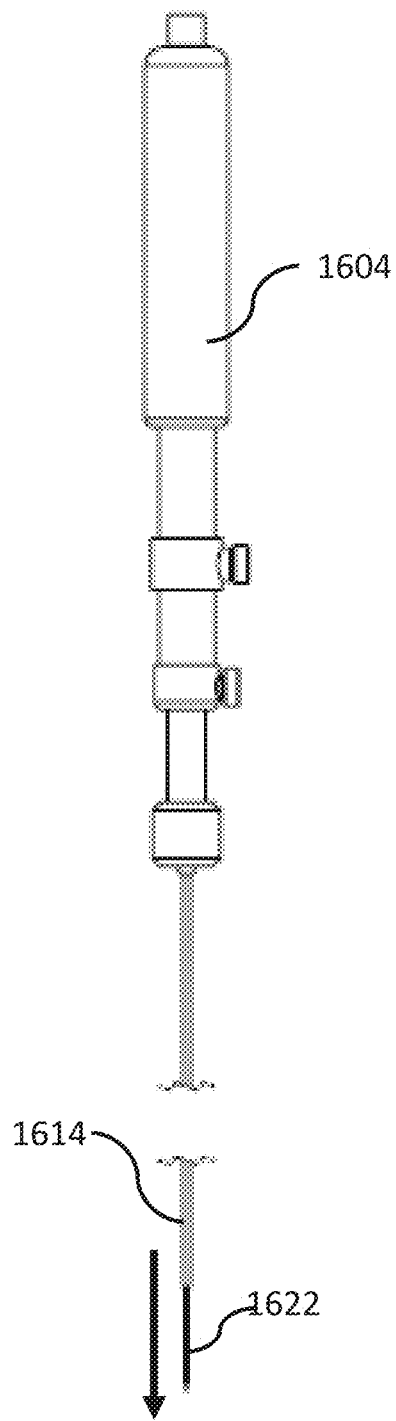
Figure 17H:
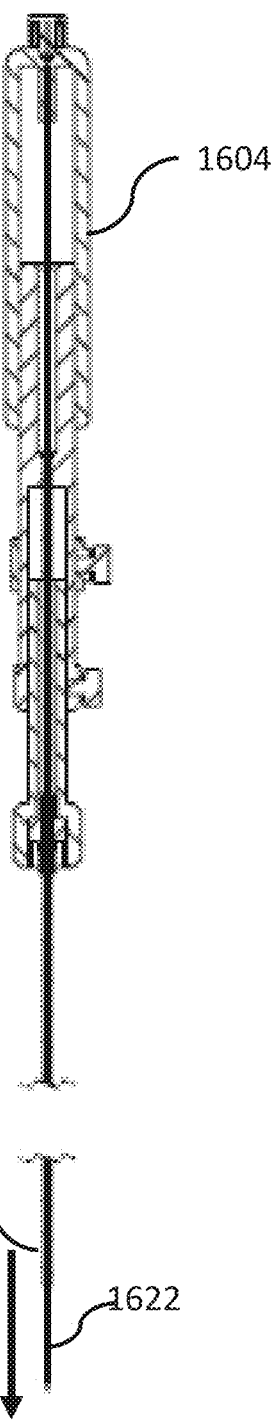

According to some exemplary embodiments, a braided shaft, for example a braided coil comprising a sampling portion is advanced towards a target tissue at 1662. In some embodiments, the sampling potion, for example a biopsy needle of the braided shaft is advanced until reaching a selected distance from the outer surface of the target tissue. In some embodiments, for example as shown in FIGS. 17G and 17H, the sampling portion is manually advanced by movements of the handle 1604, for example rotation movements of the handle or axial movements of the handle 1604. Optionally, the handle movements are manual movements. In some embodiments, the sampling portion advances by manually advancement of the handle 1604.

According to some exemplary embodiments, an inner stylet passing at least partly along an inner lumen of the sampling portion is retracted at 1664. In some embodiments, a stylet knob, for example a stylet knob 1618 mechanically connected to the stylet, for example stylet 1618 is retracted. In some embodiments, the stylet is retracted manually by a user. Alternatively, the stylet is retracted automatically by an actuator of the device. In some embodiments, the stylet is retracted to selected distance based on one or more of: desired tissue sample volume or quantity, and/or tissue type. In some embodiments, when reaching the selected retraction distance the stylet position is fixed, for example to prevent movement of the stylet when sampling the tissue.

According to some exemplary embodiments, tissue is sampled at 1668. In some embodiments, the tissue is sampled by stabbing the tissue with the sampling portion 1622. In some embodiments, during stabbing the sampling portion is axially advanced into the tissue. Optionally, the sampling portion is repeatedly advanced into the tissue and retracted from the tissue. In some embodiments, during the stabbing, the sampling portion is rotated in a rotation angle smaller than 90° degrees, for example in a rotation angle of 80° degrees, 40° degrees, 30° degrees, 10° degrees or any intermediate, smaller or larger rotation angle. In some embodiments, the sampling portion rotates to improve the separation of the tissue sample from the tissue. In some embodiments, during the stabbing, the sampling portion rotates at opposite directions.

According to some exemplary embodiments, the tissue sampling is visualized at 1668. In some embodiments, the sampling portion, for example a needle, also termed herein as a sampling needle, comprises a hollow braided coil, a hollow braided cable, or a twisted cable formed from a plurality of wires. In some embodiments, the needle is shaped and sized to allow better echogenicity of the sampling portion. In some embodiments, an external pattern of the braiding or cable twisting forming the needle is configured to reflect ultrasound waves transmitted from an ultrasound device. In some embodiments, reflecting the ultrasound waves allows visualization of the sampling portion with respect to the tissue being sampled and/or with respect to other parts of the device.

It is expected that during the life of a patent maturing from this application many relevant biopsy devices will be developed; the scope of the term sampling portion of a biopsy device is intended to include all such new technologies a priori. As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A soft tissue biopsy device comprising:
   an elongated flexible shaft having an internal lumen and a distal end, wherein said elongated flexible shaft is shaped and sized to be introduced via a working channel of an endoscope into a body;
   a distal cylindrical hollow sampling portion coupled to said elongated flexible shaft distal end, having a flat distal end, a wall defining and surrounding an enclosed internal lumen, a distal round front opening to said enclosed internal lumen at said flat distal end, and a circumferential round cutting edge surrounding said distal round front opening, wherein said circumferential round cutting edge is shaped and sized to form a round cut in said soft body tissue when penetrating into said soft body tissue, wherein said distal cylindrical hollow sampling portion is configured to cut through soft body tissue while penetrating into said soft body tissue, and to apply forces on tissue positioned inside said internal lumen of said distal cylindrical hollow sampling portion that are sufficient to separate tissue inside said internal lumen from the soft body tissue outside said distal cylindrical hollow sampling portion;
   at least one motor functionally coupled to said elongated flexible shaft configured to rotate and axially advance in synchronization and in a fixed ratio said elongated flexible shaft and said distal cylindrical hollow sampling portion comprising said circumferential round cutting leading edge, into the tissue, wherein the rotation of the distal cylindrical hollow sampling portion separates a tissue sample from the soft body tissue.

2. The biopsy device according to claim 1, wherein said circumferential cutting leading edge has an external and/or an internal circumferential tapered region.

3. The biopsy device according to claim 1, wherein said at least one motor comprises a gear motor configured to rotate and axially advance said elongated flexible shaft and said sampling needle in synchronization according to a selected ratio between rotation velocity and axial advancement velocity.

4. The biopsy device according to claim 3, wherein said ratio is pre-determined according to tissue type and/or tissue properties.

5. The biopsy device according to claim 1, wherein a diameter of said distal opening is in a range of 0.3 mm to 5 mm.

6. The biopsy device according to claim 1, wherein said sampling needle is a replaceable needle.

7. The biopsy device according to claim 1, wherein said elongated flexible shaft comprises a torque coil formed from at least one wire.

8. The biopsy device of claim 7, wherein a thickness of a wall of said sampling portion is in a range between 0.04 mm-0.5 mm.

9. The biopsy device according to claim 1, comprising a sharp stylet shaped and sized to be advanced forward and to be retracted within said internal lumen of said shaft.

10. The biopsy device according to claim 1, wherein an external surface of said sampling portion is at least partly covered with a sealing tubing, wherein said sealing tubing prevents the release of a tissue sample and/or liquids within said sampling portion through a wall of said sampling portion.

11. The biopsy device according to claim 1, wherein an external surface of said sampling needle is at least partly covered by a low-friction layer configured to reduce friction with surrounding tissue during a movement of the distal cylindrical hollow sampling portion.

12. The biopsy device according to claim 1, wherein at least part of an external surface of said elongated flexible shaft comprises one or more axially and circumferential spaced-apart grooves and/or indentations shaped and sized to reflect ultrasonic waves in different directions.

13. The biopsy device according to claim 1, wherein said at least one motor rotates said sampling portion intermittently in rotation pulses and/or in a variable rotation speed.

14. The biopsy device according to claim 1, wherein said at least one motor rotates said sampling portion at opposite directions.

15. The biopsy device according to claim 1, wherein said at least one motor rotates said sampling portion at a rotation angle smaller than 360° degrees.

16. A method for sampling soft tissue, comprising:
   introducing an elongated flexible shaft and a sampling needle coupled to said elongated flexible shaft into a body via a working channel of an endoscope, wherein said sampling needle comprises a distal cylindrical hollow sampling portion having a flat end, an internal lumen and a distal opening, and a circumferential round cutting leading edge at the flat end and surrounding said distal opening, wherein said circumferential round cutting leading edge is shaped and sized to cut through soft body tissue when advancing said sampling needle into soft body tissue;
   rotating said elongated flexible shaft and said sampling needle;

axially advancing said elongated flexible shaft and said sampling needle during said rotating into soft tissue in synchronization with said rotating and in a fixed ratio between said rotating and said axially advancing, while introducing a portion of said soft body tissue into said internal lumen through said distal opening;

sampling said soft body tissue by applying forces on said soft body tissue portion during said rotating, wherein said rotating and said forces separate a tissue sample from said soft tissue.

17. The method according to claim 16, comprising:
adjusting rotation speed and/or axial advancement velocity of said sampling portion according to a type and/or properties of said soft tissue.

18. The method according to claim 16, wherein said sampling comprises separating said tissue sample from said soft tissue by applying shearing forces.

19. The method according to claim 16, wherein said rotating comprises rotating said elongated flexible shaft and said sampling needle while said elongated flexible shaft is bent outside and distally to said working channel in said body, in an elevation angle of up to 50 degrees relative to said endoscope.

20. The method according to claim 16, wherein said rotating comprises rotating said elongated flexible shaft and said sampling needle with a speed in a range of 100 revolutions-per-minute (RPM) to 10,000 RPM.

21. The biopsy device according to claim 1, wherein said at least one motor is configured to rotate said elongated flexible shaft and said sampling needle with a speed in a range of 100 revolutions-per-minute (RPM) to 10,000 RPM and to said axially advance said hollow distal sampling portion into the tissue in synchronization with said rotation.

22. The biopsy device of claim 1, wherein a portion of said elongated flexible shaft extending out from said working channel and comprising said distal cylindrical hollow sampling portion is configured to bend, in an elevation angle of up to 50 degrees relative to an unbent portion of the elongated flexible shaft located within said working channel, while being rotated and axially advanced by said driving unit.

23. The biopsy device of claim 14, comprising a memory and a controller, wherein said controller signals said at least one motor to rotate in opposite direction according to values of one or more rotation parameters stored in said memory.

24. The biopsy device according to claim 1, comprising a handle coupled to said elongated flexible shaft, wherein said handle comprises a user interface configured to control an activation of said at least one motor.

25. The biopsy device according to claim 1, wherein said hollow sampling portion comprises at least one internal protrusion for applying friction forces on said tissue inside said internal lumen that are sufficient to hold said tissue within the internal lumen.

26. The biopsy device according to claim 24, comprising a control unit functionally coupled to said elongated flexible shaft, wherein activation of said at least one motor to rotate and axially advance said elongated flexible shaft and said distal cylindrical hollow sampling portion, axially advances said handle relative to said control unit.

27. The biopsy device according to claim 24, comprising a control unit functionally coupled to said elongated flexible shaft and comprising said at least one motor.

28. The biopsy device according to claim 1, wherein said at least one motor is further configured to axially advance said distal cylindrical hollow sampling portion in a velocity within a range between 0.4 mm/sec to 50 mm/sec into the tissue.

29. The biopsy device according to claim 16, wherein said axially advancing comprises axially advancing said elongated flexible shaft and said sampling needle in a velocity value within a range between 0.4 mm/sec to 50 mm/sec.

* * * * *